United States Patent
Dacres et al.

(10) Patent No.: US 11,952,612 B2
(45) Date of Patent: Apr. 9, 2024

(54) PROTEASE SENSOR MOLECULES

(71) Applicant: Commonwealth Scientific and Industrial Research Organisation, Acton (AU)

(72) Inventors: Helen Dacres, Werribee (AU); Stephen Charles Trowell, Oxley (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 854 days.

(21) Appl. No.: 16/349,237

(22) PCT Filed: Nov. 13, 2017

(86) PCT No.: PCT/AU2017/051237
§ 371 (c)(1),
(2) Date: May 10, 2019

(87) PCT Pub. No.: WO2018/085895
PCT Pub. Date: May 17, 2018

(65) Prior Publication Data
US 2019/0345535 A1   Nov. 14, 2019

(30) Foreign Application Priority Data

Nov. 14, 2016 (AU) ............................ 2016904639
Jan. 19, 2017 (AU) ............................ 2017900161

(51) Int. Cl.
*C12Q 1/37* (2006.01)
*C12Q 1/06* (2006.01)
(Continued)

(52) U.S. Cl.
CPC .............. *C12Q 1/37* (2013.01); *C12Q 1/06* (2013.01); *G01N 21/76* (2013.01); *G01N 33/52* (2013.01); *G01N 2333/21* (2013.01)

(58) Field of Classification Search
CPC ... C12Q 1/06; C12Q 1/37; C12Q 1/04; G01N 21/76; G01N 33/52; G01N 2333/21
See application file for complete search history.

(56) References Cited

U.S. PATENT DOCUMENTS 4,891,120 A   1/1990 Sethi et al.
4,908,112 A   3/1990 Pace
(Continued)

FOREIGN PATENT DOCUMENTS

AU   2015243093        11/2015
AU   2015243093 A1 †   11/2015
(Continued)

OTHER PUBLICATIONS

Chabala Current Opinion in Biotechnology, 1995, 6:632-639.*
(Continued)

*Primary Examiner* — Sean C. Barron
(74) *Attorney, Agent, or Firm* — Bozicevic, Field & Francis LLP; Shweta Chandra

(57) ABSTRACT

The present invention relates to sensors and methods for detecting bacterial proteases in a sample. In particular, the present invention relates to sensors and methods for detecting *Pseudomonas* spp. protease activity in a sample. The sensors and methods may be used to detect or predict spoilage of a dairy product. The invention also relates to methods for preparing samples for protease assays.

16 Claims, 18 Drawing Sheets

Figure 1:
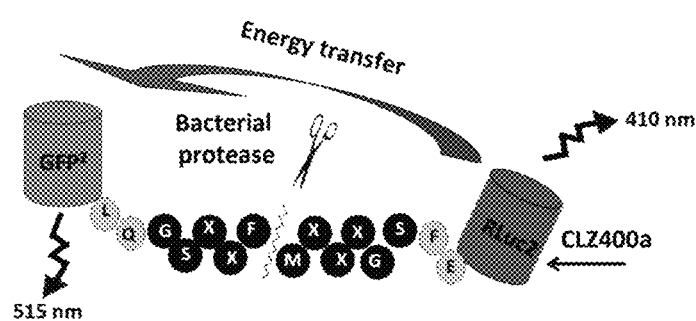

Specification includes a Sequence Listing.

(51) Int. Cl.
  *G01N 21/76* (2006.01)
  *G01N 33/52* (2006.01)

(56) References Cited

U.S. PATENT DOCUMENTS

| | | | |
|---|---|---|---|
| 5,126,022 | A | 6/1992 | Soane et al. |
| 5,196,524 | A | 3/1993 | Gustafson et al. |
| 5,219,737 | A | 6/1993 | Kajiyama et al. |
| 5,229,285 | A | 7/1993 | Kajiyama et al. |
| 5,571,410 | A | 11/1996 | Swedberg et al. |
| 5,580,523 | A | 12/1996 | Bard |
| 5,670,356 | A | 9/1997 | Sherf et al. |
| 5,750,015 | A | 5/1998 | Soane et al. |
| 5,843,746 | A | 12/1998 | Tatsumi et al. |
| 5,858,195 | A | 1/1999 | Ramsey |
| 5,885,470 | A | 3/1999 | Parce et al. |
| 6,228,604 | B1 | 5/2001 | Escher et al. |
| 6,793,753 | B2 | 9/2004 | Unger et al. |
| 6,949,377 | B2 | 9/2005 | Ho |
| 10,473,665 | B2 | 11/2019 | Trowell et al. |
| 11,385,234 | B2 | 7/2022 | Trowell et al. |
| 2002/0123059 | A1 | 9/2002 | Ho |
| 2003/0049799 | A1 | 3/2003 | Schwartz et al. |
| 2003/0170915 | A1 | 9/2003 | Singh et al. |
| 2005/0079568 | A1 | 4/2005 | Auld |
| 2007/0065818 | A1 | 3/2007 | Foti et al. |
| 2008/0085552 | A1 | 4/2008 | Larson et al. |
| 2010/0129820 | A1 | 5/2010 | Kool et al. |
| 2011/0037077 | A1 | 2/2011 | Ichimura et al. |
| 2011/0071045 | A1 | 3/2011 | Patterson |
| 2012/0064587 | A1 | 3/2012 | Papoutsakis et al. |
| 2012/0077210 | A1 | 3/2012 | Trowell et al. |
| 2014/0001122 | A1 | 1/2014 | Bhattacharyya et al. |
| 2014/0273038 | A1 | 9/2014 | Thompson |
| 2015/0219654 | A1 | 8/2015 | Naleway et al. |
| 2020/0103412 | A1 | 4/2020 | Trowell et al. |
| 2020/0319195 | A1 | 10/2020 | Caron et al. |
| 2021/0018497 | A1 | 1/2021 | Caron et al. |

FOREIGN PATENT DOCUMENTS

| | | | | |
|---|---|---|---|---|
| DE | WO20080083976 | * | 7/2008 | ............ C07K 14/47 |
| EP | 2221606 | | 8/2010 | |
| WO | WO1999049019 | | 9/1999 | |
| WO | WO2000024878 | | 9/1999 | |
| WO | WO2000003727 | | 1/2000 | |
| WO | WO2001001025 | | 1/2001 | |
| WO | WO200146694 | | 6/2001 | |
| WO | WO2001046691 | | 6/2001 | |
| WO | 2002010433 | | 2/2002 | |
| WO | WO2003015923 | | 2/2003 | |
| WO | WO2003035229 | | 5/2003 | |
| WO | WO2006105616 | | 10/2006 | |
| WO | WO2007019634 | | 2/2007 | |
| WO | WO2007033385 | | 3/2007 | |
| WO | WO2007059297 | | 5/2007 | |
| WO | 2007092909 | | 8/2007 | |
| WO | 2008083976 | | 7/2008 | |
| WO | 2008131008 | | 10/2008 | |
| WO | WO2009018467 | | 2/2009 | |
| WO | WO2009020479 | | 2/2009 | |
| WO | 2009052504 | | 4/2009 | |
| WO | WO2009044088 | | 4/2009 | |
| WO | 2010052939 | | 5/2010 | |
| WO | WO2010085844 | | 8/2010 | |
| WO | WO2011091037 | | 7/2011 | |
| WO | WO2012074693 | | 6/2012 | |
| WO | WO2013/155553 | | 10/2013 | |
| WO | WO2014207515 | | 12/2014 | |
| WO | WO2015007317 | | 1/2015 | |
| WO | 2015153151 | | 10/2015 | |
| WO | WO2016131833 | | 8/2016 | |
| WO | WO2017087912 | | 5/2017 | |

OTHER PUBLICATIONS

Walsh et al., Journal of Biotechnology, 1996, 45:235-241.*
Zauner et al., Anal. Chem., 2011, 83: 7356-7363.*
Bajar et al. A Guide to Fluorescent Protein FRET Pairs. Sensors (2016), 16, 1488. (Year: 2016).*
Rauh, V.M. et al., "The determination of plasmin and plasminogen-derived activity in turbid samples from various dairy products using an optimised spectrophotometric method", International Dairy Journal., (2014), 38:74-80.
Wong, M.H-Y. et al., "IncHI2 plasmids are the key vectors responsible for oqxAB transmission among *Salmonella* species", Antimicrobial Agents and Chemotherapy, (2016), 60:6911-6915.
Vavrusova, M. et al., "Characterisation of a whey protein hydrolysate as antioxidant", International Dairy Journal, (2015), 47:86-93.
Wilkins, T.D. et al., "Isolation of recombinant proteins from milk", Journal of Cellular Biochemistry., (1992), 49:333-338.
Rollema, H.S. et al., "On the determination, purification and characterization of the alkaline proteinase from bovine milk", Netherlands Milk and Dairy Journal., (1981), 35:396-399.
Chandrapala, J. et al., "The effect of ultrasound on casein micelle integrity", Journal of Dairy Science., (2012), 95:6882-6890.
Andreani et al., (2016) "Characterisation of the thermostable protease AprX in strains of Pseudomonas fluorescens and impact on the shef-life of dairy products: preliminary results", Italian Journal of Food Safety, 5(6175):239-244.
Starovoitova et al., (2006) "A Comparative Study of Functional Properties of Calf Chymosin and Its Recombinant Forms", Biochemistry, 71(3):320-324.
Majumdar D. S. et al: "Single-molecule FRET reveals sugar-induced conformational dynamics in LacY", Proceedings of the National Academy of Sciences, vol. 104, No. 31, Jul. 31, 2007 (Mar. 31, 2007), pp. 12640-12645.
Hartman Andrea H. et al: "Abstract", Applied and Environmental Microbiology, vol. 77, No. 2, Jan. 15, 2011 (Jan. 15, 2011), pp. 471-478.
18843350.2, Extended European Search Report, dated Jul. 8, 2021, 1-18.
2018315053, Examination Report No. 1, dated Jul. 26, 2021, 1-4.
Bagshaw, Clive R (2001) "ATP analogues at a Glance", J. of Cell Science, 114:459-460.
Benslimane et al., (2009) "Variation with season and lactation of plasmin and plasminogen concentrations in Montbeliard cows' milk", Journal of Dairy Research, 57:423-435.
Button et al, (2011) "Improved Shelf Life Estimation of UHT Milk by Prediction of Proteolysis", Journal of Food Quality, 34:229-235.
Datta and Deeth (2001) "Age Gelation of UHT Milk—A Review", Transactions of the Institution of Chemical Engineers (Part C), 79:197-210.
Dupont et al. (2007) "ELISA To Detect Proteolysis of Ultrahigh-Temperature Milk upon Storage", Journal of Agriculture and Food Chemistry. 55: 6857-6862.
Dupont et al., (1997) "Differential titration of plasmin and plasminogen in milk using sandwich ELISA with monoclonal antibodies", Journal of Dairy Research., 64:77-86.
Eigel, W.N. (1977) "Effect of Bovine Plasmin on $a_s$1-B and K-A Caseins[1]" Journal of dairy science., 60:1399-1403.
Glusman et al. (2001) "The Complete Human Olfactory Subgenome" Genome Res. 11:685-702.
Guarise et al., (2006), "Gold nanoparticles-based protease assay", PNAS, 103:3978-3982.
Jones et al., (1997) "Quenched BODIPY Dye-Labeled Casein Substrates for the Assay of Protease Activity by Direct Fluorescence Measurement", Analytical Biochemistry, 251:144-152.
Kim and Kim (2012) "Analysis of Protease Activity Using Quantum Dots and Resonance Energy Transfer", Theranostics, 2:127-138.
Koka and Weimar (2000) "Isolation and characterization of a protease from Pseudomonas fluorescens RO98", Journal of Applied Microbiology., 89:280-288.
McSweeney et al., (1993) "Proteolytic specificity of plasmin on bovine αs1-Casein", Food Biotechnology., 7:143-158.
Mercier (1973) "Structure primaire de la caseine kB bovine", European Journal of Biochemistry, 35:222-235.

(56) References Cited

OTHER PUBLICATIONS

Saint-Denis et al., (2001) "Enzymatic assays for native plasmin, plasminogen and plasminogen activators in bovine milk", J. Dairy Res., 68:437-449.
Sapsford et al., (2006) "Materials for Fluorescence Resonance Energy Transfer Analysis: Beyond Traditional Donor-Acceptor Combinations**", Angew. Chemie. Int. Ed., 45:4562-4588.
18843350.2, Partial European Search Report, dated Apr. 14, 2021, 1-17.
Berg et al., (2002) "Prokaryotic DNA-binding proteins bind specifically to regulatory sites in operons", Summary—Biochemistry, 1-3, XP55790699.
Brown and Shaw (2008) "Positive Transcription Control: The Glucose Effect", Nature Education, 1-3, XP55790707.
Caron et al., (2018) "Highly sensitive and selective biosensor for a disaccharide based on an AraC-like transcriptional regulator transduced with bioluminescence resonance energy transfer.", Analytical Chemistry, 12986-12993.
Chyan et al., (2017) "Electronic and Steric Optimization of Fluorogenic Probes for Biomolecular Imaging", The Journal of Organic Chemistry, 82:4297-4304.
Chyan W. and Raines R.T., (2018) "Enzyme-Activated Fluorogenic Probes for Live-Cell and in Vivo Imaging", ACS Chemical Biology, 13:1810-1823.
Deuschle et al., (2005) "Construction and optimization of a family of genetically encoded metabolite sensors by semirational protein engineering.", Protein Science, 14:2304-2314.
Extended European Search Report, 18847441.5, dated Apr. 21, 2021, 1-9.
Grimm et al., (2013) "The Chemistry of Small-Molecule Fluorogenic Probes", Progress in Molecular Biology and Translational Science, 113:1-34.
Hakamata et al., (2014) "Multicolor Imaging of Endoplasmic Reticulum-Located Esterase As a Prodrug Activation Enzyme", ACS Medicinal Chemistry Letters, 5:321-325.
Le et al., (2014) "Real-time, continuous detection of maltose using bioluminescence resonance energy transfer (BRET) on a microfluidic system.", Biosensors and Bioelectronics, 62:177-181.
Newman et al., (2019) "Structures of the transcriptional regulator BgaR, a lactose sensor", Acta Cryst, 75(7):639-646.
PCT/AU2018/050824, Written Opinion of the International Preliminary Examining Authority, dated Jul. 3, 2019, 1-8.
Peroza et al., (2015) "A genetically encoded Förster resonance energy transfer sensor for monitoring in vivo trehalose-6-phosphate dynamics", Analytical Biochemistry, 474:1-7.
Salahpour et al., (2012) "BRET biosensors to study GPCR biology, pharmacology, and signal transduction", Frontiers in Endocrinology, 3(105):1-10.
San Martin et al., (2013) "A genetically encoded FRET lactate sensor and its use to detect the Warburg effect in single cancer cells.", PLoS ONE, 8(2):e57712.
San Martin et al., (2014) "Imaging mitochondrial flux in single cells with a FRET sensor for pyruvate.", PLoS ONE, (9)1:e85780.
Wu et al., (2017) "Design and application of a lactulose biosensor.", Scientific Reports, 7(45994):1-8.
Xia Z. and Rao J., (2009) "Biosensing and imaging based on bioluminescence resonance energy transfer", Current Opinion in Biotechnology, 20:37-44.
Yamakawa et al., (2002) "Rapid Homogeneous Immunoassay of Peptides Based on Bioluminescence Resonance Energy Transfer from Firefly Luciferase", Journal of Bioscience and Bioengineering, 93(6):537-542.
Gaucher, et al., (2011) "Proteolysis of casein micelles by Pseudomonas fluorescens CNRZ 798 contributes to the destabilisation of UHT milk during its storage", Dairy Science & Technology, vol. 91, No. 4, pp. 413-429.
Jensen, et al., (2015) "The function of the milk-clotting enzymes bovine and camel chymosin studied by a fluorescence resonance energy transfer Assay[1]", Journal of Dairy Science, vol. 98, No. 5, pp. 2853-2860.
Mateos, et al. (2015) "Proteolysis of mild proteins by AprX, an extracellular protease identified in Pseudomonas LBSA1 isolated from bulk raw milk, and implications for the stability of UHT milk", International Dairy Journal, vol. 49, pp. 78-88.
Aloni et al. (2006) "Ancient genomic architecture for mammalian olfactory receptor clusters" Genome Biol. 7:R88.
Azuma et al., (1992) "Plasmin cleavage of human beta-casein", Biosci Biotechnol Biochem., 56(7)1140-1141.
Buck and Axel Cell (1991) "A novel multigene family may encode odorant receptors: A molecular basis for odor recognition" 65:175-187.
Dacres et al. (2009) "Direct comparison of bioluminescence-based resonance energy transfer methods for monitoring of proteolytic cleavage" Anal. Biochem. 385(2):194-202.
Dacres et al. (2009) "Direct comparison of fluorescence- and bioluminescence-based resonance energy transfer methods for real-time monitoring of thrombin-catalysed proteolytic cleavage" Biosensors and Bioelectronics 24(5):1164-1170.
Dacres et al. (2010) "Experimental Determination of the Förster Distance for Two Commonly Used Bioluminescent Resonance Energy Transfer Pairs" Anal. Chem. 82:432-435.
Dacres et al. (2011) "Greatly enhanced detection of a volatile ligand at femtomolar levels using bioluminescence resonance energy transfer (BRET)" Biosens. and Bioelectron. 29:119-124.
Dacres et al. (2012) "Effect of enhanced Renilla luciferase and fluorescent protein variants on the Förster distance of Bioluminescence resonance energy transfer (BRET)" Biochem. Biophys. Res. Commun. 425(3):625-629.
Day et al. (2004) "Evolution of beetle bioluminescence: the origin of beetle luciferin" Luminescence 19:8-20.
De et al. (2007) "An Improved Bioluminescence Resonance Energy Transfer Strategy for Imaging Intracellular Events in Single Cells and Living Subjects" Cancer Res. 67:7175-7183.
De et al. (2009) "BRET3: a red-shifted bioluminescence resonance energy transfer (BRET)-based integrated platform for imaging protein-protein interactions from single live cells and living animals" FASEB Journal 23(8):2702-2709.
De Wet et al. (1987) "Firefly luciferase gene: structure and expression in mammalian cells" Mol. Cell. Biol. 2987:725-737.
Doty Richard L. (2012) "Gustation" WOREs Cognitive Science 3:29-46.
Esch et al. (2011) "The Role of Body-on-a-Chip Devices in Drug and Toxicity Studies" Annu. Rev. Biomed. Eng. 13:55-72.
Fang et al. (2005) "Determination of Ribonuclease H Surface Enzyme Kinetics by Surface Plasmon Resonance Imaging and Surface Plasmon Fluorescence Spectroscopy" Anal. Chem. 77(20):6528-6534.
Fehr et al. (2002) "Visualization of maltose uptake in living yeast cells by fluorescent nanosensors" PNAS 99(15):9846-9851.
Feldmesser et al. (2006) "Widespread ectopic expression of olfactory receptor genes" BMC Genomics 7:121.
Fredriksson and Schioth (2005) "The Repertoire of G-Protein-Coupled Receptors in Fully Sequenced Genomes" Mol. Pharmacol. 67(5):1414-1425.
Frishman and Argos (1997) "Seventy-Five Percent Accuracy in Protein Secondary Structure Prediction" Proteins 27:329-335.
Fuchs et al. (2001) "The human olfactory subgenome: from sequence to structure and evolution" Human Genetics 108:1-13.
Gill and von Hippel (1989) "Calculation of protein extinction coefficients from amino acid sequence data" Anal. Biochem. 182(2):319-326.
Glusman et al. (2000) "The olfactory receptor gene superfamily: data mining classification and nomenclature" Mammalian Genome 11(11):1016-1023.
Glusman et al. (2000) "Sequence Structure and Evolution of a Complete Human Olfactory Receptor Gene Cluster" Genomics 63(2):227-245.
Godin et al. (2008) "Microfluidics and photonics for Bio-System-on-a-Chip: A review of advancements in technology towards a microfluidic flow cytometry chip" J. Biophotonics 1(5):355-376.
Greer and Szalay (2002) "Imaging of light emission from the expression of luciferases in living cells and organisms: a review" Luminescence 17:43-74.

(56) References Cited

OTHER PUBLICATIONS

Hall et al. (1997) "Two Modes of Ligand Binding in Maltose-binding Protein of *Escherichia coli* Functional Significance In Active Transport" J. Biol. Chem. 272:17615-17622.
Hastings (1996) "Chemistries and colors of bioluminescent reactions: a review" Gene 173:5-11.
Hofmann and Stoffel (1993) "MF C-35 A Database of Membrane Spanning Protein Segments" Biol. Chem. 374:166.
Holden and Cremer (2005) "Microfluidic Tools For Studying The Specific Binding Adsorption And Displacement Of Proteins At Interfaces" Annu. Rev. Phys. Chem. 56:369-387.
Hushpulian et al. (2007) "Biocatalytic properties of recombinant tobacco peroxidase in chemiluminescent reaction" Biotransformation 25:2-4.
Inouye and Shimomura (1997) "The Use of Renilla Luciferase Oplophorus Luciferase and Apoaequorin as Bioluminescent Reporter Protein in the Presence of Coelenterazine Analogues as Substrate" Biochem. J. 233(2):349-353.
Ismail et al., (2010) "Invited review: Plasmin protease in milk: current knowledge and relevance to dairy industry.", J Dairy Sci., 93(11)4999-5009.
Klein et al. (1984) "Prediction of protein function from sequence properties: Discriminant analysis of a data base" Biochim. Biophys. Acta 787(3):221-226.
Kocan et al (2008) "Demonstration of Improvements to the Bioluminescence Resonance Energy Transfer (BRET) Technology for the Monitoring of G Protein-Coupled Receptors in Live Cells" Journal of Biomolecular Screening 13(9):888-898.
Kocan et al (2011) "Enhanced BRET technology for the monitoring of agonist-induced and agonist-independent interactions between GPCRs and β-arrestins" Frontiers in Endocrinology Cellular Endocrinology 1(12):1-9.
Lander et al. (2001) "Initial sequencing and analysis of the human genome" Nature 409:860-921.
Li and Lin (2008) "Applications of microfluidic systems in environmental analysis" Anal Bioanl. Chem. 393(2):555-567.
Loening et al. (2006) "Consensus guided mutagenesis of Renilla luciferase yields enhanced stability and light output" Protein Eng. Des. Sel. 19(9):391-400.
Loening et al. (2007) "Red-shifted Renilla reniformis luciferase variants for imaging in living subjects." Nature Methods 4(8):641-643.
Lorenz et al. (1991) "Isolation and expression of a cDNA encoding Renilla reniformis luciferase." Proc. Natl. Acad. Sci. USA 88(10):4438-4442.
Mark et al. (2010) "Microfluidic lab-on-a-chip platforms: requirements characteristics and applications" Chem. Soc. Rev. 39:1153-1182.
Medintz and Deschamps (2006) "Maltose-binding protein: a versatile platform for prototyping biosensing" Curr. Opin. Biotech. 17:17-27.
Mohammed and Desmulliez (2011) "Lab-on-a-chip based immunosensor principles and technologies for the detection of cardiac biomarkers: a review" Lab. Chip. 11:569-595.
Morin and Hastings (1971) "Energy transfer in a bioluminescent system" J. Cell. Physiol. 77(3):313-318.
Niimura and Nei (2003) "Evolution of olfactory receptor genes in the human genome" Proc. Natl. Acad. Sci. USA. 100(21):12235-12240.
Noh et al. (2011) "Biosensors in Microfluidic Chips" Top. Curr. Chem. 304:117-152.
Olender et al. (2004) "The olfactory receptor universe—from whole genome analysis to structure and evolution" Genet. Mol. Res. 3(4):545-553.
Olender et al. (2004) "The canine olfactory subgenome" Genomics. 83(3):361-372.
Park et al. (2009) "Detection of conformationally changed MBP using intramolecular FRET" Biochem. Biophys. Res. Commun. 388(3):560-564.
Persson and Argos (1994) "Prediction of Transmembrane Segments in Proteins Utilising Multiple Sequence Alignments" J. Mol. Biol. 237(2):182-192.
Pfleger and Eidne (2006) "Illuminating insights into protein-protein interactions using bioluminescence resonance energy transfer (BRET)" Nature Methods 3:165-174.
Pilpel and Lancet (1999) "The variable and conserved interfaces of modeled olfactory receptor proteins" Protein Science 8(5):969-977.
Remedios and Moens (1995) "Fluorescence Resonance Energy Transfer Spectroscopy Is a Reliable "Ruler" for Measuring Structural Changes in Proteins: Dispelling the Problem of the Unknown Orientation Factor" J. Structural Biol. 115(2):175-185.
Robertson (1998) "Two Large Families of Chemoreceptor Genes in the Nematodes *Caenorhabditis elegans* and *Caenorhabditis briggsae* Reveal Extensive Gene Duplication Diversification Movement and Intron Loss" Genome Research 8:449-463.
Robertson (2001) "Updating the str and srj (stl) Families of Chemoreceptors in *Caenorhabditis* Nematodes Reveals Frequent Gene Movement Within and Between Chromosomes" Chem Senses 26(2):151-159.
Sengupta et al. (1996) "odr-10 Encodes a Seven Transmembrane Domain Olfactory Receptor Required for Responses to the Odorant Diacetyl" Cell 84(6):899-909.
Sharff et al. (1992) "Crystallographic evidence of a large ligand-induced hinge-twist motion between the two domains of the maltodextrin binding protein involved in active transport and chemotaxis" Biochemistry 31(44):10657-10663.
Sharff et al. (1993) "Refined 1.8-.ANG. structure reveals the mode of binding of .beta.-cyclodextrin to the maltodextrin binding protein" Biochemistry 32(40):10553-10559.
Sharon et al. (1998) "Genome Dynamics Evolution and Protein Modeling in the Olfactory Receptor Gene Superfamily" Ann. N Y Acad. Sci. 855:182-193.
Spurlino et al. (1991) "The 2.3-A resolution structure of the maltose- or maltodextrin-binding protein a primary receptor of bacterial active transport and chemotaxis." J. Biol. Chem. 266: 5202-5219.
Sun and Zhu, (2000) "Receptor-mediated endocytosis of uPA and its inhibitor complex and its application", Chemistry of Life, 20(4):151-153.
Theberge et al. (2010) "Microdroplets in Microfluidics: An Evolving Platform for Discoveries in Chemistry and Biology" Angew. Chem Int. Ed 49(34):5846-5868.
Tsien (1998) "The Green Fluorescent Protein" Ann. Rev. Biochem. 67:509-544.
Unger et al. (2000) "Monolithic Microfabricated Valves and Pumps by Multilayer Soft Lithography" Science 288(5463):113-116.
Verhaegen and Christopoulos (2002) "Recombinant Gaussia Luciferase. Overexpression Purification and Analytical Application of a Bioluminescent Reporter for DNA Hybridization" Anal. Chem. 74(17):4378-4385.
Viviani (2002) "The origin diversity and structure function relationships of insect luciferases" Cell. Mol. Life Sci. 59(11):1833-1850.
Von Heijne (1992) "Membrane protein structure prediction : Hydrophobicity analysis and the positive-inside rule" J. Mol. Biol. 225(2):487-494.
Xu et al. (1999) "A bioluminescence resonance energy transfer (BRET) system: Application to interacting circadian clock proteins" Proc. Natl. Acad. Sci. USA. 96:151-156.
Yeo et al. (2011) "Microfluidic Devices for Bioapplications" Small 7:12-48.
Young et al. (2002) "Different evolutionary processes shaped the mouse and human olfactory receptor gene families" J. Human Mol. Genet. 11(5):535-546.
Zhang and Firestein (2002) "The olfactory receptor gene superfamily of the mouse" Nat. Neurosci. 5:124-133.
Zozulya et al. (2001) "The human olfactory receptor repertoire" Genome Biol. 2(6):0018.1-0018.12.
Bajar et al., (2016) "A guide to fluorescent protection FRET pairs", Sensors, vol. 16, No. 1488, pp. 1-24.
Dacres et al., (2012) "Comparison of enhanced bioluminescence energy transfer donors for protease biosensors", Analytical Biochemistry, vol. 424, pp. 206-210.

(56) References Cited

OTHER PUBLICATIONS

Martins et al., (2015) "Milk-deteriorating exoenzymes from Pseudomonas fluorescens 041 isolated from refrigerated raw milk", Brazilian Journal of Microbiology, vol. 46, No. 1, pp. 207-217.

Zhang and Lv, (2014) "Purification and properties of heat-stable extracellular protease from pseudomonas fluorescens BJ-10", J. Food Sci Technol, vol. 51, No. 6, pp. 1185-1190.

Jensen et al. "The function of the milk-clotting enzymes bovine and camel chymosin studied by a fluorescence resonance energy transfer assay", Journal of Dairy Science, vol. 98, Issue 5, 2015, pp. 2853-2860, ISSN 0022-0302.†

Gaucher, Tanguy, Fauquant, Jardin, Rousseau, et al., "Proteolysis of casein micelles by Pseudomonas fluorescens CNRZ 798 contributes to the destabilisation of UHT milk during its storage." Dairy Science & Technology, EDP sciences/Springer, 2011, 91 (4), pp. 413-429. 10.1007/s13594-011-0019-4. hal-00930578.†

\* cited by examiner
† cited by third party (A) 40 kHz, 5 W, 16 μm (B) 40 kHz, 8 W, 19 μm

PROTEASE SENSOR MOLECULES

CROSS-REFERENCE TO RELATED APPLICATIONS

This application is a national stage filing under 35 U.S.C. § 371 of PCT/AU2017/051237, filed Nov. 13, 2017, which claims the benefit of Australian Patent Application No. 2017900161, filed Jan. 19, 2017 and Australian Patent Application No. 2016904639, filed Nov. 14, 2016 which applications are incorporated herein by reference in their entirety.

FIELD OF THE INVENTION

The present invention relates to sensors and methods for detecting bacterial proteases in a sample. In particular, the present invention relates to sensors and methods for detecting *Pseudomonas* spp. protease activity in a sample. The sensors and methods may be used to detect or predict spoilage of a dairy product.

BACKGROUND OF THE INVENTION

Milk is prone to rapid spoilage. Spoilage can occur as a result of both intrinsic factors, for example enzymes that are naturally present in milk (such as plasmin), and extrinsic factors, such as enzymes that are produced by microorganisms present in the milk. The most common and abundant spoilage microorganisms present in properly stored refrigerated milk are *Pseudomonas* species, which are classed as psychrotrophs and have a selective advantage in cold conditions. Psychrotropic bacteria have the ability to multiply relatively quickly at low storage temperatures, for example 4° C. Bacterial growth is accompanied by the production and secretion of enzymes, including proteases, into the surrounding medium when the population density of a culture of *Pseudomonas* exceeds ~$10^6$ cfu/ml. These proteases are aggressive and relatively heat-stable. They are able to degrade milk proteins, such as casein, which may lead to increased viscosity, gelation, and bitterness in whole and skimmed UHT milk during storage, thereby leading to loss of shelf-life. While techniques such as pasteurisation and ultra-high-temperature (UHT) processing can help prevent spoilage and extend the shelf life of milk, some bacterial enzymes are resistant to heat treatment. If sufficient enzymes are produced by the bacteria prior to heat treatment, UHT milk can spoil even after it is been treated. Of these enzymes, proteases are of particular importance because they can cause milk spoilage when present at very low concentrations. Furthermore, proteases in milk may also adversely affect the yield, quality and/or shelf life of a range of other dairy products including flavoured, modified and fortified milks, powdered milk and powdered products made from milk, including infant formula, cheeses and ultralong life pasteurised milk.

A range of methods have been used to measure bacterial proteases in dairy products such as milk. The most commonly used methods for detecting bacterial proteases in milk samples, such as fluorescein isothiocyanate (FITC) casein protease assay, require extensive manipulation. They are either not sensitive enough to detect the very low levels of protease that can result in spoilage of UHT milk between 6-9 months after production or are incapable of detecting them at all (Button et al., (2011)). In addition, these methods are generally slow, delivering results in a matter of days to weeks. Therefore, while they may be used for post hoc determination of the cause of a product failure they are of little use for real time management of the production, processing and distribution of dairy products.

Two methods which distinguish *Pseudomonas* spp. protease in milk from plasmin, namely HPLC and a competition ELISA assay, have been reported (Datta and Deeth, 2001; Dupont et al., 2007; Martins, 2015). Both of these methods require extended incubations of several hours to days during which time the proteases deplete endogenous κ-casein releasing specific peptides into the supernatant. The HPLC based method uses differential acid precipitation followed by reverse phase separation to identify the characteristic κ-casein-derived peptides (Datta and Deeth, 2001). The ELISA method relies on a monoclonal antibody specific for the intact $Met_{105}$-$Phe_{106}$ target of Pflu proteases to measure the residual intact kappa-casein (κ-casein) in a sample (Dupont et al., 2007). Undigested κ-casein in the assay competes with a fixed amount of purified κ-casein on the wall of the ELISA plate. These methods are not suitable for measuring *Pseudomonas* spp. protease activity prior to milk spoilage.

Therefore, there is a need for sensors and methods that can be used for detecting bacterial proteases in a sample, particularly methods that can be performed rapidly and/or with increased sensitivity. There is also a need for methods which discriminate between spoilage due to intrinsic factors such as plasmin and extrinsic factors such as the bacterial proteases.

SUMMARY OF THE INVENTION

The present inventors have identified sensors that can be used to detect bacterial protease in a sample. The present inventors have also identified an improved method of detecting the presence of bacterial protease in a sample using these sensors. They have also identified an improved method of detecting spoilage of a dairy product using these sensors.

In one aspect, there is provided a *Pseudomonas* spp. protease sensor molecule comprising a target sequence having at least one *Pseudomonas* spp. protease cleavage site selected from the group consisting of KQ, SF, FM, KK, KN, NQ, NT, EI, QQ and combinations thereof, and one or more of the following features:
  (i) the target sequence is less than about 50 amino acids in length;
  (ii) a detectable label; and/or
  (iii) two or more of the protease cleavage sites;
wherein cleavage of the target sequence by a *Pseudomonas* spp. protease produces a detectable change.

In some embodiments, there is provided a *Pseudomonas* spp. protease sensor molecule comprising a target sequence having at least one *Pseudomonas* spp. protease cleavage site selected from the group consisting of KQ, SF, FM, KK, KN, NQ, NT, EI and combinations thereof, and one or more of the following features:
  (i) the target sequence is less than about 50 amino acids in length;
  (ii) a detectable label; and/or
  (iii) two or more of the protease cleavage sites;
wherein cleavage of the target sequence by a *Pseudomonas* spp. protease produces a detectable change.

In some embodiments, the target sequence comprises two or more of the protease cleavage sites. In some embodiments, the target sequence comprises three, four, five, six or seven protease cleavage sites.

In some embodiments, the target sequence comprises a *Pseudomonas* spp. protease cleavage site selected from the group consisting of KQ, SFM (SEQ ID NO: 37), KKNQ (SEQ ID NO: 24), NT and EI and combinations thereof. In some embodiments, the target sequence at least comprises SFM (SEQ ID NO: 37) and/or KKNQ (SEQ ID NO: 24). In further embodiments, the target sequence comprises SKMXXPP (SEQ ID NO: 40), where X is any amino acid. In some embodiments, the target sequence comprises an amino acid sequence selected from: SFMKKNQNTEI (SEQ ID NO: 45); SFMNQNTEI (SEQ ID NO: 57); and LSF-MAIP (SEQ ID NO: 70). In further embodiments, the target sequence comprises an amino acid sequence selected from: LQGSFMKKNQNTEIGSFE (SEQ ID NO: 72); LQGSFMNQNTEIGSFE (SEQ ID NO: 73); LQGSLSF-MAIPGSFE (SEQ ID NO: 74) and LQG-SKQKQKQKQGSFE (SEQ ID NO: 112). Other examples include LQGSPPLKQPPPGSFE (SEQ ID NO:113), LQGSPPLQQPQPGSFE (SEQ ID NO:114) and LQGGSGGSLKQQGGSGGSFE (SEQ ID NO:115).

In some embodiments, the target sequence comprises an amino acid linker at the N- and/or C-terminus which is attached to a detectable label. In some embodiments, the linker comprises one or more glycine, serine and/or proline residues. For example, in some embodiments the linker comprises an amino acid sequence selected from: LQG (SEQ ID NO: 95); GSFE (SEQ ID NO: 96); GSSGGS (SEQ ID NO: 97); GSPPL (SEQ ID NO: 98); PPPGS (SEQ ID NO: 99), GGSGGS (SEQ ID NO: 100, GGSGGSL (SEQ ID NO: 101) and PPVKQPPP (SEQ ID NO: 44).

Cleavage of the target sequence by a *Pseudomonas* spp. protease results in a detectable change. In some embodiments, the detectable change is a change in resonance energy transfer, acoustics, electrochemical potential, fluorescence, chemiluminescence, phosphorescence, absorbance, antibody binding, BRET ratio, FRET efficiency or mass. In a some embodiments, cleavage of the target sequence by a *Pseudomonas* spp. protease results in a detectable change in resonance energy transfer (RET).

In some preferred embodiments, the sensor molecule comprises a detectable label. Preferably, the detectable label is selected from the group consisting of a chromophore, a nanoparticle, a quantum dot, a viologen and combinations thereof.

In some embodiments, the detectable label is a chromophore. In a preferred embodiment, the chromophore is selected from the group consisting of fluorophores, luminophores, organic dyes, inorganic dyes, phosphophores, light absorbing nanoparticles, combinations thereof, and the metalated complexes thereof.

In some embodiments, the detectable label comprises two or more components. For example, the detectable label may comprise two components. In some embodiments, the detectable label comprises: i) a chemiluminescent donor domain and an acceptor domain covalently attached to the target sequence, or ii) a fluorophore domain and a acceptor domain. In some embodiments, one domain is covalently attached to the N-terminus of the target sequence and the other domain is covalently attached to the C-terminus of the target sequence. For example, the chemiluminescent donor domain may be covalently attached to the N-terminus of the target sequence and the acceptor domain may be covalently attached to the C-terminus of the target sequence. Alternatively, the acceptor domain may be covalently attached to the N-terminus of the target sequence and the chemiluminescent donor domain may be covalently attached to the C-terminus of the target sequence.

In some preferred embodiments, the detectable label comprises a chemiluminescent donor domain and an acceptor domain covalently attached to the target sequence. In some embodiments, the spatial location and/or dipole orientation of the chemiluminescent donor domain relative to the acceptor domain is altered when the target sequence is cleaved by a *Pseudomonas* spp. protease. The alteration in the spatial location and/or dipole orientation of the chemiluminescent donor domain relative to the acceptor domain can produce a detectable change.

In some embodiments, cleavage of the target sequence by a *Pseudomonas* spp. protease results in a change in BRET ratio. In some embodiments, the change in BRET ratio is between about 2% to about 95% of the maximum observed BRET ratio. In some embodiments, the change in BRET ratio is between about 5% to about 90% of the maximum observed BRET ratio.

In some embodiments, the chemiluminescent donor domain is a bioluminescent protein. In some embodiments, the bioluminescent protein is selected from the group consisting of a luciferase, a β-galactosidase, a lactamase, a horseradish peroxidase, an alkaline phosphatase, a β-glucuronidase or a β-glucosidase.

In some embodiments, the bioluminescent protein is a luciferase. In some embodiments, the luciferase is selected from the group consisting of *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, an *Arachnocampa* luciferase, or a biologically active variant or fragment of any one, or chimera of two or more, thereof.

In some embodiments, the bioluminescent protein has a substrate selected from luciferin, calcium, coelenterazine, a derivative or analogue of coelenterazine or an derivative or analogue of luciferin.

In some embodiments, the bioluminescent protein requires a co-factor. For example, the co-factor may be ATP, magnesium, oxygen, FMNH2, calcium, or a combination of any two or more thereof.

In some embodiments, the acceptor domain is a fluorescent acceptor domain. In some embodiments, the fluorescent acceptor domain is a protein. In some embodiments, the fluorescent acceptor domain is selected from the group consisting of green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pociloporin, *Renilla* GFP, Monster GFP, paGFP, Kaede protein, tdTomato, mCherry, TagRFP, TurBoFB and a Phycobiliprotein, and a biologically active variant or fragment of any one thereof.

Alternatively, the fluorescent acceptor domain is a non-protein. In some embodiments, the fluorescent acceptor domain is selected from the group consisting of Alexa Fluor dye, Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red and rare earth element chelates, and any combination or derivatives thereof.

In some embodiments, the acceptor domain is selected from the group consisting of green fluorescent protein (GFP), Venus and mOrange, and a biologically active variant or fragment of any one thereof; the chemiluminescent donor domain is a luciferase or a biologically active variant or fragment; and the target sequence comprises SFMK-KNQNTEI (SEQ ID NO: 45), SFMNQNTEI (SEQ ID NO: 57), or LSFMAIP (SEQ ID NO: 70).

In some embodiments, i) the acceptor domain is GFP$^2$, the chemiluminescent donor domain is a *Renilla* luciferase, and the target sequence comprises SFMKKNQNTEI (SEQ ID NO: 45), ii) the acceptor domain is GFP$^2$, the chemiluminescent donor domain is a *Renilla* luciferase 2, and the target sequence comprises SFMKKNQNTEI (SEQ ID NO: 45), iii) the acceptor domain is GFP$^2$, the chemiluminescent donor domain is a *Renilla* luciferase 8, and the target sequence comprises SFMKKNQNTEI (SEQ ID NO: 45), or iv) the acceptor domain is mOrange, the chemiluminescent donor domain is a *Renilla* luciferase 8.6-535, and the target sequence comprises SFMKKNQNTEI (SEQ ID NO: 45).

In some embodiments, i) the acceptor domain is GFP$^2$, the chemiluminescent donor domain is a *Renilla* luciferase, and the target sequence comprises SFMNQNTEI (SEQ ID NO: 57), ii) the acceptor domain is GFP$^2$, the chemiluminescent donor domain is a *Renilla* luciferase 2, and the target sequence comprises SFMNQNTEI (SEQ ID NO: 57), iii) the acceptor domain is GFP$^2$, the chemiluminescent donor domain is a *Renilla* luciferase 8, and the target sequence comprises SFMNQNTEI (SEQ ID NO: 57), or iv) the acceptor domain is mOrange, the chemiluminescent donor domain is *Renilla* luciferase 8.6-535, and the target sequence comprises SFMNQNTEI (SEQ ID NO: 57).

In some embodiments, i) the acceptor domain is GFP$^2$, the chemiluminescent donor domain is a *Renilla* luciferase, and the target sequence comprises LSFMAIP (SEQ ID NO: 70), ii) the acceptor domain is GFP$^2$, the chemiluminescent donor domain is a *Renilla* luciferase 2, and the target sequence comprises LSFMAIP (SEQ ID NO: 70), iii) the acceptor domain is GFP$^2$, the chemiluminescent donor domain is a *Renilla* luciferase 8, and the target sequence comprises LSFMAIP (SEQ ID NO: 70), or iv) the acceptor domain is mOrange, the chemiluminescent donor domain is a *Renilla* luciferase 8.6-535, and the target sequence comprises LSFMAIP (SEQ ID NO: 70).

As the skilled person would understand, the $EC_{50}$ and sensitivity of a sensor can vary depending on the detection method used. In one embodiment, sensor cleavage is detected using a method as defined in Examples 2 and 10. In this embodiment, in an example the sensor has an $EC_{50}$ of between 0.1 and 10 nM for a *Pseudomonas* spp. protease, and/or the sensor is at least 100 times more sensitive for a *Pseudomonas* spp. protease compared to bovine plasmin. In an alternate embodiment, sensor cleavage is detected using a method such as defined in Example 12. In this embodiment, in an example the sensor has an $EC_{50}$ of between 0.1 and 100 nM for a *Pseudomonas* spp. protease, and/or the sensor is at least 20 times more sensitive for a *Pseudomonas* spp. protease compared to bovine plasmin.

In some embodiments, the *Pseudomonas* spp. is *Pseudomonas fluorescens, Pseudomonas fragi, Pseudomonas ludensis, Pseudomonas putida, Pseudomonas* LBSA1 or *Pseudomonas aureofaciens*.

In some embodiments, the sensor is a continuous stretch of amino acids.

In another aspect, the present invention provides an isolated nucleic acid encoding the sensor as described herein, or a target sequence thereof.

In yet another aspect, the present invention also provides a vector comprising an isolated nucleic acid encoding the sensor as described herein, or a target sequence thereof.

In yet another aspect, the present invention also provides a host cell comprising a vector comprising the nucleic acid encoding the sensor as described herein, or a target sequence thereof or the nucleic acid encoding the sensor as described herein, or a target sequence thereof, wherein the nucleic acid is operably linked to a promoter capable of expressing the sensor, or target sequence thereof, in the cell.

In yet another aspect, the present invention also provides use of the sensor as described herein to detect a *Pseudomonas* spp. protease in a sample.

In yet another aspect, the present invention also provides use of the sensor as described herein to detect spoilage of a dairy product.

In yet another aspect, the present invention also provides use of the sensor as described herein to detect a *Pseudomonas* spp. infection.

In yet another aspect, the present invention also provides a method of detecting a *Pseudomonas* spp. protease in a sample, the method comprising
  i) contacting a sample with the sensor as described herein; and
  ii) detecting a change in the sensor, wherein said change corresponds to the presence of a *Pseudomonas* spp. protease in the sample.

In some embodiments, the sample is selected from the group consisting of a dairy product or an extract thereof, soil or an extract thereof, clinical samples or an extract thereof, samples from medical equipment, samples from food processing equipment and plant material or an extract thereof. In some embodiments, the clinical sample, includes but is not limited to blood, serum, sputum, mucus, pus, peritoneal fluid and other bodily fluids. In some embodiments, medical equipment includes, but is not limited to, catheters, intravenous lines, ventilators, dialysis equipment and the like. In some embodiments, food processing equipment includes, but is not limited to, transport tankers, holding tanks, processing machinery, lines, connectors, valves and the like.

In yet another aspect, the present invention also provides a method of detecting spoilage of a dairy product, the method comprising
  i) contacting a sample with the sensor as described herein; and
  ii) detecting a change in the sensor, wherein said change indicates that the dairy product is spoilt, has begun to spoil or has the potential to spoil.

In some embodiments, dairy product is selected from the group consisting of raw milk, low fat milk, skim milk, pasteurized milk, UHT milk, lactose-modified UHT milk, fortified UHT milk, flavoured UHT milk, and combinations of these products as well as UHT infant formula, cheese, yoghurt, whey, buttermilk, cream, milk powder, powdered infant formula and butter.

In some embodiments, the detectable change is a change in resonance energy transfer, acoustics, electrochemical potential, fluorescence, phosphorescence, absorbance, antibody binding, BRET ratio, FRET efficiency or mass.

In some embodiments, the sensor comprises a chemiluminescent donor domain and the method further comprises providing a substrate for the chemiluminescent donor domain. In some embodiments, the substrate is luciferin, calcium, coelenterazine, a derivative or analogue of coelenterazine, or a derivative or analogue of luciferin.

In some embodiments, the method further comprises providing a co-factor of the chemiluminescent donor domain. In some embodiments, the co-factor is ATP, magnesium, oxygen, $FMNH_2$, calcium, or a combination of any two or more thereof.

In some embodiments, the method is capable of detecting at least 10 pM of *Pseudomonas* spp. protease. In some embodiments, the method is capable of detecting at least 1 pM of *Pseudomonas* spp. protease. In another embodiment, the method is capable of detecting at least 100 pM of *Pseudomonas* spp. protease.

In some embodiments, the method is performed in less than 1 hour, less than 30 minutes or less than 15 minutes.

In another aspect, the present invention provides a composition comprising the sensor as described herein, and one or more acceptable carrier(s).

In another aspect, the present invention provides a kit comprising the sensor as described herein.

The present inventors have found that sonicating the composition in the presence of a compound which competes with the protease binding casein reduces the amount of time required for sample preparation. Samples prepared using this method can be used in the methods and/or uses of the present application.

Thus, in another aspect, the present invention also provides a method of dissociating protease from a casein micelle, the method comprising sonicating a composition comprising protease associated with casein micelle in the presence of a compound which competes with the protease binding casein.

In some embodiments, the present invention also provides a method of dissociating protease from a casein micelle, the method comprising sonicating a composition comprising protease associated with casein micelle in the presence of a compound which competes with the protease binding casein and a calcium chelating agent.

In some embodiments, the composition comprising protease associated with casein micelle is a sample of a dairy product or extract thereof comprising a protease bound to casein.

Preferably, the protease causes, at least in part, milk spoilage. In some embodiments the protease is plasmin. In some embodiments, the protease is a bacterial protease. In some embodiments, the bacterial protease is produced by a *Pseudomonas* spp. In some embodiments, the *Pseudomonas* spp. is *Pseudomonas fluorescens*, *Pseudomonas fragi*, *Pseudomonas ludensis*, *Pseudomonas putida*, *Pseudomonas* LBSA1 or *Pseudomonas aureofaciens*.

In some embodiments, the compound which competes with the protease binding casein is a derivative or analogue of lysine. In preferred embodiments, the derivative or analogue of lysine is aminocaproic acid.

In some embodiments, the calcium chelating agent is selected from the group consisting of sodium hexametaphosphate, disodium hydrogen phosphate, trisodium citrate, sodium phytate, ethylenediaminetetraacetic acid and ethylene glycol-bis($\beta$-aminoethyl ether)-N,N,N',N'-tetraacetic acid. In preferred embodiments, the calcium chelating agent is trisodium citrate.

In some embodiments, the sonicating is carried out for 15 minutes or less, 10 minutes or less, 5 minutes or less, or 2 minutes or less. In some embodiments, the sonicating is carried out with sonication device displacement amplitude of between about 10 µm and about 300 µm or about 15 µm and about 300 µm, preferably between about 15 µm and about 25 µm.

In some embodiments, the sonicating is carried out with a probe diameter of between about 11 mm to about 2 mm.

In some embodiments, the sonicating is carried out at a frequency of between about 10 kHz and about 60 kHz, preferably between about 28 kHz and about 40 kHz.

In some embodiments, the sonicating is carried out at a power of less than about 55 watts, preferably less than about 25 watts and most preferably between about 5 watts and about 8 watts. In some embodiments, when the sample is less than about 1 ml volume, sonicating is carried out with the acoustic power level of less than about 1 watt.

In some embodiments, the sonicating is carried out a temperature less than about 50° C., preferably less than about 40° C., and most preferably less than about 30° C.

In yet another aspect, the present invention provides a method of determining the concentration of protease in a dairy product, the method comprising
  (i) processing a sample of the dairy product using the sonication method described herein;
  (ii) measuring protease activity in the processed dairy product; and
  (iii) determining the concentration of protease of the dairy product based on the protease activity.

In some embodiments, the dairy product is selected from the group consisting of raw milk, low fat milk, skim milk, pasteurized milk, UHT milk, lactose-modified UHT milk, fortified UHT milk, flavoured UHT milk, UHT infant formula, cheese, yoghurt, whey, buttermilk, cream, milk powder, powdered infant formula and butter and combinations thereof, and/or an extract of one or more thereof comprising a protease bound to casein.

In some embodiments, step (ii) comprises mixing the processed dairy product with a sensor molecule comprising a target sequence having at least one protease cleavage site and optionally a detectable label, wherein cleavage of the target sequence by the protease produces a detectable change; and measuring the detectable change.

In an embodiment, the sensor molecule is a sensor molecule of the invention.

In some embodiments, the sensor molecule is a *Pseudomonas* spp. protease sensor molecule as described herein. In some embodiments, the sensor molecule comprises a detectable label and the detectable label comprises a chemiluminescent donor domain and an acceptor domain covalently attached to the target sequence.

In some embodiments, the protease has a cleavage site selected from the group consisting of SF, FM, NQ, NT, EI, QQ, or KZ where Z is Q, N, K, Y, V or E, and combinations thereof.

In some embodiments, the protease has a cleavage site selected from the group consisting of SF, FM, NQ, NT, EI or KZ where Z is Q, N, K, Y, V or E, and combinations thereof.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying.

BRIEF DESCRIPTION OF THE ACCOMPANYING DRAWINGS

FIG. 1—BRET$^2$ sensor for detecting bacterial protease activity according to one embodiment. The sensor incorporates a Phe-Met cleavage site.

Figure 2:
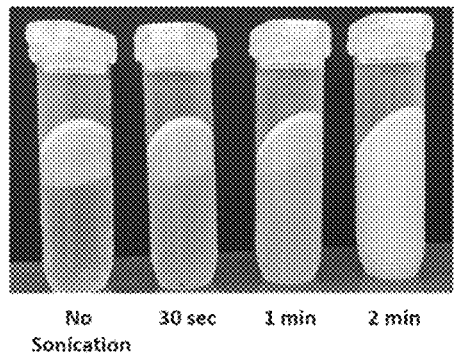
Figure 2:
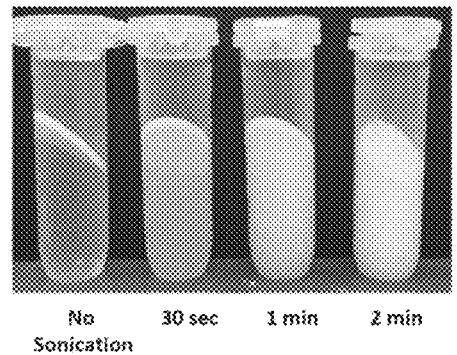

FIG. 2—Pre-treatment of raw milk according to embodiments of the present disclosure. (A) A 1.5 mL sample was sonicated using the Honda ZO41 ultrasonic cutter modified to have a probe tip diameter of 4 mm, frequency=40 kHz, amplitude=16 µm and power consumption=5 W for 0 s, 30 s, 1 min and 2 min; and (B) A 1.5 mL sample is sonicated using the Honda ZO41 ultrasonic cutter modified to have a probe tip diameter of 4 mm, frequency=40 kHz, amplitude=19 µm and power consumption=8 W for 0 s, 30 s, 1 min and 2 min. Following sonication all samples were centrifuged for 2 minutes at approximately 12,000 g in order to determine how effective the sonication step had been in homogenising the sample.

Figure 3:
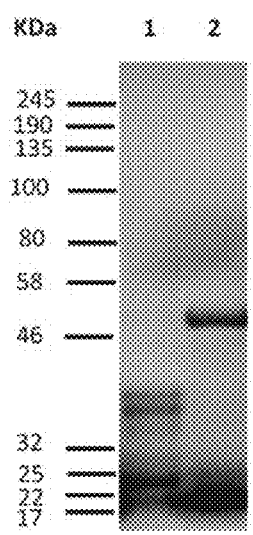

FIG. 3—SDS-PAGE of crude extract prepared from skimmed milk incubated with *P. fluorescens* strain 65 (lane 2) or control (lane 1).

Figure 4:
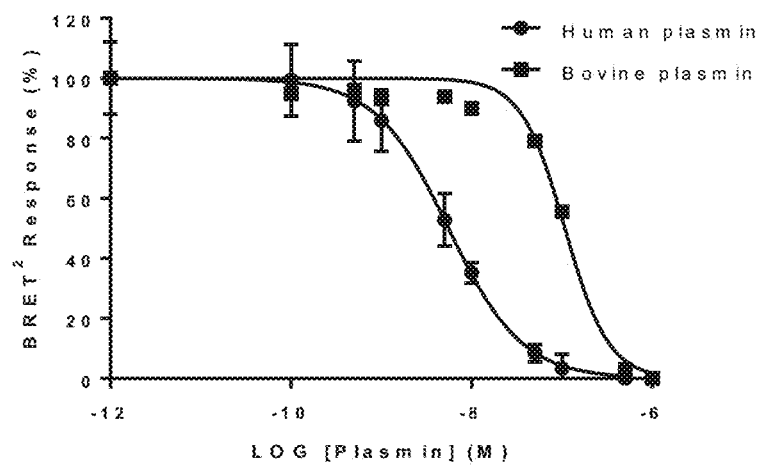

FIG. 4—BRET$^2$ response of plasmin sensor after incubation of the sensor with various concentrations of human plasmin and bovine plasmin for 10 minutes.

Figure 5:
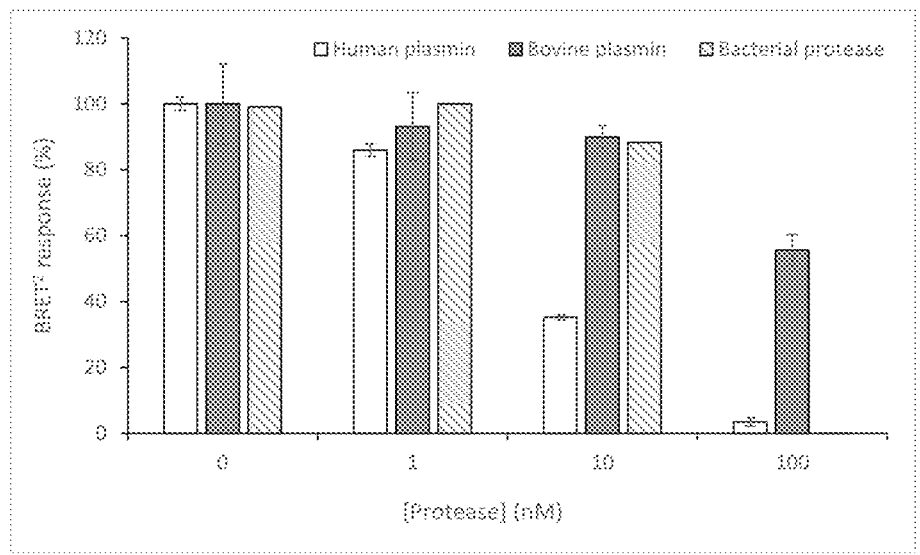

FIG. 5—BRET$^2$ response of plasmin sensor after incubation of the sensor with 0, 1, 10 and 100 nM of human plasmin, bovine plasmin and crude bacterial protease for 10 minutes.

Figure 6:
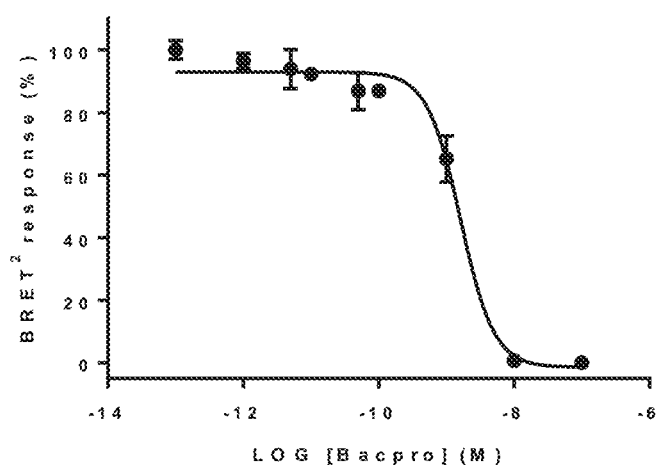

FIG. 6—Calibration of bacterial protease using the Plasmin sensor in raw milk following 10 minute incubation at 28° C.

Figure 7:
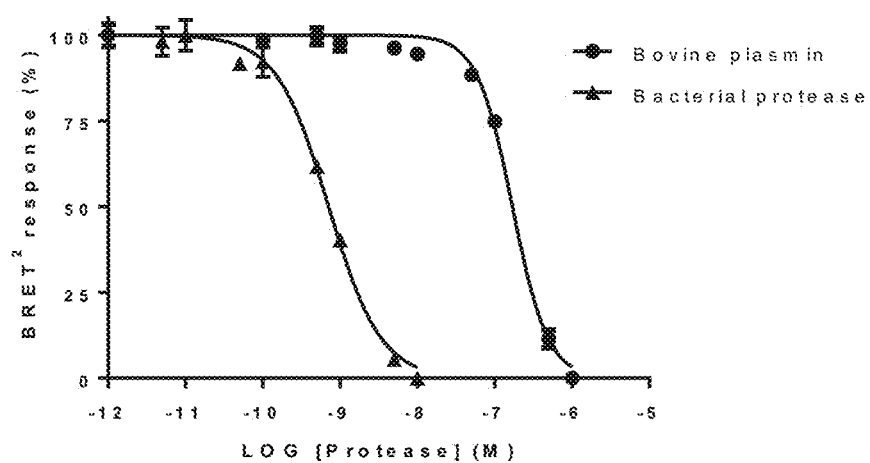

FIG. 7—BRET$^2$ response of Pflu sensor 1 after incubation of the sensor with various concentrations of bovine plasmin and crude bacterial protease in 50% full fat UHT milk for 10 minutes.

Figure 8:
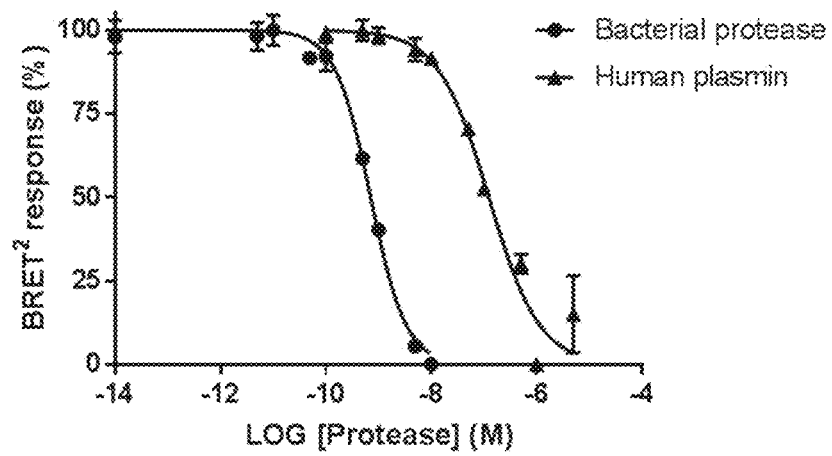

FIG. 8—BRET$^2$ response of Pflu sensor 1 after incubation of the sensor with various concentrations of human plasmin and crude bacterial protease in 50% full fat UHT milk for 10 minutes.

Figure 9:
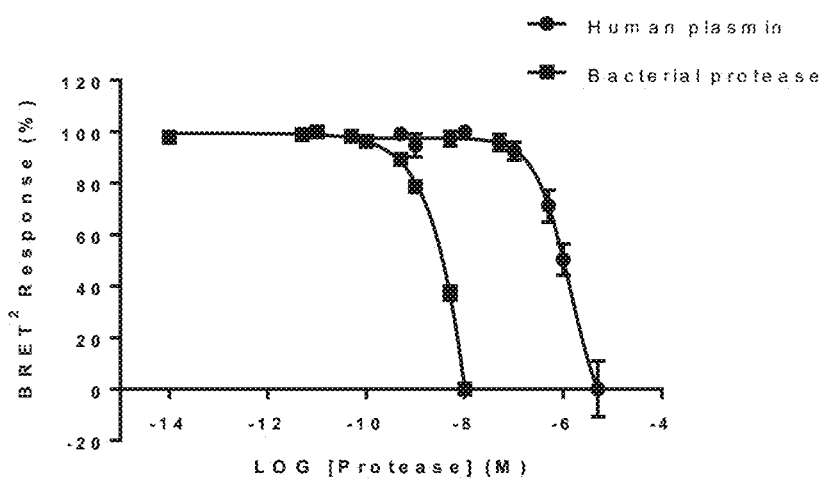

FIG. 9—BRET$^2$ response of Pflu sensor 2 after incubation of the sensor with various concentrations of human plasmin and crude bacterial protease in 50% full fat UHT milk for 10 minutes.

Figure 10:
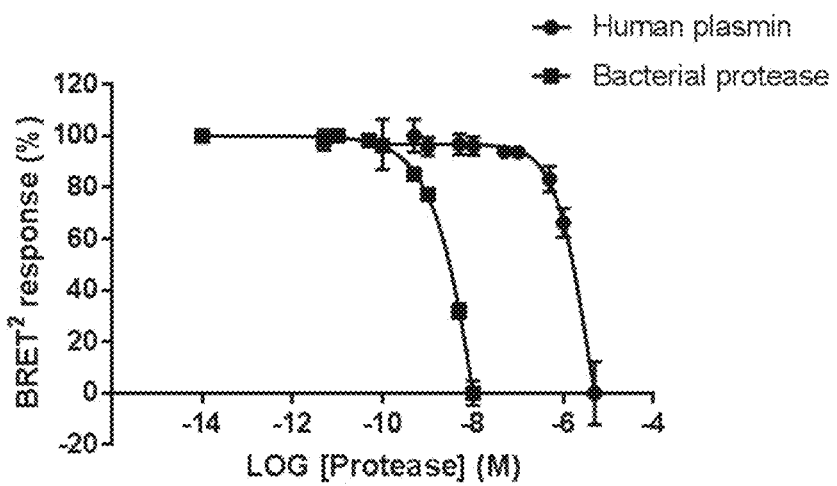

FIG. 10—BRET$^2$ response of Pflu sensor 3 after incubation of the sensor with various concentrations of human plasmin and crude bacterial protease in 50% full fat UHT milk for 10 minutes.

Figure 11:
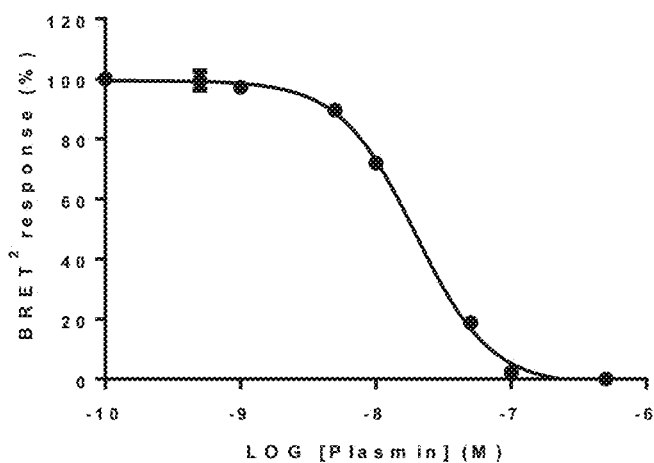

FIG. 11—Calibration of BRET$^2$ plasmin sensor using human plasmin added to heat treated raw milk following the pre-treatment protocol of Rauh et al. (2014).

Figure 12:
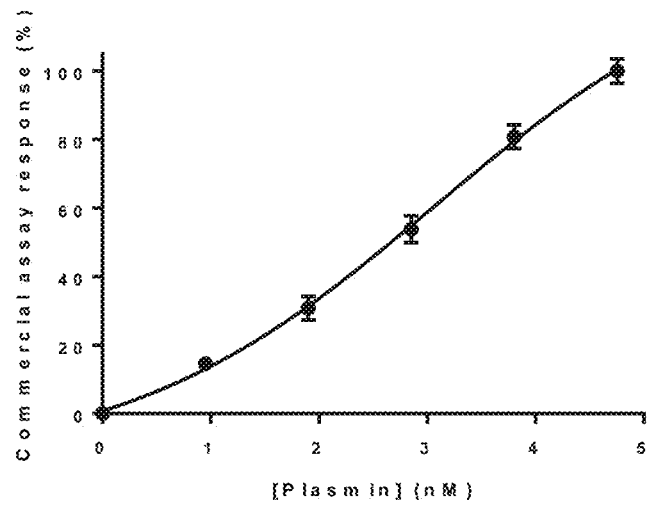

FIG. 12—Calibration of D-Val-Leu-Lys-4-nitroanilide dihydrochloride using human plasmin added to heat treated raw milk sample following the pre-treatment protocol of Rauh et al. (2014).

Figure 13:
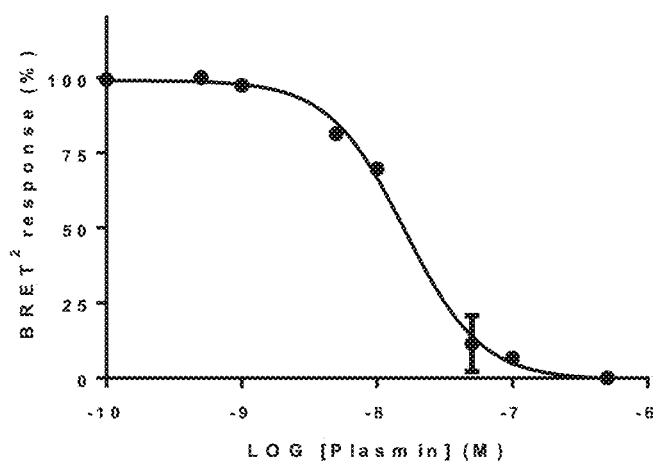

FIG. 13—Calibration of BRET$^2$ plasmin sensor using human plasmin added to heat treated raw milk sample following the two-step pre-treatment protocol.

Figure 14:
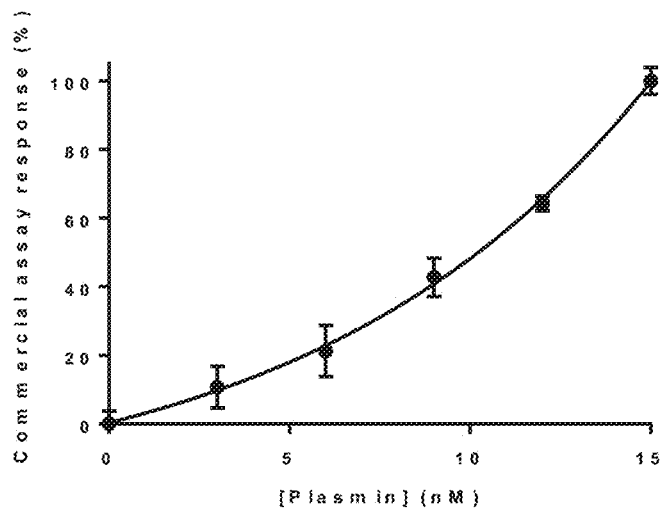

FIG. 14—Calibration of D-Val-Leu-Lys-4-nitroanilide dihydrochloride using human plasmin added to heat treated raw milk sample following the two-step pre-treatment protocol.

Figure 15:
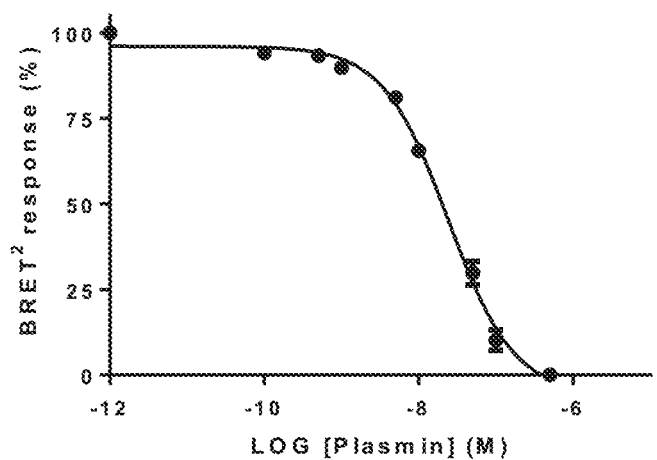

FIG. 15—Calibration of BRET$^2$ plasmin sensor using human plasmin added to heat treated raw milk sample following the one-step pre-treatment protocol.

Figure 16:
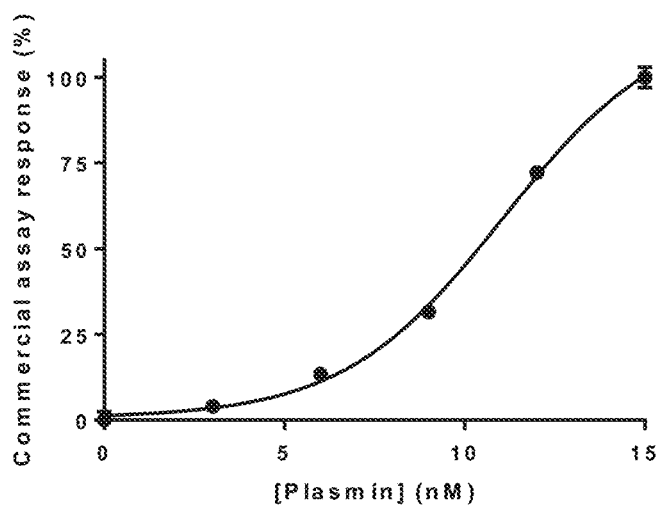

FIG. 16—Calibration of D-Val-Leu-Lys-4-nitroanilide dihydrochloride using human plasmin added to heat treated raw milk sample following the one-step pre-treatment protocol.

Figure 17:
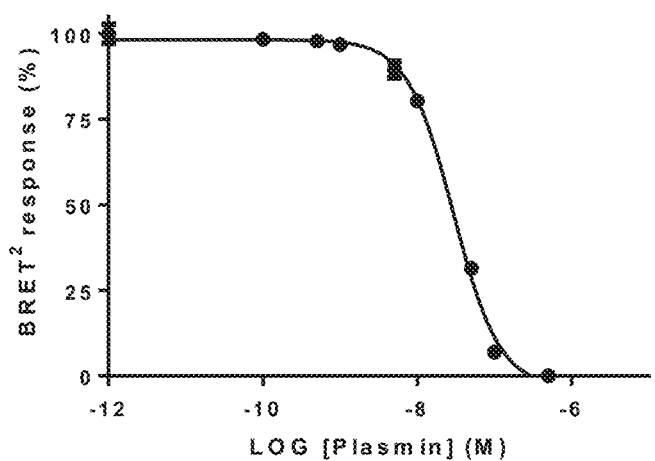

FIG. 17—Calibration of BRET$^2$ plasmin sensor using human plasmin added to heat treated raw milk sample following the one-step pre-treatment protocol with low power sonication.

Figure 18:
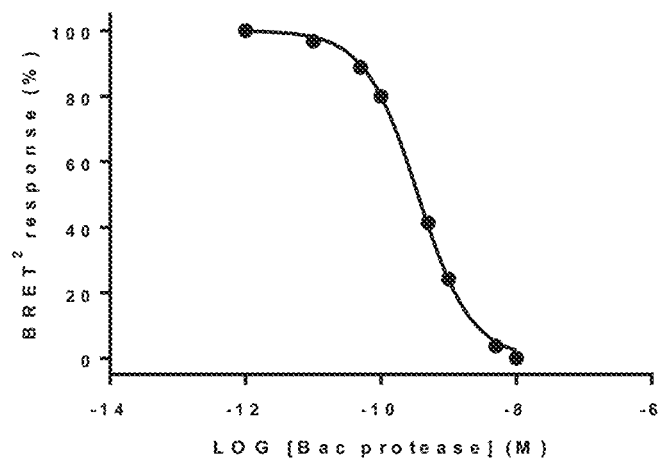

FIG. 18—Calibration of bacterial protease using the Pflu1 sensor in raw milk following the one-step pre-treatment protocol with low power sonication.

Figure 19:
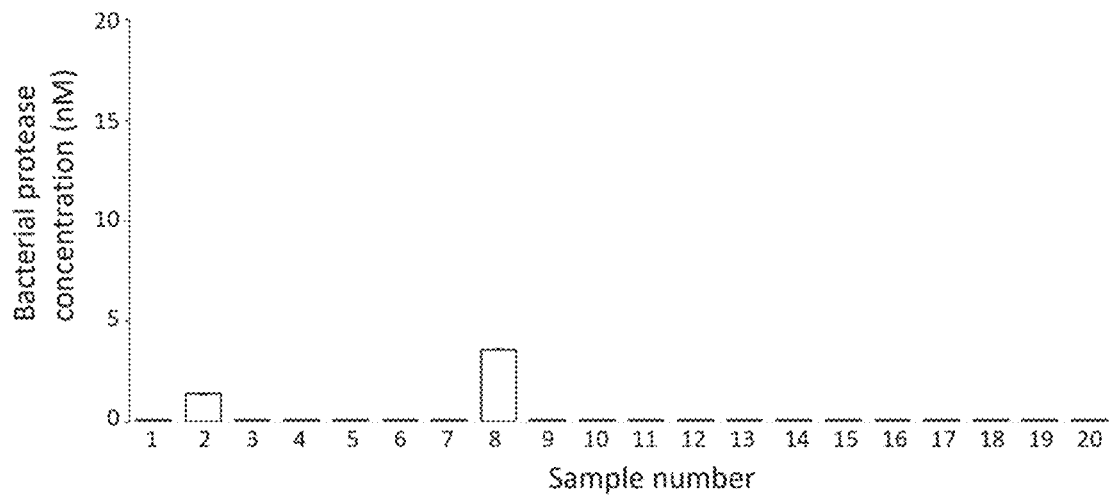

FIG. 19—Bacterial protease levels measured in raw milk samples using Pflu biosensor following the one-step pre-treatment protocol with low power sonication. Samples 1-20 are independent raw milk samples.

Figure 20:
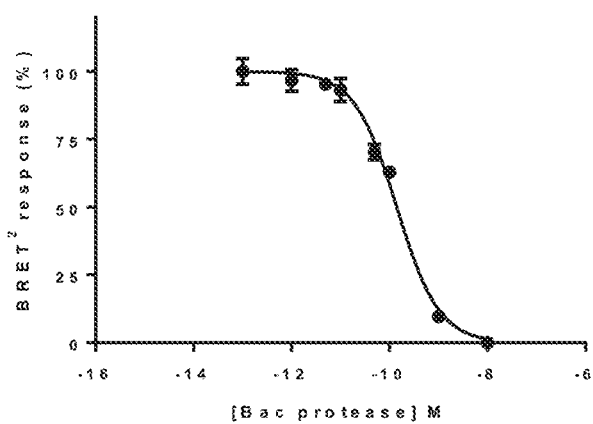

FIG. 20—Calibration of bacterial protease using the Pflu1 sensor in raw milk without pre-treatment following 10 minutes incubation at 28° C.

Figure 21:
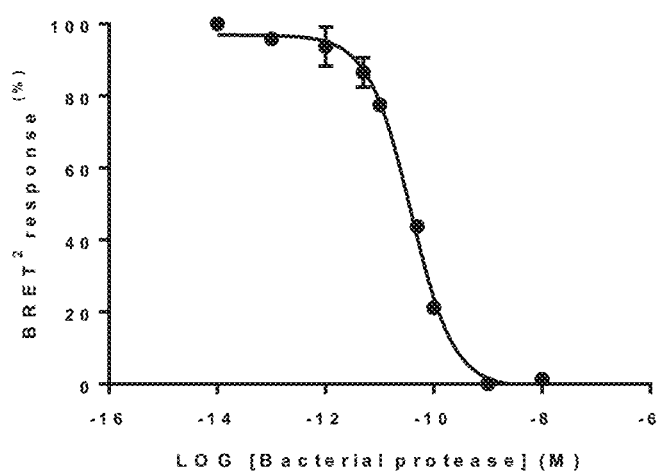

FIG. 21—Calibration of bacterial protease using the Pflu1 sensor in raw milk without pre-treatment following 2 hours incubation at 28° C.

Figure 22:
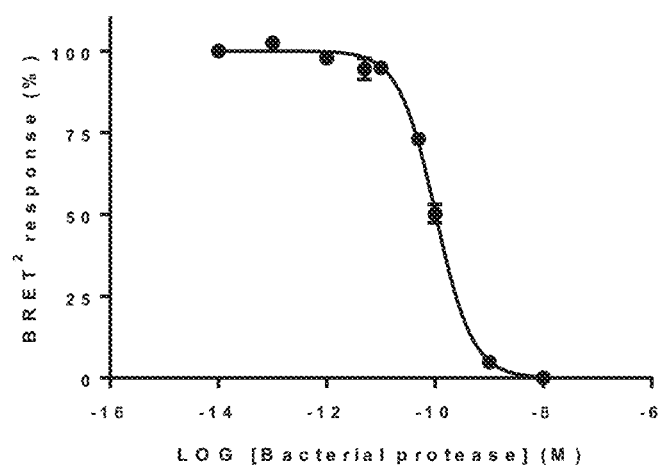

FIG. 22—Calibration of bacterial protease using the Pflu1 sensor in raw milk with one-step pre-treatment protocol with low power sonication following 2 hours incubation at 28° C.

Figure 23:
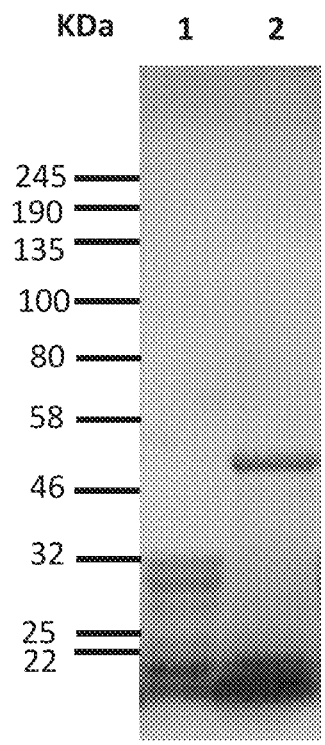

FIG. 23—SDS-PAGE of crude extract prepared from skimmed milk incubated with *P. fluorescens* strain 117 (lane 2) or control (lane 1).

Figure 24:
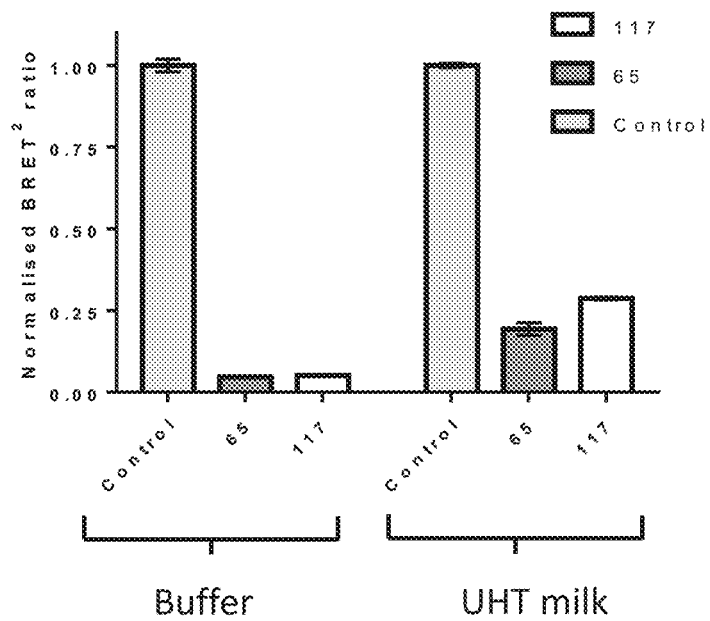

FIG. 24—BRET$^2$ response of Pflu1 sensor after incubation of the sensor with 0 (control) or 1 nM of crude bacterial protease from *P. fluorescens* strains 65 and 117 for 10 minutes in buffer and UHT milk.

Figure 25:
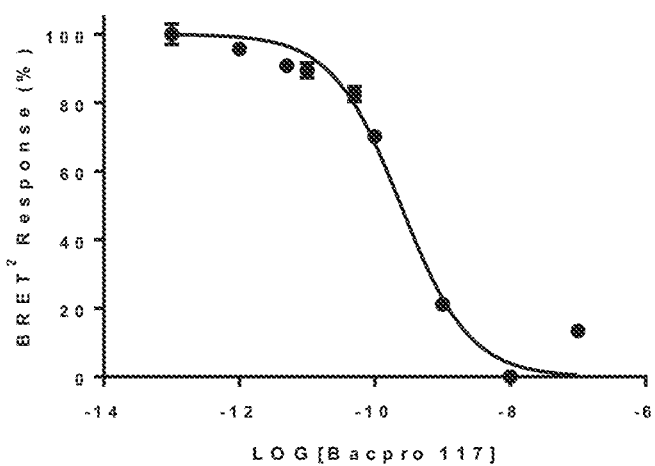

FIG. 25—Calibration of crude bacterial protease *P. fluorescens* strain 117 using the Pflu1 sensor in raw milk following 2 hours incubation at 28° C.

Figure 26:
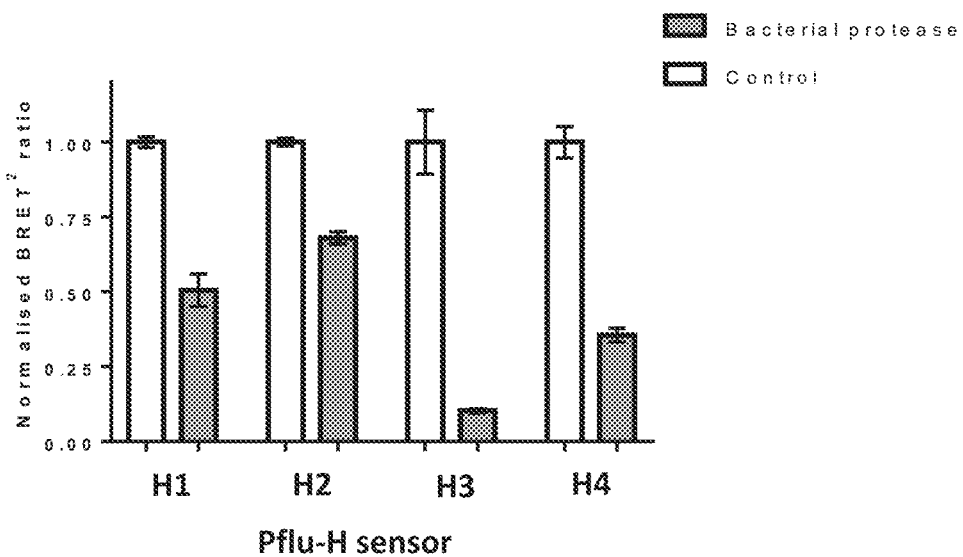

FIG. 26—BRET$^2$ response of Pflu-H sensor series after incubation of the sensor with 0 (control) or 1 nM of crude bacterial protease from *P. fluorescens* strains 65 for 10 minutes in buffer.

Figure 27:
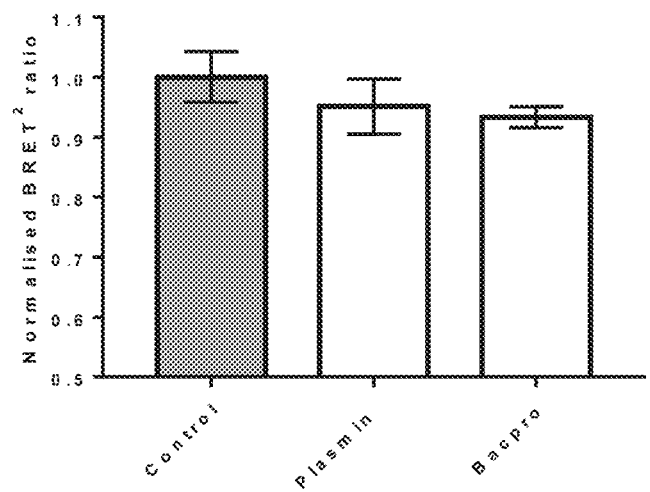

FIG. 27—BRET$^2$ response of Pflu-H1 sensor after incubation of the sensor with UHT milk spiked with 0 (control) or 1 nM of crude bacterial protease from *P. fluorescens* strains 65 or 1 nM Bovine plasmin for 10 minutes in buffer.

Figure 28:
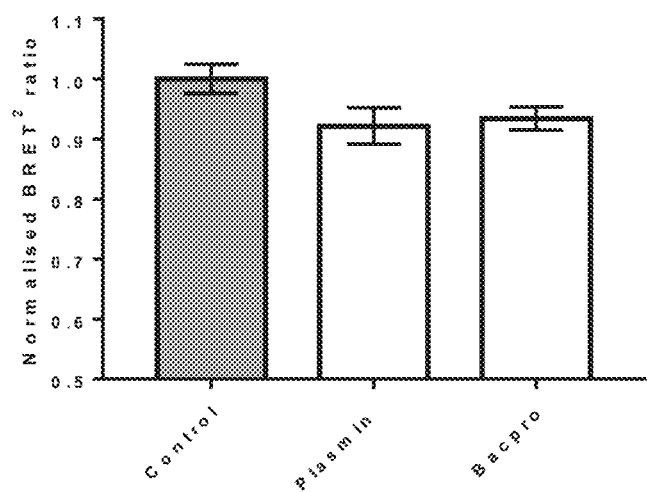

FIG. 28—BRET$^2$ response of Pflu-H2 sensor after incubation of the sensor with UHT milk spiked with 0 (control) or 1 nM of crude bacterial protease from *P. fluorescens* strains 65 or 1 nM Bovine plasmin for 10 minutes in buffer.

Figure 29:
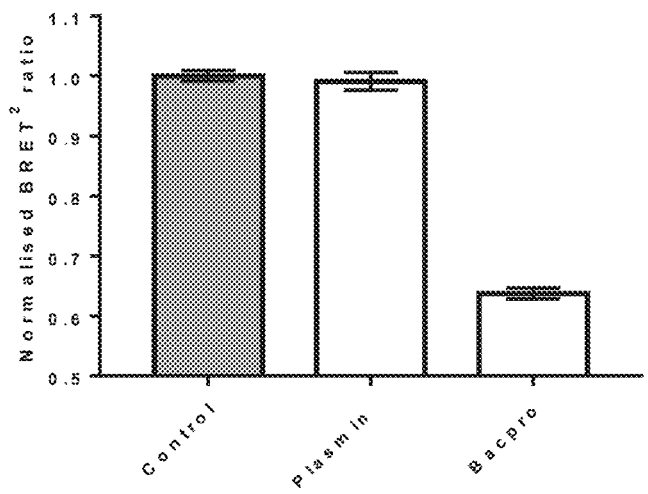

FIG. 29—BRET$^2$ response of Pflu-H3 sensor after incubation of the sensor with UHT milk spiked with 0 (control) or 1 nM of crude bacterial protease from *P. fluorescens* strains 65 or 1 nM Bovine plasmin for 10 minutes in buffer.

Figure 30:
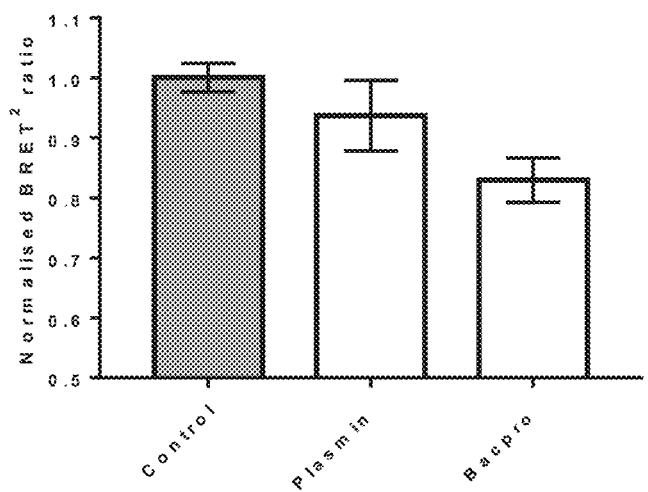

FIG. 30—BRET$^2$ response of Pflu-H4 sensor after incubation of the sensor with UHT milk spiked with 0 (control) or 1 nM of crude bacterial protease from *P. fluorescens* strains 65 or 1 nM Bovine plasmin for 10 minutes in buffer.

Figure 31:
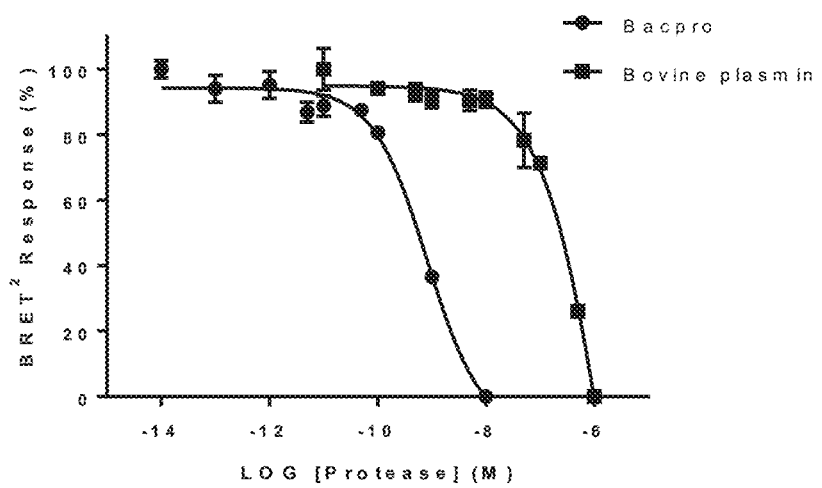

FIG. 31—BRET$^2$ response of Pflu-H1 sensor after incubation of the sensor with various concentrations of bovine plasmin and crude bacterial protease in 50% raw milk for 10 minutes.

Figure 32:
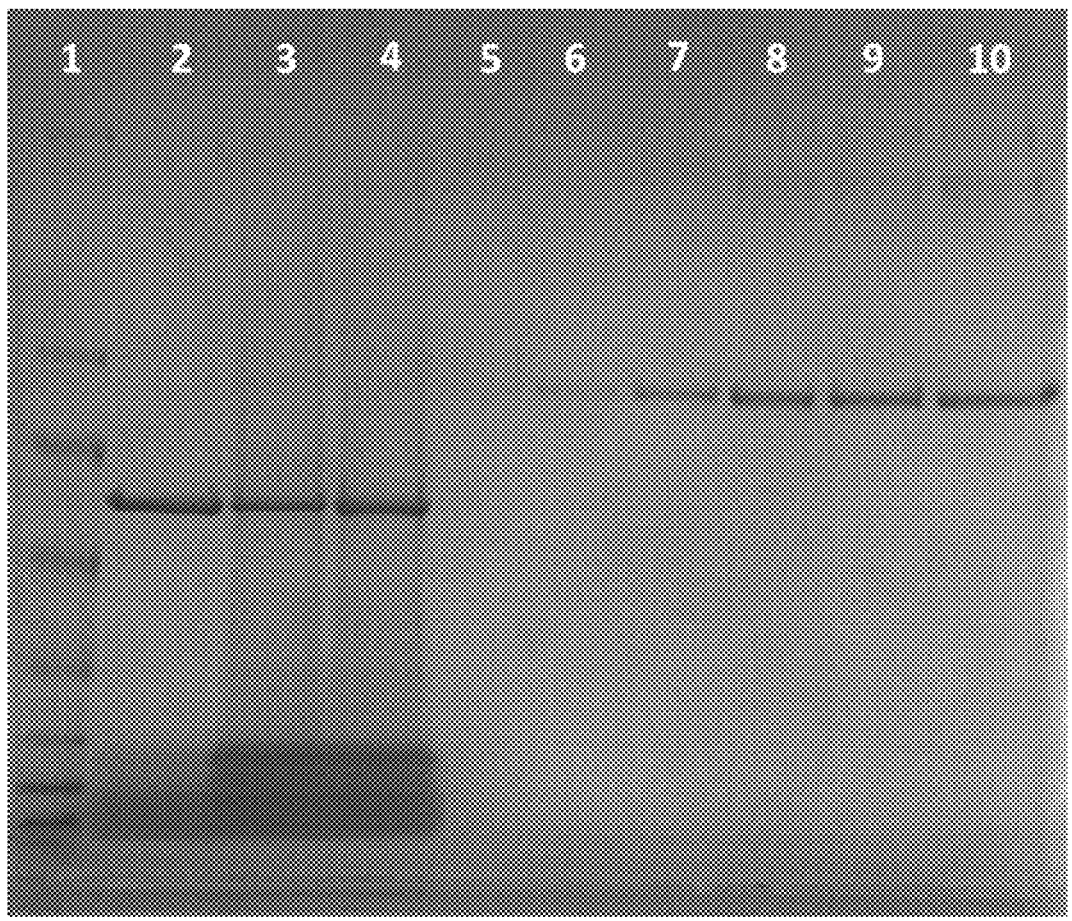

FIG. 32—SDS-PAGE of crude extract prepared from skimmed milk incubated with *P. fluorescens*. Marker (lane 1), strain 65-1 (lane 2), 65-2 (lane 3), 117 (lane 4), 100 ng BSA (lane 5), 200 ng BSA (lane 6), 400 ng BSA (lane 7), 600 ng BSA (lane 8), 800 ng BSA (lane 9) and 1000 ng BSA (lane 10).

Figure 33:
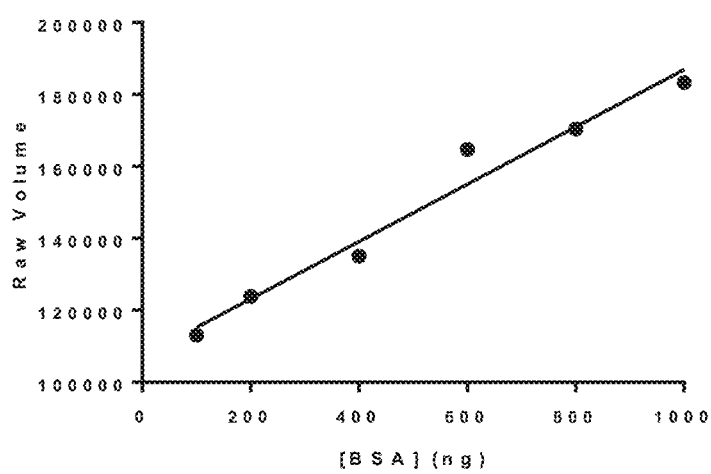

FIG. 33—Calculated volume for bands for different BSA concentrations (ng) on SDS-PAGE gel determined by densitometric analysis using Image Quant TL.

Figure 34:
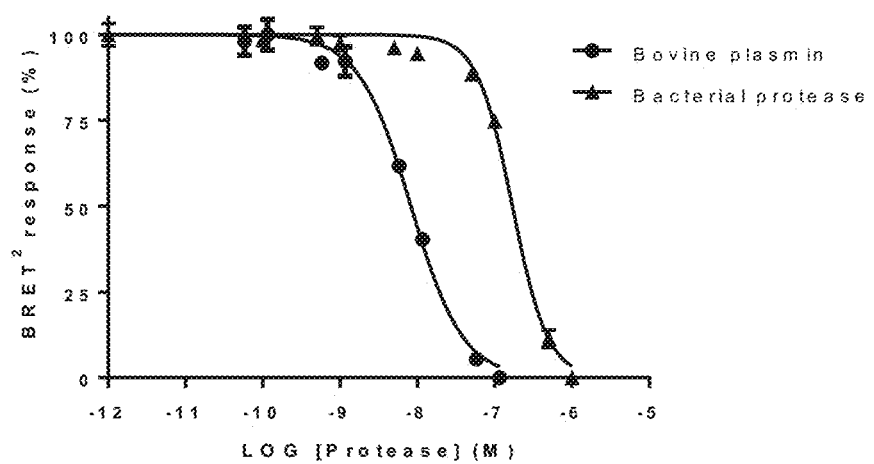

FIG. 34—BRET$^2$ response of Pflu sensor 1 after incubation of the sensor with various concentrations of bovine plasmin and crude bacterial protease in 50% full fat UHT milk for 10 minutes. Bacterial protease determined by comparison to BSA standard.

KEY TO SEQUENCE LISTING

SEQ ID NO: 1-94 and 112 to 115—Target sequence for protease sensor molecule.
SEQ ID NO: 95-101—Linker sequences.
SEQ ID NO: 102—Nucleotide sequence encoding GFP$^2$-Pflu1-RLuc2.
SEQ ID NO: 103—Nucleotide sequence encoding GFP$^2$-Pflu2-RLuc2.
SEQ ID NO: 104—Nucleotide sequence encoding GFP$^2$-Pflu3-RLuc2.
SEQ ID NO: 105—GFP$^2$-Pflu1-RLuc2 fusion protein.
SEQ ID NO: 106—GFP$^2$-Pflu2-RLuc2 fusion protein.
SEQ ID NO: 107—GFP$^2$-Pflu3-RLuc2 fusion protein.
SEQ ID NO: 108—Nucleotide sequence encoding GFP$^2$-plas1-RLuc2.
SEQ ID NO: 109—GFP$^2$-plas1-RLuc2 fusion protein.
SEQ ID NO: 110—Plasmin target sequence.
SEQ ID NO: 111—Plas1 target sequence.
SEQ ID NO: 116—Nucleotide sequence encoding GFP$^2$-Pflu-H1-RLuc2.
SEQ ID NO: 117—Nucleotide sequence encoding GFP$^2$-Pflu-H2-RLuc2.
SEQ ID NO: 118—Nucleotide sequence encoding GFP$^2$-Pflu-H3-RLuc2.
SEQ ID NO: 119—Nucleotide sequence encoding GFP$^2$-Pflu-H4-RLuc2.
SEQ ID NO: 120—GFP$^2$-Pflu-H1-RLuc2 fusion protein.
SEQ ID NO: 121—GFP$^2$-Pflu-H2-RLuc2 fusion protein.
SEQ ID NO: 122—GFP$^2$-Pflu-H3-RLuc2 fusion protein.
SEQ ID NO: 123—GFP$^2$-Pflu-H4-RLuc2 fusion protein.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in protein chemistry, protease biology, dairy science, dairy technology, and biochemistry and the like).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Unless the context suggests otherwise, the mention of a term in singular such as sensor and substrate clearly means the plural as well. For instance, logically many individual sensor molecules will be flowed through the device or contained within a well rather than a single molecule.

As used herein, the term about, unless stated to the contrary, refers to +/−10%, more preferably +/−5%, even more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Sensor

Throughout the specification "sensor", "bacterial protease sensor" and "sensor molecule" are used interchangeably.

In one aspect the present application provides a *Pseudomonas* spp. protease sensor molecule comprising a target sequence having at least one *Pseudomonas* spp. protease cleavage site selected from the group consisting of KQ, SF, FM, KK, KN, NQ, NT, EI and combinations thereof, and one or more of the following features: (i) the target sequence is less than about 50 amino acids in length; (ii) a detectable label; and/or (iii) two or more of the protease cleavage sites; wherein cleavage of the target sequence by a *Pseudomonas* spp. protease produces a detectable change.

In some embodiments, the *Pseudomonas* spp. is *Pseudomonas fluorescens*, *Pseudomonas fragi*, *Pseudomonas ludensis*, *Pseudomonas putida*, *Pseudomonas* LBSA1 or *Pseudomonas aureofaciens*. Preferably, the *Pseudomonas* spp. is *Pseudomonas fluorescens*.

In some embodiments, the *Pseudomonas* spp. protease is an extracellular protease. Preferably, the protease is relatively heat stable. As used herein, "relatively heat stable" means that the protease retains at least 10%, 20%, 30%, 40%, 50%, 60%, 70% or 80% of its original activity after heat treatment to 95° C. for at least 8 minutes or after heat treatment to 140° C. for 3 s or heat treatment regimes delivering similar areas under the time/temperature curve. Preferably, the protease retains at least 20% of its original activity after heat treatment to 95° C. for at least 8 minutes or after heat treatment to 140° C. for 3 s or heat treatment regimes delivering similar areas under the time/temperature curve. In some embodiments, the protease is an alkaline metalloprotease. In some embodiments, the protease belongs to the serralysin family of proteases. In some embodiments, the protease is an AprX protease. In some embodiments, the protease has at least has at least 50%, 60%, 70%, 80%, 90%, 95% or 99% sequence identity, or 100% sequence identity, to AprX of *P. fluorescens* n° 114 (NCBI GenPept ID BAA28268).

In some embodiments, the sensor is a continuous stretch of amino acids. For example, the target sequence and detectable label are a single stretch of amino acids such as, but not limited to, a chemiluminescent donor protein domain covalently attached to the N-terminus of the target sequence and an acceptor protein domain covalently attached to the C-terminus of the target sequence, or an acceptor protein domain covalently attached to the N-terminus of the target sequence and a chemiluminescent donor protein domain covalently attached to the C-terminus of the target sequence, or a fluorophore protein domain covalently attached to the N-terminus of the target sequence and an acceptor protein domain covalently attached to the C-terminus of the target sequence, or an acceptor protein domain covalently attached to the N-terminus of the target sequence and a fluorophore protein domain covalently attached to the C-terminus of the target sequence.

In some embodiments; there is also provided an isolated nucleic acid which comprises a polynucleotide sequence encoding a sensor or target sequence as defined herein. For example, in one embodiment the nucleic acid molecule comprises a sequence encoding the polypeptide sequence of SEQ, II) NO, SI, SEQ, II) NO. 82, or SEQ. ID NO. 83. In addition to the sequence encoding the sensor of the invention; the nucleic acid molecule may contain other sequences such as primer sites, transcription factor binding sites, vector insertion sites and sequences which resist nucleolytic degradation (e.g. polyadenosine tails). The nucleic acid molecule may be DNA or RNA and may include synthetic nucleotides, provided that the polynucleotide is still capable of being translated in order to synthesize a protein of the invention.

In some embodiments, the nucleic acid forms part of a vector such as a plasmid. In addition to the nucleic acid sequence described above, the plasmid comprises other elements such as a prokaryotic origin of replication (for example, the *E. coli* OR1 origin of replication) an autonomous replication sequence, a centromere sequence; a promoter sequence capable of expressing the nucleic acid in the host cell which is operably linker to the nucleic acid, a terminator sequence located downstream of the nucleic acid sequence, an antibiotic resistance gene and/or a secretion signal sequence. A vector comprising an autonomous replication sequence is also a yeast artificial chromosome. In some alternative embodiments, the vector is a virus, such as a bacteriophage and comprises, in addition to the nucleic acid sequence of the invention, nucleic acid sequences for replication of the bacteriophage, such as structural proteins, promoters, transcription activators and the like.

The nucleic acid or vector of the invention may be used to transfect or transform host cells in order to synthesize the sensor or target sequence of the invention. Suitable host cells include prokaryotic cells such as *E. coli* and eukaryotic cells such as yeast cells, or mammalian or plant cell lines. Host cells are transfected or transformed using techniques known in the art such as electroporation; calcium phosphate base methods; a biolistic technique or by use of a viral vector.

After transfection/transformation, the nucleic acid or vector of the invention is transcribed as necessary and translated. In some embodiments, the synthesized protein is extracted from the host cell, either by virtue of its being secreted from the cell due to, for example, the presence of secretion signal in the vector; or by lysis of the host cell and purification of the protein therefrom.

In some embodiments, the sensor is provided as a cell-free composition. As used herein, the term "cell free composition" refers to an isolated composition which contains few, if any, intact cells and which comprises the sensor. Examples of cell free compositions include cell (such as yeast cell) extracts and compositions containing an isolated and/or recombinant sensor molecules (such as proteins). Methods for preparing cell-free compositions from cells are well-known in the art.

Target Sequence

The sensor of the present application comprises a target sequence having at least one *Pseudomonas* spp. protease cleavage site. A *Pseudomonas* spp. protease cleavage site is at least a dipeptide sequence that is cleaved by a *Pseudomonas* spp. protease. Typically, the first amino acid in the dipeptide sequence is referred to as the P1 residue and the second amino acid is referred to as the P1' residue. The protease cleaves the peptide bond between the P1 and P1' residues. As would be understood by the person skilled in the art the residues surrounding the protease cleavage site can assist with protease recognition of the cleavage site, specificity and cleavage efficiency.

In some embodiments, the protease cleavage site is selected from the group consisting of KQ, SF, FM, KK, KN, NQ, NT, EI, QQ and combinations thereof. In some embodiments, the protease cleavage site is selected from the group consisting of KQ, SF, FM, KK, KN, NQ, NT, EI and combinations thereof. In some embodiments, the protease cleavage site is selected from the group consisting of SF, FM, KK, KN, NQ, NT, EI, QQ and combinations thereof. In some embodiments, the protease cleavage site is selected from the group consisting of SF, FM, KK, KN, NQ, NT, EI and combinations thereof. In some embodiments, the protease cleavage site is KQ. In some embodiments, the protease cleavage site is SF. In some embodiments, the protease cleavage site is FM. In some embodiments, the protease cleavage site is KK. In some embodiments, the protease cleavage site is KN. In some embodiments, the protease cleavage site is NQ. In some embodiments, the protease cleavage site is NT. In some embodiments, the protease cleavage site is EI. In some embodiments, the protease cleavage site is QQ.

In some embodiments, the target sequence comprises at least two protease cleavage sites. In some embodiments, the target sequence comprises at least three, at least four, at least five, at least six or at least 7 protease cleavage sites. In some embodiments, the target sequence comprises two, three, four, five, six or seven protease cleavage sites. The protease cleavage site may comprise multiple repeats of the same cleavage site, for example $(KQ)_n$, $(FM)_n$, $(FM)_n$, $(KK)_n$, $(KN)_n$, $(NQ)_n$, $(NT)_n$, $(EI)_n$, $(QQ)_n$ and combinations thereof, where n is an integer equal to or greater than 2, for example 2, 3, 4, 5, 6, 7, 8, 9, 10, 11, 12, 13, 14, 15, 20, 25, 30, 40, 50 or higher. The protease cleavage sites can be included in the target sequence in any order. For example, the target sequence comprises KQKQ (SEQ ID NO: 1), KQSF (SEQ ID NO: 2), KQFM (SEQ ID NO: 3), KQKK (SEQ ID NO: 4), KQKN (SEQ ID NO: 5), KQNQ (SEQ ID NO: 6), KQNT (SEQ ID NO: 7), KQEI (SEQ ID NO: 8), KQQQ (SEQ ID NO: 75), SFSF (SEQ ID NO: 9), SFFM (SEQ ID NO: 10), SFKK (SEQ ID NO: 11), SFKN (SEQ ID NO: 12), SFNQ (SEQ ID NO: 13), SFNT (SEQ ID NO: 14), SFEI (SEQ ID NO: 15), SFQQ (SEQ ID NO: 76), FMFM (SEQ ID NO: 16), FMKK (SEQ ID NO: 17), FMKN (SEQ ID NO: 18), FMNQ (SEQ ID NO: 19), FMNT (SEQ ID NO: 20), FMEI (SEQ ID NO: 21), FMQQ (SEQ ID NO: 77), KKKK (SEQ ID NO: 22), KKKN (SEQ ID NO: 23), KKNQ (SEQ ID NO: 24), KKNT (SEQ ID NO: 25), KKEI (SEQ ID NO: 26), KKQQ (SEQ ID NO: 78), KNKN (SEQ ID NO: 27), KNNQ (SEQ ID NO: 28), KNNT (SEQ ID NO: 29), KNEI (SEQ ID NO: 30), KNQQ (SEQ ID NO: 79), KNFM (SEQ ID NO: 31), KNKK (SEQ ID NO: 32), NQNQ (SEQ ID NO: 33), NQQQ (SEQ ID NO: 80), NTNT (SEQ ID NO: 34), NTEI (SEQ ID NO: 35), NTQQ (SEQ ID NO: 81), EIEI (SEQ ID NO: 36), EIQQ (SEQ ID NO: 82), QQQQ (SEQ ID NO: 83), QQKQ (SEQ ID NO: 84), QQSF (SEQ ID NO: 85), QQFM (SEQ ID NO: 86), QQKK (SEQ ID NO: 87), QQKN (SEQ ID NO: 88), QQNQ (SEQ ID NO: 89), QQNT (SEQ ID NO: 90), QQEI (SEQ ID NO: 91), KQQ (SEQ ID NO: 92) and any combination thereof.

In some embodiments, the target sequence comprises KQ, SFM (SEQ ID NO: 37), KKNQ (SEQ ID NO: 24), NT, KQQ (SEQ ID NO: 92) and EI and combinations thereof. In some embodiments, target sequence at least comprises SFM (SEQ ID NO: 37) and/or KKNQ (SEQ ID NO: 24). For example, the target sequence can comprise SFMKKNQ (SEQ ID NO: 38) or KKNQSFM (SEQ ID NO: 39) or both.

In some embodiments, the target sequence comprises SKMXXPP (SEQ ID NO: 40), where X is any amino acid. In some embodiments, the target sequence comprises PPXXXSKMXXPP (SEQ ID NO: 41), PPXXSKMXXPP (SEQ ID NO: 42) or PPXSKMXXPP (SEQ ID NO: 43), where X is any amino acid.

In some embodiments, the target sequence comprises PPVKQPPP (SEQ ID NO: 44).

In some embodiments, the target sequence does not comprise a dipeptide sequence that can be cleaved by bovine plasmin. It has been disclosed that bovine plasmin cleaves the peptide bond between KZ, where Z is an amino acid selected from the group consisting of K, Y, V or E. Therefore, in some embodiments the target sequence does not comprise KK, KY, KV or KE. Preferably, the protease cleavage site is selected from the group consisting of KQ, SF, FM, KN, NQ, NT, EI and combinations thereof. In some embodiments, the protease cleavage site is selected from the group consisting of SF, FM, KN, NQ, NT, EI and combinations thereof.

In some embodiments, the target sequence comprises SFMKKNQNTEI (SEQ ID NO: 45), SFMNTKKNQEI (SEQ ID NO: 46), SFMQNTEIKKN (SEQ ID NO: 47), SFMNQKKNTEI (SEQ ID NO: 48), SFMNQNTKKEI (SEQ ID NO: 49), SFMNQNTEIKK (SEQ ID NO: 50), KKNQSFMNTEI (SEQ ID NO: 51), KKNQNTSFMEI (SEQ ID NO: 52), KKNQNTEISFM (SEQ ID NO: 53), KKSFMNQNTEI (SEQ ID NO: 54), KKNQSFMEINT (SEQ ID NO: 55), KKNQEISFMNT (SEQ ID NO: 56), SFMNQNTEI (SEQ ID NO: 57), NQSFMNTEI (SEQ ID NO: 58), NQNTSFMEI (SEQ ID NO: 59), NQNTEISFM (SEQ ID NO: 60), SFMNTNQEI (SEQ ID NO: 61), SFMNTEINQ (SEQ ID NO: 62), SFMNQEINT (SEQ ID NO: 63), NQSFMEINT (SEQ ID NO: 64), NQEISFMNT (SEQ ID NO: 65), SFMEINQNT (SEQ ID NO: 66), EISFMNTNQ (SEQ ID NO: 67), EINTSFMNQ (SEQ ID NO: 68), EINTNQSFM (SEQ ID NO: 69), LSFMAIP (SEQ ID NO: 70) or LFMSFAIP (SEQ ID NO: 71). Preferably, the target sequence comprises SFMKKNQNTEI (SEQ ID NO: 45), SFMNQNTEI (SEQ ID NO: 57) or LSFMAIP (SEQ ID NO: 70).

In some embodiments, the target sequence comprises LQGSFMKKNQNTEIGSFE (SEQ ID NO: 72), LQGSFMNQNTEIGSFE (SEQ ID NO: 73), LQGSLSF-MAIPGSFE (SEQ ID NO: 74), or LQG-SKQKQKQKQGSFE (SEQ ID NO: 112). Other examples include LQGSPPLKQPPPGSFE (SEQ ID NO:113), LQGSPPLQQPQPGSFE (SEQ ID NO:114) and LQGGSGGSLKQQGSGGSFE (SEQ ID NO:115).

In some embodiments, the target sequence comprises GSPPLQQPPPGS (SEQ ID NO: 93) or GGSGGSLKQQGGSGGS (SEQ ID NO: 94).

The target sequence comprises or consists of amino acids which do not form part of the detectable label. Therefore, the target sequence may comprise an amino acid linker which is attached to the detectable label. In some embodiments, a linker can be located at the N- and/or C-terminus of the target sequence. In some embodiments, the linker comprises one or more glycine, serine and/or proline residues. For example, in some embodiments, the linker comprises an amino acid sequence selected from LQG (SEQ ID NO: 95), GSFE (SEQ ID NO: 96), GSSGGS (SEQ ID NO: 97), GSPPL (SEQ ID NO: 98), PPPGS (SEQ ID NO: 99), GGSGGS (SEQ ID NO: 100), GGSGGSL (SEQ ID NO: 101) and PPVKQPPP (SEQ ID NO: 44). The linker sequence can be located at the N-terminus of the target sequence, the C-terminus of the target sequence or both. When a linker is located at both the N- and C-terminus of the target sequence, the linker sequence can be the same or different. Without wishing to be bound by theory, the linker may serve one or more of the following purposes: (i) help ensure that the protease cleavage site is in the preferred conformation for cleavage; (ii) improve the accessibility of the protease cleavage site; (iii) increase the magnitude of the detectable change (for example, where the detectable label is a BRET pair, the linker sequence can function to increase the BRET ratio); (iv) contribute to recognition of the target sequence by the protease; and/or (v) contribute to the specificity of the sensor (and/or target sequence) for *Pseudomonas* spp. protease over bovine plasmin. Further without wishing to be bound by theory, proline residues in the target sequence may contribute to the specificity of the sensor for *Pseudomonas* spp. protease over bovine plasmin.

In some embodiments, the linker comprises an amino acid or series of amino acids than can be used for purification or for attachment of the detectable label. For example, the linker can comprise a histidine tag for purification or self-assembly with the detectable label. In another example, the linker can comprise a reactive group (e.g. cysteine) for addition of the detectable label.

In preferred embodiments, the target sequence is less than about 50 amino acids. For example, the target sequence comprises between about 2 and about 50 amino acids. In some embodiments, the target sequence comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. The length of the target sequence (in amino acids) can be varied to increase the sensitivity of the sensor.

Detectable Label(s)

Preferably the sensor comprises a detectable label. As used herein, the term "label" refers to a compound or composition that is specifically associated either directly or indirectly, by covalent bonding or non-covalent interactions, with the target sequence. In preferred embodiments, the label is attached to the target by covalent bonding, for example, a peptide, thioether or ester bond. The person skilled in the art would be aware of the techniques that can be used for covalently attaching labels to the target sequence. Any substance generally capable of producing a signal that is detectable visually or by an instrumental device may be used as a detectable label.

A label may be detectable directly, for example, the label can be a fluorescent or phosphorescent molecule (e.g., FITC, rhodamine, lanthanide phosphors), or indirectly, for example, by enzymatic activity (e.g., horseradish peroxidase, beta-galactosidase, luciferase, alkaline phosphatase). Incorporation of a label can be achieved by a variety of means known in the art, for example, by use of high binding affinity between two molecules such as an enzyme and its substrate (e.g., ATPase and ATP), streptavidin and biotin or an antigen or epitope and an antibody. Other means include, by way of illustration, the use of radiolabeled or biotinylated nucleotides in polymerase-mediated primer extension reactions or epitope-tagging via recombinant expression or synthetic means. Labels can be attached directly or indirectly via spacer arms or linkers of various lengths. The detectable label can be a protein or non-protein. For example, the detectable label with the target sequence, and any linker if present, can form a continuous stretch of amino acids.

In preferred embodiments, the detectable label comprises two or more components. The two or more components may be the same or different. For example, the two or more components may be the same chromophore or the two or more components can be i) a chemiluminescent donor domain and an acceptor domain covalently attached to the target sequence, or ii) a fluorophore domain and a acceptor domain.

In some embodiments, the sensor has an $EC_{50}$ of between about 0.01 and about 100 nM, or about 0.1 and about 10 nM, or about 0.2 and about 5 nM for a *Pseudomonas* spp. protease. In some embodiments, the sensor has an $EC_{50}$ of between about 0.4 and about 3 nM for a *Pseudomonas* spp. protease, for example the $EC_{50}$ can be about 0.1, 0.2, 1.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 nM.

There is also a need for sensors which discriminate between spoilage due to intrinsic factors such as plasmin and extrinsic factors such as the bacterial proteases. In some embodiments, the sensor of the present invention is at least 5 times, 10 times, 20 times, 30 times, 40 times, 50 times, 100 times, 150 times, 200 times, 250 times, 300 times, 350 times or 400 times more sensitive for a *Pseudomonas* spp. protease compared to plasmin. Preferably, the sensor is at least 100 times, 150 times, 200 times, 250 times, 300 times, 350 times or 400 times more sensitive for a *Pseudomonas* spp. protease compared to plasmin. In this context, the sensitivity of a sensor for a *Pseudomonas* spp. protease compared to plasmin is calculated by taking the ratio of the $EC_{50}$ calculated from the plasmin calibration curve and dividing it the $EC_{50}$ calculated from bacterial protease calibration curve.

In some embodiments, the detectable label is selected from the group consisting of a chromophore, a nanoparticle, a quantum dot, a viologen and combinations thereof.

In some embodiments, the detectable change is a change in resonance energy transfer, acoustics, electrochemical potential, fluorescence, chemiluminescence, phosphorescence, absorbance, antibody binding, BRET ratio, FRET efficiency or mass. In some embodiments, cleavage of the target sequence by a *Pseudomonas* spp. protease results in a detectable change in resonance energy transfer (RET).

Chromophore

In some embodiments, the detectable label comprises a chromophore. Throughout the specification, chromophore and luminophore are used interchangeably. As used herein, chromophore is defined broadly as any photoactive compound and includes any coloured or non-coloured light absorbing species and any species which fluoresces. Any suitable chromophore can be used in the sensors of the present application. Suitable chromophores include, but are not limited to, any organic or inorganic dyes, fluorophores, phosphophores, light absorbing nanoparticles, combinations thereof, or the metalated complexes thereof. Therefore, in some embodiments, the chromophore is selected from the group consisting of organic dyes, inorganic dyes, phosphophores, light absorbing nanoparticles, combinations thereof, and the metalated complexes thereof.

In some embodiments, the organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl) acridinium. Examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHerS, Dye-33, Cy7, CyS, Cy5.5, Cy3Cy5 ET, Cy3B, Cy3, Cy3.5, Cy2, $CBQCA_5NIR1$, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

In some embodiments, the inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxyphenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

In some embodiments, the detectable label is a fluorophore/phosphophore selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenylethynyl)anthracene).

In some embodiments, the light absorbing nanoparticles comprise gold, silver, platinum or palladium.

In some embodiments, the phosphophore is a phosphorescent dye. In some embodiments, the phosphophore is a metal complex of one or more metals, such as ruthenium, osmium, rhenium, iridium, rhodium, platinum, indium, palladium, molybdenum, technetium, copper, iron, chromium, tungsten, zinc, and the like. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

The person skilled in the art would be aware of protease assays that use chromophores as a detectable label.

Nanoparticle

In some embodiments, the detectable label comprises a nanoparticle. As used herein, the term "nanoparticle" refers to metal nanocrystalline particles that can optionally be surrounded by a metal or nonmetal nanolayer shell. Suitable nanoparticles have a diameter of from about 1 nm to about 100 nm. In some embodiments, the diameter is preferably from about 10 nm to about 50 nm, and more preferably from about 5 nm to about 20 nm. The nanoparticles can comprise any type of metal (including elemental metal) or metal alloy. In some embodiments, the metal or metal alloy nanoparticles comprise a metal selected from the group consisting of gold (Au), silver (Ag), copper (Cu), nickel (Ni), palladium (Pd), platinum (Pt), cobalt (Co), rhodium (Rh), iridium (Ir), iron (Fe), ruthenium (Ru), osmium (Os), manganese (Mn), rhenium (Re), scandium (Sc), titanium (Ti), vanadium (V), chromium (Cr), zinc (Zn), yttrium (Y), zirconium (Zr), niobium (Nb), molybdenum (Mo), technetium (Tc), cadmium (Cd), lanthanum (La), lutetium (Lu), hafnium (Hf), tantalum (Ta), tungsten (W), actinium (Ac), lawrencium (Lr), rutherfordium (Rf), dubnium (Db), seaborgium (Sg), bohrium (Bh), Hassium (Hs), meitnerium (Mt), darmstadtium (Ds), roentgenium (Rg), ununbium (Uub), selenium (Se), and the oxides (e.g., FeO, $Fe_3O_4$, $Fe_2O_3$, $Fe_xO_y$ (non-stoichiometric iron oxide), CuO, NiO, $Ag_2O$, $Mn_2O_3$), hydroxides, sulfides, selenides, and tellurides of the foregoing, and combinations thereof.

In some embodiments, the core/shell nanoparticles comprise a metal or metal alloy core and a metal shell. In preferred embodiments, the cores are selected from the group consisting of Au, Ag, Cu, Co, Fe, and Pt. In preferred embodiments, the referred shells are selected from the group consisting of Au, Ag, Cu, Co, Fe, Pt, the metal oxides thereof, and combinations thereof. In some embodiments, the metal core/shell combinations are selected from the group consisting of Fe/Au, Fe/$Fe_3O_4$, and Au/$Fe_2O_3$. The core of the nanoparticle preferably has a diameter of from about 1 nm to about 25 nm, and more preferably from about 3 nm to about 5 nm. The metal shell of the core/shell nanoparticle preferably has a thickness of from about 0.5 nm to about 10 nm, and more preferably from about 0.5 to about 2 nm.

In some embodiments, the nanoparticles can be stabilized. As used herein, "stabilized" means the use of a ligand shell or monolayer to coat, protect, or impart properties to, the nanoparticle. For example, a ligand shell or monolayer can be used to protect the nanoparticle from bio-corrosion. In another example, a ligand shell or monolayer can be used to make the nanoparticle more or less soluble in a solvent such as water. The monolayer can comprise of several of the same ligands (i.e., homoligand) or a mixture of different ligands. The person skilled in the art would be aware of the techniques that can be used for attaching ligands to the surface of nanoparticles to form a ligand shell. For example, nanoparticles may be mixed in a solution containing the ligands to promote the coating of the nanoparticle. In another example, the nanoparticle can be coated with ligand and/or coating material by exposing the nanoparticles to a vapor phase of the ligand and/or coating material such that the ligand and/or coating material attaches to or bonds with the nanoparticle. In some embodiments, the ligands and/or coating material attach to the nanoparticle through covalent bonding. The ligands comprise functional groups that are attracted to the nanoparticle's metal surface. In some embodiments, the ligands comprise at least one group selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties. The number of ligands required to form a monolayer will be dependent upon the size of the nanoparticle.

In a preferred embodiment, stabilized nanoparticles comprise an organic monolayer surrounding the nanoparticle core. Any organic monoloayer known to the person skilled in the art may be used. For example, suitable organic monolayers can be selected from the group consisting of alkanethiolate monolayers, aminoalkylthiolate monolayers, alkylthiolsulfate monolayers, and organic phenols (e.g., dopamine and derivatives thereof). In some embodiments, the thickness of the organic monolayer is less than about 10 nm, and preferably less than about 5 nm.

Preferred stabilized nanoparticles are selected from the group consisting of trioctyl-phosphinoxide-stablized nanoparticles, amine-stabilized nanoparticles, carboxylic-acid-stabilized nanoparticles, phosphine-stabilized nanoparticles, thiol-stabilized nanoparticles, aminoalkylthiol-stabilized nanoparticles, and organic phenol-stabilized nanoparticles.

As a non-limiting example, the detectable label comprises gold nanoparticles. The application of gold nanoparticles to protease assays is discussed in Guarise et al. (2006).

Quantum Dot

In some embodiments, the detectable label comprises a quantum dot. Throughout the specification quantum dot and nanocrystal is used interchangeably. As used herein, a "quantum dot" is a semiconductor composed of atoms from groups II-VI or III-V elements of the periodic table (e.g., CdSe, CdTe and InP). Quantum dots of the same material, but with different sizes, can emit light of different colours. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, ΔE, between the valance and conduction band of the semiconductor is a function of the nanocrystal's size and shape. Compared to traditional organic fluorophores, quantum dots have slightly lower luminescence quantum yields but much larger absorption cross-sections and very low rates of photobleaching. Molar extinction coefficients of quantum dots are about $10^5$-$10^6$ $M^{-1}$ $cm^{-1}$, which is 10-100 times larger than dyes. As used herein, "quantum yield" refers to a measure of final emission of original energy donation.

Any quantum dot suitable for the purpose can be used. In some embodiments, the optical properties of quantum dots can be manipulated by synthesizing a shell. Typically, the shell is a stabilizing shell. Such quantum dots are known as core-shell quantum dots and include but are not limited to CdSe/ZnS, InP/ZnS, InP/CdSe. Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (such as, CdSe/ZnS) has a higher energy conduction band and a lower energy valance band than that of the core, resulting in confinement of both electron and hole in the core. The conduction and valance bands of the shell of type II quantum dots (such as CdTe/CdSe and CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are preferred. The alloy composition and internal structure, which can be varied, permits tuning the optical properties without changing the particles' size.

In some embodiments, quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe).

If different colour emission is needed for creating multiple sensors (multiplex detection), this can be achieved by changing the size of the quantum dot core yielding different emission wavelengths. The quantum dots can be stabilized or unstabilized as discussed above regarding nanoparticles. Preferred ligands for stabilizing quantum dots are resorcinarenes.

As a non-limiting example, quantum dots can be used where the detectable label is based on resonance energy transfer (RET). For a review of the use of quantum dots in protease assays see Kim and Kim (2012).

Viologen

In some embodiments, the detectable label comprises a viologen. As used herein, a "viologen" is an organic redox compound. Preferred viologen are able to reversibly change colour many times on oxidation and reduction. In some embodiments, the viologen is viologen methyl, propyl viologen-sulphonate or aminopropyl viologen. In some embodiments, viologen can be used as quenchers as they are able to quench the excited state of chromophores such as porphyrins.

Resonance Energy Transfer

In some embodiments, the detectable label is based on resonance energy transfer (RET), such as Förster resonance energy transfer and including, but not limited to, bioluminescent resonance energy transfer ("BRET") and fluorescence resonance energy transfer ("FRET").

As used herein, "BRET" is a proximity assay based on the non-radioactive transfer of energy between the bioluminescent protein donor and the acceptor molecule. "Bioluminescent resonance energy transfer" and "BRET" are used interchangeably.

As used herein, "FRET" is a proximity assay based on the non-radioactive transfer of energy between two chromophores or a chromophore and a quencher. "FRET" and "fluorescence resonance energy transfer" are used interchangeably.

In some embodiments, the detectable label comprises i) a chemiluminescent donor domain and an acceptor domain covalently attached to the target sequence, or ii) a donor domain and an acceptor domain. In some embodiments of ii) the donor domain is a fluorophore donor and/or the acceptor domain is a quencher domain. In some embodiments, one domain is covalently attached to the N-terminus of the target sequence and the other domain is covalently attached to the C-terminus of the target sequence. In preferred embodiments, the detectable label comprises a chemiluminescent donor domain and an acceptor domain covalently attached to the target sequence. An example is provided in FIG. 1.

A. Chemiluminescent Donor Domain

Chemiluminescence is the emission of energy with limited emission of heat (luminescence), as the result of a chemical reaction. The term "chemiluminescence" is used herein to encompass bioluminescence, which relies upon the activity of an enzyme. Non-enzymatic chemiluminescence is the result of chemical reactions between an organic dye and an oxidizing agent in the presence of a catalyst. Chemiluminescence emission occurs as the energy from the excited states of organic dyes, which are chemically induced, decays to ground state. The duration and the intensity of the chemiluminescence emission are mostly dependent on the extent of the chemical reagents present in the reaction solution.

In preferred embodiments, the chemiluminescent donor domain is a bioluminescent protein. As used herein, the term "bioluminescent protein" refers to any protein capable of acting on a suitable substrate to generate luminescence.

It is understood in the art that a bioluminescent protein is an enzyme which converts a substrate into an activated product which then releases energy as it relaxes. The activated product (generated by the activity of the bioluminescent protein on the substrate) is the source of the bioluminescent protein-generated luminescence that is transferred to the acceptor molecule.

There are a number of different bioluminescent proteins that can be employed in this invention (see, for example, Table 1). Light-emitting systems have been known and isolated from many luminescent organisms including bacteria, protozoa, coelenterates, molluscs, fish, millipedes, flies, fungi, worms, crustaceans, and beetles, particularly click beetles of genus *Pyrophorus* and the fireflies of the genera *Photinus, Photuris,* and *Luciola*. Additional organisms displaying bioluminescence are listed in WO 00/024878, WO 99/049019 and Viviani (2002).

Any suitable bioluminescent protein can be used in the sensors of the present application. One very well-known example is the class of proteins known as luciferases which catalyse an energy-yielding chemical reaction in which a specific biochemical substance, a luciferin (a naturally occurring fluorophore), is oxidized by an enzyme having a luciferase activity (Hastings, 1996). A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. Bioluminescent proteins with luciferase activity are thus available from a variety of sources or by a variety of means. Examples of bioluminescent proteins with luciferase activity may be found in U.S. Pat. Nos. 5,229,285, 5,219,737, 5,843,746, 5,196,524, and 5,670,356. Two of the most widely used luciferases are: (i) *Renilla* luciferase (from *R. reniformis*), a 35 kDa protein, which uses coelenterazine as a substrate and emits light at 480 nm (Lorenz et al., 1991); and (ii) Firefly luciferase (from *Photinus pyralis*), a 61 kDa protein, which uses luciferin as a substrate and emits light at 560 nm (de Wet et al., 1987).

*Gaussia* luciferase (from *Gaussia princeps*) has been used in biochemical assays (Verhaegen et al., 2002). *Gaussia* luciferase is a 20 kDa protein that oxidises coelenterazine in a rapid reaction resulting in a bright light emission at 470 nm.

Luciferases useful for the present invention have also been characterized from *Anachnocampa* sp (WO 2007/019634). These enzymes are about 59 kDa in size and are ATP-dependent luciferases that catalyse luminescence reactions with emission spectra within the blue portion of the spectrum.

Biologically active variants or fragments of naturally occurring bioluminescent protein can readily be produced by those skilled in the art. Three examples of such variants useful for the invention are Rluc2 (Loening et al., 2006), Rluc8 (Loening et al., 2006) and Rluc8.6-535 (Loening et al., 2007) which are each variants of *Renilla* luciferase. In a further preferred embodiment, the sequence of the BRET chemiluminescent donor is chosen to have greater thermal stability than sensor molecules incorporating native *Renilla* luciferase sensors. RLuc2 or RLuc8 are convenient examples of suitable choices, which consequently exhibit $\geq 5\times$ or $\geq 10\times$ higher luminance than sensors incorporating the native *Renilla* luciferase sequence. Such enhanced luminance has significant benefits as it permits more economical use of reagents for any given time resolution.

TABLE 1

Exemplary bioluminescent proteins.

| Species | Name | Organism | MW kDa × $10^{-3}$ | Emission (nm) | Example of Substrate |
|---|---|---|---|---|---|
| Insect | FFluc | *Photinus pyralis* (North American Firefly) | ~61 | 560 | D-(−)-2-(6'-hydroxybenzothiazolyl)-$D^2$-thiazoline-4-carboxylic acid, HBTTCA ($C_{11}H_8N_2O_3S_2$) (luciferin) |
| Insect | FF'luc | *Luciola cruciata* (Japanese Firefly) | | 560-590 (many mutants) | Luciferin |
| Insect | | *Phengodid* beetles (railroad worms) | | | |
| Insect | | *Arachnocampa* spp. | | | Luciferin |
| Insect | | *Orphelia fultoni* (North American glow worm) | | | |
| Insect | Clluc | *Pyrophorus plagiophthalamus* (click beetle) | | 546, 560, 578 and 593 | Luciferin |
| Jellyfish | Aequorin | *Aequorea* | 44.9 | 460-470 | Coelenterazine |
| Sea pansy | Rluc | *Renilla reniformis* | 36 | 480 | Coelenterazine |
| Sea pansy (modified) | Rluc8 | *Renilla reniformis* (modified) | 36 | 487 (peak) | Coelenterazine/ Deep Blue C |
| Sea pansy (modified) | Rluc2 | *Renilla reniformis* (modified M185V/Q235A) | 36 | 480 | Coelenterazine |
| Sea pansy (modified) | RLuc8.6-535 | *Renilla reniformis* (modified) | 36 | 535 | Coelenterazine |
| Sea pansy | Rmluc | *Renilla mullerei* | 36.1 | ~480 | Coelenterazine |
| Sea pansy | | *Renilla kollikeri* | | | |
| Crustacea (shrimp) | Vluc | *Vargula hilgendorfii* | ~62 | ~460 | Coelenterazine |
| Crustaeca | CLuc | *Cypridina* (sea firefly) | 75 | 465 | Coelenterazine/ *Cypridina* luciferin |
| Dinofagellate (marine alga) | | *Gonyaulax polyedra* | 130 | ~475 | Tetrapyrrole |
| Mollusc | | *Latia* (fresh water limpet) | 170 | 500 | Enol formate, terpene, aldehyde |
| Hydroid | | *Obelia biscuspidata* | ~20 | ~470 | Coelenterazine |
| Shrimp | | *Oplophorus gracilorostrisorus* | 31 | 462 | Coelenterazine |
| Shrimp | | *Oplophorus gracilorostris* (NanoLuc) | 19 | ~460 | Furimazine |
| Others | Ptluc | *Ptilosarcus* | | ~490 | Coelenterazine |
| | Gluc | *Gaussia* | ~20 | ~475 | Coelenterazine |
| | Plluc | *Pleuromamma* | 22.6 | ~475 | Coelenterazine |

Alternative, non-luciferase, bioluminescent proteins that can be employed in this invention are any enzymes which can act on suitable substrates to generate a luminescent signal. Specific examples of such enzymes are β-galactosidase, lactamase, horseradish peroxidase, alkaline phophatase, β-glucuronidase and β-glucosidase. Synthetic luminescent substrates for these enzymes are well known in the art and are commercially available from companies, such as Tropix Inc. (Bedford, MA, USA).

An example of a peroxidase useful for the present invention is described by Hushpulian et al. (2007).

In some embodiments, the bioluminescent protein is a luciferase, a β-galactosidase, a lactamase, a horseradish peroxidase, an alkaline phosphatase, a β-glucuronidase or a β-glucosidase. In some embodiments, the bioluminescent protein is luiferase. Suitable luciferase include, but are not limited to a *Renilla* luciferase, a Firefly luciferase (e.g. PpyRE8, PpyRE10), a Coelenterate luciferase, a North American glow worm luciferase, a click beetle luciferase, a railroad worm luciferase, a bacterial luciferase, a *Gaussia* luciferase, Aequorin, an *Arachnocampa* luciferase, or a biologically active variant or fragment of any one, or chimera of two or more, thereof.

As used herein, a "biologically active fragment" is a portion of a polypeptide as described herein which maintains a defined activity of the full-length polypeptide. As used herein, a "biologically active variant" is a molecule which differs from a naturally occurring and/or defined molecule by one or more amino acids but maintains a defined activity, such as defined above for biologically active fragments. Biologically active variants are typically least 50%, more preferably at least 80%, more preferably at least 90%, more preferably at least 95%, more preferably at least 97%, and even more preferably at least 99% identical to the naturally occurring and/or defined molecule.

In a preferred embodiment, a bioluminescent protein with a small molecular weight is used to prevent an inhibition of the interaction due to steric hindrance. The bioluminescent protein preferably consists of a single polypeptide chain. Also the bioluminescent proteins preferably do not form oligomers or aggregates. The bioluminescent proteins *Renilla* luciferase, *Gaussia* luciferase and Firefly luciferase meet all or most of these criteria.

As used herein, the term "substrate" refers to any molecule that can be used in conjunction with a chemiluminescent donor to generate or absorb luminescence. The choice of the substrate can impact on the wavelength and the intensity of the light generated by the chemiluminescent donor. In some embodiments, the bioluminescent protein has a substrate selected from luciferin, calcium, coelenterazine, a derivative or analogue of coelenterazine or a derivative or analogue of luciferin.

Coelenterazine is a widely known substrate which occurs in cnidarians, copepods, chaetognaths, ctenophores, decapod shrimps, mysid shrimps, radiolarians and some fish taxa (Greer and Szalay, 2002). For *Renilla* luciferase for example, coelenterazine analogues/derivatives are available that result in light emission between 418 and 547 nm (Inouye et al., 1997, Loening et al., 2007). A coelenterazine analogue/derivative (400A, DeepBlueC) has been described emitting light at 400 nm with *Renilla* luciferase (WO 01/46691). Other examples of coelenterazine analogues/derivatives are EnduRen, Prolume purple, Prolume purple II, Prolume purple III, ViviRen and Furimazine. Other examples of coelenterazine analogues/derivatives include, but are not limited to, compounds disclosed in PCT/US2013057660 and US20140302539.

As used herein, the term "luciferin" is defined broadly and refers to a class of light-emitting biological pigments found in organisms capable of bioluminescence as well as synthetic analogues or functionally equivalent chemicals, which are oxidised in the presence of the enzyme luciferase to produce oxyluciferin and energy in the form of light. D-luciferin, or 2-(6-hydroxybenzothiazol-2-yl)-2-thiazoline-4-carboxylic acid, was first isolated from the firefly *Photinus pyralis*. Since then, various chemically distinct forms of luciferin have been discovered and studied from various different organisms, mainly from the ocean, for example fish and squid, however, many have been identified in land dwelling organisms, for example, worms, beetles and various other insects (Day et al., 2004; Viviani, 2002). As used herein, luciferin also includes derivatives or analogues of luciferin.

In addition to entirely synthetic luciferin, such as cyclic alkylaminoluciferin (CycLuc1), there are at least five general types of biologically evolved luciferin, which are each chemically different and catalysed by chemically and structurally different luciferases that employ a wide range of different cofactors. First, is firefly luciferin, the substrate of firefly luciferase, which requires ATP for catalysis (EC 1.13.12.7). Second, is bacterial luciferin, also found in some squid and fish, that consists of a long chain aldehyde and a reduced riboflavin phosphate. Bacterial luciferase is FMNH-dependent. Third, is dinoflagellate luciferin, a tetrapyrrolic chlorophyll derivative found in dinoflagellates (marine plankton), the organisms responsible for night-time ocean phosphorescence. Dinoflagellate luciferase catalyses the oxidation of dinoflagellate luciferin and consists of three identical and catalytically active domains. Fourth, is the imidazolopyrazine vargulin, which is found in certain ostracods and deep-sea fish, for example, Porichthys. Last, is coelenterazine (an imidazolpyrazine), the light-emitter of the protein aequorin, found in radiolarians, ctenophores, cnidarians, squid, copepods, chaetognaths, fish and shrimp.

In some embodiments, the bioluminescent protein requires a co-factor. Examples of co-factors include, but are not necessarily limited to, ATP, magnesium, oxygen, $FMNH_2$, calcium, or a combination of any two or more thereof.

B. Acceptor Domain

As used herein, an "acceptor domain" is any molecule that is capable of accepting energy emitted as a result of the activity of a chemiluminescent donor domain. In some embodiments, the acceptor domain (also referred to herein as "acceptor molecule") is a fluorescent acceptor domain. As used herein, the term "fluorescent acceptor domain" (also referred herein to as "fluorescent acceptor molecule") refers to any compound which can accept energy emitted as a result of the activity of a chemiluminescent donor, and re-emit it as light energy.

There are a number of different acceptor domains that can be employed in this invention. Suitable acceptor domains may be a protein or non-proteinaceous.

In some embodiments, the fluorescent acceptor domain is a protein. Examples include, but are not limited to, green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, TdTomato, mCherry, Kaede protein, TagRFP, TurBoFB or a Phycobiliprotein, or a biologically active variant or fragment of any one thereof.

In some embodiments, the fluorescent acceptor domain is a non-protein. Examples of acceptor molecules that are not proteins include, but are not limited to, Alexa Fluor dye (e.g. AF680, AF750), Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

One very well-known example is the group of fluorophores that includes the green fluorescent protein from the jellyfish *Aequorea victoria* and numerous other variants (GFPs) arising from the application of molecular biology, for example mutagenesis and chimeric protein technologies (Tsien, 1998). GFPs are classified based on the distinctive component of their chromophores, each class having distinct excitation and emission wavelengths: class 1, wild-type mixture of neutral phenol and anionic phenolate: class 2, phenolate anion: class 3, neutral phenol: class 4, phenolate anion with stacked s-electron system: class 5, indole: class 6, imidazole: and class 7, phenyl.

A naturally occurring acceptor molecule which has been mutated (variants) can also be useful for the present invention. One example of an engineered system which is suitable for BRET is a *Renilla* luciferase and enhanced yellow mutant of GFP (EYFP) pairing which do not directly interact to a significant degree with one another alone in the absence of a mediating protein(s) (in this case, the G protein coupled receptor) (Xu et al., 1999).

In another embodiment, the acceptor domain is a fluorescent nanocrystal. Nanocrystals, or "quantum dots", have several advantages over organic molecules as fluorescent labels, including resistance to photodegradation, improved brightness, non-toxicity, and size dependent, narrow emission spectra that enables the monitoring of several processes simultaneously. Additionally, the absorption spectrum of nanocrystals is usually very broad, enabling all sizes, and hence all colours, to be excited with a single excitation wavelength. This property means they are suitable for multiplexing. Nanocrystals also have very large molar extinction coefficients at wavelengths in the ultraviolet and visible range. As a result they are able to absorb 10-50 times more photons than organic dyes at the same excitation flux.

Fluorescent nanocrystals may be attached, or "bioconjugated", to proteins (such as the sensors or target sequence of the present application) in a variety of ways. For example, the surface cap of a "quantum dot" may be negatively charged with carboxylate groups from either dihydrolipoic acid (DHLA) or an amphiphilic polymer. Proteins can be conjugated to the DHLA-nanocrystals electrostatically, either directly or via a bridge consisting of a positively charged leucine zipper peptide fused to recombinant protein. The latter binds to a primary antibody with specificity for the intended target. Alternatively, antibodies, streptavidin, or other proteins are coupled covalently to the polyacrylate cap of the nanocrystal with conventional carbodiimide chemistry.

There are colloidal methods to produce nanocrystals, including cadmium selenide, cadmium sulfide, indium arsenide, and indium phosphide. These quantum dots can contain as few as 100 to 100,000 atoms within the quantum dot volume, with a diameter of 10 to 50 atoms. Some quantum dots are small regions of one material buried in another with a larger band gap. These can be so-called core-shell structures, for example, with CdSe in the core and ZnS in the shell or from special forms of silica called ormosil. The larger the dot, the redder (lower energy) its fluorescence spectrum. Conversely, smaller dots emit bluer (higher energy) light. The colouration is directly related to the energy levels of the quantum dot. Quantitatively speaking, the bandgap energy that determines the energy (and hence colour) of the fluoresced light is inversely proportional to the square of the size of the quantum dot. Larger quantum dots have more energy levels which are more closely spaced. This allows the quantum dot to absorb photons containing less energy, i.e. those closer to the red end of the spectrum.

A mentioned previously, nanocrystals can be coated with organic molecules and/or macromolecules. These coatings can be used to alter the properties of the nanocrystal. For example, the coatings can improve the solubility of the nanocrystal in an aqueous solvent.

The application of nanocrystals or quantam dots to FRET and BRET is reviewed in Kim and Kim (2012).

In an alternate embodiment, the acceptor molecule is a fluorescent microsphere. These are typically made from polymers, and contain fluorescent molecules (for example fluorescein GFP or YFP) incorporated into the polymer matrix, which can be conjugated to a variety of reagents. Fluorescent microspheres may be labelled internally or on the surface. Internal labelling produces very bright and stable particles with typically narrow fluorescent emission spectra. With internal labelling, surface groups remain available for conjugating ligands (for example, proteins) to the surface of the bead. Internally-labelled beads are used extensively in imaging applications, as they display a greater resistance to photobleaching.

Carboxylate-modified fluorescent microspheres are suitable for covalent coupling of proteins using water-soluble carbodiimide reagents such as 1-ethyl-3-(3-dimethylaminopropyl) carbodiimide hydrochloride (EDAC). Sulfate fluorescent microspheres are relatively hydrophobic and will passively and nearly irreversibly adsorb almost any protein. Aldehyde-sulfate fluorescent microspheres are sulfate microspheres that have been modified to add surface aldehyde groups, and react with proteins.

In another embodiment, the acceptor molecule is a luminescent microsphere. These are typically made from polymers, which contain luminescent molecules (for example complexes of europium or platinum) incorporated into the polymer matrix, which can be conjugated to a variety of reagents.

Examples of non-fluorescent acceptor domains useful for the invention include quenchers such as DABCYL [4-((4-(Dimethylamino) phenyl)azo)benzoic acid], DAB SYL (Dimethylaminoazosulfonic acid), metal nanoparticles such as gold and silver, black hole quenchers (BHQ) and QXL quenchers.

C. Chemiluminescent Donor Domain and Acceptor Domain Pairs

Any number of donor-acceptor combinations can be used in the sensors of the present invention. A worker skilled in the art would be able to select a donor and acceptor pair which permits efficient energy transfer. In preferred embodiments, the separation and relative orientation of the chemiluminescent donor domain and the acceptor domain in the absence of the *Pseudomonas* spp. protease is within ±50% of the Förster distance. As used herein, the term "the separation and relative orientation of the chemiluminescent donor domain and the acceptor domain, in the presence and/or absence of analyte, is within ±50% of the Forster distance" refers to the steady state RET measurements which can be carried out within a range of ±50% of $R_0$. This phrase encompasses an efficiency of luminescence energy transfer from the chemiluminescent donor domain to the acceptor domain in the range of 10-90%. In some embodiments, the Förster distance of the chemiluminescent donor domain and the acceptor domain is at least 4 nm. In an embodiment, the Förster distance of the chemiluminescent donor domain and the acceptor domain is between about 4 nm and about 10 nm, or is between about 6 nm and about 10 nm.

A criterion which should be considered in determining suitable pairings is the relative emission/fluorescence spectrum of the acceptor molecule compared to that of the donor. The emission spectrum of the donor should overlap with the absorbance spectrum of the acceptor molecule such that the light energy from the donor luminescence emission is at a wavelength that is able to excite the acceptor molecule and thereby promote acceptor molecule fluorescence when the two molecules are in a proper proximity and orientation with respect to one another. For example, it has been demonstrated that a *Renilla* luciferase/EGFP pairing is not as good as a *Renilla* luciferase/EYEF pairing based on observable emission spectral peaks (Xu, 1999; Wang et al., 1997). To study potential pairing, protein fusions (for example) are prepared containing the selected bioluminescent protein and acceptor molecule and are tested, in the presence of an appropriate substrate.

It should also be confirmed that the donor and acceptor molecule do not spuriously associate with each other. This can be accomplished by, for example, separate co-expression of a bioluminescent protein and acceptor molecule in the same cells and then monitoring the luminescence spectrum in order to determine if BRET occurs. This may be achieved, for example, using the method of Xu et al. (1999). The selected bioluminescent protein and acceptor molecule form a suitable BRET pair if little or no BRET is observed.

The donor emission can be manipulated by modifications to the substrate. In the case of *Renilla* luciferases the substrate is coelenterazine. The rationale behind altering the donor emission is to improve the resolution between donor emission and acceptor emissions. The original BRET system uses the *Renilla* luciferase as donor, EYFP (or Topaz) as the acceptor and coelenterazine h derivative as the substrate. These components when combined in a BRET assay, generate light in the 475-480 nm range for the bioluminescent protein and the 525-530 nm range for the acceptor molecule, giving a spectral resolution of 45-55 nm.

Unfortunately, *Renilla* luciferase generates a broad emission peak overlapping substantially the GFP emission, which in turn contributes to decrease the signal to noise of the system. One BRET system for use in the present invention has coe1400a as the *Renilla* luciferase substrate and provides broad spectral resolution between donor and acceptor emission wavelengths (~105 nm). *Renilla* luciferase with coe1400a generates light between 390-400 nm and a GFP derivative (GFP) was prepared which absorbs light in this range and re-emits light at 505-508 nm. Because of this increase in spectral resolution between *Renilla* luciferase and GFP emissions, this BRET system provides an excellent biological tool to monitor cleavage of the target sequence be a bacterial protease. However, smaller Stokes shift BRET systems would also allow sensitive measurement of protease activity.

Various coelenterazine derivatives are known in the art, including coe1400a, that generate light at various wavelengths (distinct from that generated by the wild type coelenterazine) as a result of *Renilla* luciferase activity. A worker skilled in the art would appreciate that because the light emission peak of the donor has changed, it is necessary to select an acceptor molecule which will absorb light at this wavelength and thereby permit efficient energy transfer. This can be done, for example by altering a GFP class 4 such that it becomes a class 3 or 1 GFP. Spectral overlapping between light emission of the donor and the light absorption peak of the acceptor is one condition among others for an efficient energy transfer. Class 3 and 1 GFPs are known to absorb light at 400 nm and re-emit between 505-511 nm. This results in a wavelength difference between donor and acceptor emissions of approximately 111 nm.

Examples of further bioluminescent protein and acceptor molecule pairs are provided in Table 2.

TABLE 2

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| Rluc2 Rluc8 | Native coelenterazine | 470 nm | Venus | 515/528 nm |
| Rluc2 Rluc8 | Native coelenterazine | 470 nm | mOrange | 548/562 nm |
| Rluc2 Rluc8 | Native Coelenterazine | 470 nm | EYFP/Topaz | 514/527 nm |
| Rluc2 Rluc8 | Native Coelenterazine | 470 nm | mCitrine | 516/529 nm |
| Rluc Rluc2 Rluc8 | Native Coelenterazine | 470 nm | YPet | 517/530 nm |
| Rluc2 Rluc8 | Native Coelenterazine | 470 nm | Fluorescein | 495/519 nm |
| Rluc2 Rluc8 | Native Coelenterazine | 470 nm | Acridine yellow | 470/550 nm |
| Rluc2 Rluc8 | Native Coelenterazine | 470 nm | Nile red | 485/525 nm |
| Rluc2 Rluc8 | Native Coelenterazine | 470 nm | R-Phycoerythrin | 480/578 nm |
| Rluc2 Rluc8 | Native Coelenterazine | 470 nm | Red 613 | 480/613 nm |
| Rluc2 Rluc8 | Native Coelenterazine | 470 nm | TruRed | 490/695 nm |
| RLuc8.6-5.35 | Native Coelenterazine | 535 nm | mOrange | 548/562 nm |
| RLuc8.6-5.35 | Coelenterazine h | 535 nm | TagRFP | 555/584 nm |
| RLuc8.6-5.35 | Coelenterazine h | 535 nm | TurboRFP | 588/635 nm |
| Rluc Rluc2 Rluc8 | Coelenterazine v | 515 nm | mOrange | 548/562 nm |
| Rluc Rluc2 Rluc8 | Coelenterazine v | 515 nm | TagRFP | 555/584 nm |
| RLuc8.6-5.35 | Coelenterazine v | 570 nm | TurboRFP | 588/635 nm |
| Rluc2 Rluc8 | Coelenterazine h | 470 nm | Venus | 515/528 nm |
| Rluc2 Rluc8 | Coelenterazine h | 470 nm | mOrange | 548/528 nm |
| Rluc2 Rluc8 | Coelenterazine h | 470 nm | EYFP/Topaz | 514/527 nm |
| Rluc2 Rluc8 | Coelenterazine h | 470 nm | mCitrine | 516/529 nm |
| Rluc2 Rluc8 | Native Coelenterazine | 470 nm | YPet | 517/530 nm |

TABLE 2-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| Rluc Rluc2 Rluc8 | Coelenterazine h | 470 nm | Fluorescein | 490/525 nm |
| Rluc Rluc2 Rluc8 | Coelenterazine h | 470 nm | Acridine yellow | 470/550 nm |
| Rluc Rluc2 Rluc8 | Coelenterazine h | 470 nm | Nile red | 485/525 nm |
| Rluc Rluc2 Rluc8 | Coelenterazine h | 470 nm | R-Phycoerythrin | 480/578 nm |
| Rluc Rluc2 Rluc8 | Coelenterazine h | 470 nm | Red 613 | 480/613 nm |
| Rluc Rluc2 Rluc8 | Coelenterazine h | 470 nm | TruRed | 490/695 nm |
| RLuc8.6-5.35 | Coelenterazine h | 535 nm | mOrange | 548/562 nm |
| Rluc Rluc2 Rluc8 | Coelenterazine 400a | 400 nm | GFP2 | 396/508 nm |
| Rluc Rluc2 Rluc8 | Coelenterazine 400a | 400 nm | GFP10 | 400/510 nm |
| Rluc Rluc2 Rluc8 | Coelenterazine 400a | 400 nm | Wild type GFP | 396 (475)/508 nm |
| Rluc Rluc2 Rluc8 | Coelenterazine 400a | 400 nm | TagBFP | 402/457 nm |
| Rluc Rluc2 Rluc8 | Coelenterazine 400a | 400 nm | Cerulean/mCFP | 433/475 nm |
| Rluc Rluc2 Rluc8 | Coelenterazine 400a | 400 nm | ECFP/CyPet | 434/477 nm |
| Rluc Rluc2 Rluc8 | Coelenterazine 400a | 400 nm | Y66W | 436/485 nm |
| Rluc Rluc2 Rluc8 | Coelenterazine 400a | 400 nm | dKeima-Red | 440/616 nm |
| Rluc Rluc2 Rluc8 | Coelenterazine 400a | 400 nm | mKeima-Red | 440/620 nm |
| Rluc Rluc2 Rluc8 | Coelenterazine 400a | 400 nm | Quin-2 | 365/490 nm |
| Rluc Rluc2 Rluc8 | Coelenterazine 400a | 400 nm | Pacific blue | 403/551 nm |
| Rluc Rluc2 Rluc8 | Coelenterazine 400 | 400 nm | Dansychloride | 380/475 nm |
| Firefly luciferase | Luciferin | 560 nm | Cyanine Cy3 | 575/605 nm |
| Firefly luciferase | Luciferin | 560 nm | Texas red | 590/615 nm |
| Firefly luciferase | Luciferin | 560 nm | TurboRed | 553/574 nm |
| Firefly luciferase | Luciferin | 560 nm | tdTomato | 554/581 nm |
| Firefly luciferase | Luciferin | 560 nm | TagRFP | 555/584 nm |
| Firefly luciferase | Luciferin | 560 nm | DsRed | 557/592 nm |
| Firefly luciferase | Luciferin | 560 nm | mRFP1 | 584/607 nm |
| Firefly luciferase | Luciferin | 560 nm | mCherry | 587/610 nm |
| Beetle green luciferase | Luciferin | 560 nm | tdTomato | 554/581 nm |

TABLE 2-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| FFLuc PpyRE8 PpyRE10 | Luciferin | 560 nm | AF680 | 679/702 nm |
| FFLuc PpyRE8 PpyRE10 | Luciferin | 560 nm | AF750 | 749/775 nm |
| NanoLuc | Furimazine | 460 nm | Venus | 515/528 nm |
| NanoLuc | Furimazine | 460 nm | mOrange | 548/562 nm |
| NanoLuc | Furimazine | 460 nm | EYFP/Topaz | 514/527 nm |
| NanoLuc | Furimazine | 460 nm | mCitrine | 516/529 nm |
| NanoLuc | Furimazine | 460 nm | YPet | 517/530 nm |
| NanoLuc | Furimazine | 460 nm | Fluorescein | 495/519 nm |
| NanoLuc | Furimazine | 460 nm | Acridine yellow | 470/550 nm |
| NanoLuc | Furimazine | 460 nm | Nile red | 485/525 nm |
| NanoLuc | Furimazine | 460 nm | R-Phycoerythrin | 480/487 nm |
| NanoLuc | Furimazine | 460 nm | Red 613 | 480/613 nm |
| NanoLuc | Furimazine | 460 nm | TruRed | 490/695 nm |
| NanoLuc | Furimazine | 460 nm | Oregon Green | 496/516 nm |
| NanoLuc | Furimazine | 460 nm | diAcFAM | 494/526 nm |
| NanoLuc | Furimazine | 460 nm | AlexFluor488 | 494/517 nm |
| NanoLuc | Furimazine | 460 nm | TMR | 555/585 nm |
| NanoLuc | Furimazine | 460 nm | Halotag NCT | 595/635 nm |
| NanoLuc | Furimazine | 460 nm | HalotagBRET 618 | 525/618 nm |
| NanoLuc | Native Coelenterazine | 460 nm | Venus | 515/528 nm |
| NanoLuc | Native Coelenterazine | 460 nm | mOrange | 548/562 nm |
| NanoLuc | Native Coelenterazine | 460 nm | EYFP/Topaz | 514/527 nm |
| NanoLuc | Native Coelenterazine | 460 nm | mCitrine | 516/529 nm |
| NanoLuc | Native Coelenterazine | 460 nm | YPet | 517/530 nm |
| NanoLuc | Native Coelenterazine | 460 nm | Fluorescein | 495/519 nm |
| NanoLuc | Native Coelenterazine | 460 nm | Acridine yellow | 470/550 nm |
| NanoLuc | Native Coelenterazine | 460 nm | Nile red | 485/525 nm |
| NanoLuc | Native Coelenterazine | 460 nm | R-Phycoerythrin | 480/487 nm |
| NanoLuc | Native Coelenterazine | 460 nm | Red 613 | 480/613 nm |
| NanoLuc | Native Coelenterazine | 460 nm | TruRed | 490/695 nm |
| NanoLuc | Native Coelenterazine | 460 nm | Oregon Green | 496/516 nm |
| NanoLuc | Native Coelenterazine | 460 nm | diAcFAM | 494/526 nm |
| NanoLuc | Native Coelenterazine | 460 nm | AlexFluor488 | 494/517 nm |
| NanoLuc | Native Coelenterazine | 460 nm | TMR | 555/585 nm |
| NanoLuc | Native Coelenterazine | 460 nm | Halotag NCT | 595/635 nm |
| NanoLuc | Native Coelenterazine | 460 nm | HalotagBRET 618 | 525/618 |
| NanoLuc | Native Coelenterazine | 460 nm | Oregon Green | 496/516 nm |
| NanoLuc | Native Coelenterazine | 460 nm | diAcFAM | 494/526 nm |
| NanoLuc | Native Coelenterazine | 460 nm | AlexFluor488 | 494/517 nm |
| NanoLuc | Native Coelenterazine | 460 nm | TMR | 555/585 nm |
| NanoLuc | Native Coelenterazine | 460 nm | Halotag NCT | 595/635 nm |
| NanoLuc | Native Coelenterazine | 460 nm | HalotagBRET 618 | 525/618 |
| NanoLuc | Coelenterazine h | 460 nm | Venus | 515/528 nm |
| NanoLuc | Coelenterazine h | 460 nm | mOrange | 548/562 nm |
| NanoLuc | Coelenterazine h | 460 nm | EYFP/Topaz | 514/527 nm |
| NanoLuc | Coelenterazine h | 460 nm | mCitrine | 516/529 nm |

TABLE 2-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| NanoLuc | Coelenterazine h | 460 nm | YPet | 517/530 nm |
| NanoLuc | Coelenterazine h | 460 nm | Fluorescein | 495/519 nm |
| NanoLuc | Coelenterazine h | 460 nm | Acridine yellow | 470/550 nm |
| NanoLuc | Coelenterazine h | 460 nm | Nile red | 485/525 nm |
| NanoLuc | Coelenterazine h | 460 nm | R-Phycoerythrin | 480/487 nm |
| NanoLuc | Coelenterazine h | 460 nm | Red 613 | 480/613 nm |
| NanoLuc | Coelenterazine h | 460 nm | TruRed | 490/695 nm |
| NanoLuc | Coelenterazine h | 460 nm | Oregon Green | 496/516 nm |
| NanoLuc | Coelenterazine h | 460 nm | diAcFAM | 494/526 nm |
| NanoLuc | Coelenterazine h | 460 nm | AlexFluor488 | 494/517 nm |
| NanoLuc | Coelenterazine h | 460 nm | TMR | 555/585 nm |
| NanoLuc | Coelenterazine h | 460 nm | Halotag NCT | 595/635 nm |
| NanoLuc | Coelenterazine h | 460 nm | HalotagBRET 618 | 525/618 |
| Rluc Rluc2 Rluc8 | Prolume Purple Substrate | 405 nm | GFP2 | 396/508 nm |
| Rluc Rluc2 Rluc8 | Prolume Purple Substrate | 405 nm | GFP 10 | 400/510 nm |
| Rluc Rluc2 Rluc8 | Prolume Purple Substrate | 405 nm | Wild type GFP | 396 (475)/508 nm |
| Rluc Rluc2 Rluc8 | Prolume Purple Substrate | 405 nm | TagBFP | 402/457 nm |
| Rluc Rluc2 Rluc8 | Prolume Purple Substrate | 405 nm | Cerulean/mCFP | 433/475 nm |
| Rluc Rluc2 Rluc8 | Prolume Purple Substrate | 405 nm | ECFP/CyPet | 434/477 nm |
| Rluc Rluc2 Rluc8 | Prolume Purple Substrate | 405 nm | Y66W | 436/485 nm |
| Rluc Rluc2 Rluc8 | Prolume Purple Substrate | 405 nm | dKeima-Red | 440/616 nm |
| Rluc Rluc2 Rluc8 | Prolume Purple Substrate | 405 nm | mKeima-Red | 440/620 nm |
| Rluc Rluc2 Rluc8 | Prolume Purple Substrate | 405 nm | Quin-2 | 365/490 nm |
| Rluc Rluc2 Rluc8 | Prolume Purple Substrate | 405 nm | Pacific blue | 403/551 nm |
| Rluc Rluc2 Rluc8 | Prolume Purple Substrate | 405 nm | Dansychloride | 380/475 nm |
| Rluc Rluc2 Rluc8 | Prolume Purple Substrate II | 400 nm | GFP2 | 396/508 nm |
| Rluc Rluc2 Rluc8 | Prolume Purple Substrate II | 400 nm | GFP10 | 400/510 nm |
| Rluc Rluc2 Rluc8 | Prolume Purple Substrate II | 400 nm | Wild type GFP | 396 (475)/508 nm |
| Rluc Rluc2 Rluc8 | Prolume Purple Substrate II | 400 nm | TagBFP | 402/457 nm |
| Rluc Rluc2 Rluc8 | Prolume Purple Substrate II | 400 nm | Cerulean/mCFP | 433/475 nm |
| Rluc Rluc2 Rluc8 | Prolume Purple Substrate II | 400 nm | ECFP/CyPet | 434/477 nm |
| Rluc Rluc2 Rluc8 | Prolume Purple Substrate II | 400 nm | Y66W | 436/485 nm |
| Rluc Rluc2 Rluc8 | Prolume Purple Substrate II | 400 nm | dKeima-Red | 440/616 nm |

TABLE 2-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| Rluc Rluc2 Rluc8 | Prolume Purple Substrate II | 400 nm | mKeima-Red | 440/620 nm |
| Rluc Rluc2 Rluc8 | Prolume Purple Substrate II | 400 nm | Quin-2 | 365/490 nm |
| Rluc Rluc2 Rluc8 | Prolume Purple Substrate II | 400 nm | Pacific blue | 403/551 nm |
| Rluc Rluc2 Rluc8 | Prolume Purple Substrate II | 400 nm | Dansychloride | 380/475 nm |
| Rluc Rluc2 Rluc8 | Prolume Purple Substrate III | 410 nm | GFP2 | 396/508 nm |
| Rluc Rluc2 Rluc8 | Prolume Purple Substrate III | 410 nm | GFP10 | 400/510 nm |
| Rluc Rluc2 Rluc8 | Prolume Purple Substrate III | 410 nm | Wild type GFP | 396 (475)/508 nm |
| Rluc Rluc2 Rluc8 | Prolume Purple Substrate III | 410 nm | TagBFP | 402/457 nm |
| Rluc Rluc2 Rluc8 | Prolume Purple Substrate III | 410 nm | Cerulean/mCFP | 433/475 nm |
| Rluc Rluc2 Rluc8 | Prolume Purple Substrate III | 410 nm | ECFP/CyPet | 434/477 nm |
| Rluc Rluc2 Rluc8 | Prolume Purple Substrate III | 410 nm | Y66W | 436/485 nm |
| Rluc Rluc2 Rluc8 | Prolume Purple Substrate III | 410 nm | dKeima-Red | 440/616 nm |
| Rluc Rluc2 Rluc8 | Prolume Purple Substrate III | 410 nm | mKeima-Red | 440/620 nm |
| Rluc Rluc2 Rluc8 | Prolume Purple Substrate III | 410 nm | Quin-2 | 365/490 nm |
| Rluc Rluc2 Rluc8 | Prolume Purple Substrate III | 410 nm | Pacific blue | 403/551 nm |
| Rluc Rluc2 Rluc8 | Prolume Purple Substrate III | 410 nm | Dansychloride | 380/475 nm |

D. Fluorophore Domain and Acceptor Domain

In some embodiments, the detectable label comprises a fluorophore donor domain and an acceptor domain. As used herein, the term "donor" means a molecule that, when irradiated with light of a certain wavelength, emits light. The term "acceptor," as used herein, refers to a molecule that can absorb energy from, and upon excitation of, a donor. Both the donor and acceptor can absorb light energy, but only the donor is required to emit light energy, i.e., the donor can be fluorescent and the acceptor can be non-fluorescent. If the acceptor does not emit light energy it is referred to as a quencher or quencher domain. An acceptor useful in the invention generally also has rather low absorption at a wavelength suitable for excitation of the donor. In preferred embodiments, the detectable label comprises a fluorescent donor and quencher domain.

Any appropriately selected chromophores can be used as the donor and/or acceptor, provided that the emission spectrum of the donor overlaps with the excitation spectrum of the acceptor. As used herein, the term "overlapping" in reference to the absorbance spectrum of an acceptor and the emission spectrum of a donor, means an absorbance spectrum and emission spectrum that are partly or entirely shared. Thus, in such overlapping spectra, the high end of the range of the donor's emission spectrum is higher than the low end of the range of the acceptor's absorbance spectrum.

Non-limiting examples of fluorophores that are suitable for use as the donor and/or acceptor include, but are not limited to, fluorescein, rhodamine, 4-nitrobenzo-2-oxa-1,3-diazole (NBD); cascade blue, 4,4-difluoro-5,7-diphenyl-4-bora-3a,4a-diaza-s-indacene-3-propionic acid; 4,4-difluoro-5,p-methoxyphenyl-4-bora-3a,4a-diaza-s-indacene-3-propionic acid; 4,4-difluoro-5-styryl-4-bora-3a,4a-diaza-s-indacene-propionic acid; 6-carboxy-X-rhodamine, N,N,N',N'-tetramethyl-6-carboxyrhodamine; iodoacetyl-directed probes such as 5-((((2-iodoacetyl)amino)ethyl)amino)naphthalene-1-sulfonic acid (IAEDANS, used interchangeably with AEDANS); 5-carboxyfluorescein; 6-carboxyfluorescein; 6-(fluorescein-5-carboxamide)hexanoic acid; fluorescein isothiocyanate (FITC); tetramethylrhodamine isothiocyanate (TRITC); Texas Red (TR); eosin; a phycobiliprotein; cyanine dye; coumarin, R-phycoerythrin; allophycoerythrin (APC); a R-phycoerythrin (R-PE) conjugate; a Alexa Fluor dye; a quantum dot dye; maleimide-directed probes such as 4-dimethylaminoazobenzne-4'-maleimide (DABmal) and fluorescein-5-maleimide (Fmal); or a combination thereof (e.g., tandem conjugates).

Other non-limiting examples include nucleotide analogs such as ATP-, ADP- or AMP-analogs (see, e.g., Bagshaw, 2001). In certain embodiments, the nucleotide analogs are fluorescent. Examples of fluorescent nucleotide analogs include, by way of illustration, 2'-(or-3')-O-(trinitrophenyl)adenosine 5'-triphosphate (TNT-ATP), 2"-(or-3')-O-(trinitrophenyl)adenosine 5'-diphosphate (TNP-ADP), e-ATP, e-aza-ATP, FTP, 2AP-TP, ant-ATP, Mant-ATP, DEDA-ATP, FEDA-ATP, REDA-ATP and Cys3-EDA-ATP.

Other non-limiting examples include proteins such as green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, TdTomato, mCherry, Kaede protein, TagRFP, TurBoFB or a Phycobiliprotein, or a biologically active variant or fragment of any one thereof.

In some embodiments, the donor fluorophore domain can be a nanocrystal or quantum dot as defined above.

In some embodiments, the acceptor domain can be a quencher. As used herein, the term "quenching" refers to a decrease in fluorescence of a fluorescent donor caused by a quencher domain by energy transfer, regardless of the mechanism. Hence, illumination of the fluorescent donor in the presence of the quencher leads to an emission signal that is less intense than expected, or even completely absent. Any appropriately selected molecule can be used as the quencher provided it decreases the fluorescent intensity of the fluorophore that is being used as the fluorophore donor domain. Examples of quenchers include, but are not limited to, Deep Dark Quencher DDQ-I, DABCYL, Eclipse® Dark quencher, Iowa Black® FQ, BHQ-1, QSY-7, BHQ-2, DDQ-II, Iowa Black® RQ, QSY-21, Black Hole Quencher® BHQ-3, and gold nanoparticles.

Any number of donor-acceptor combinations can be used in the sensors of the present invention. A worker skilled in the art would be able to select a donor and acceptor pair which permits efficient energy transfer, for examples see Bryce et al. (2016) and Sapsford et al. (2006).

Detectable Change

Cleavage of the sensor of the present invention by a protease, for example a *Pseudomonas* spp. protease, produces a detectable change. As the person skilled in the art would be aware, the sensors of the present invention may also be cleaved by other proteases provided the sensor contains a cleavage site recognised and cleaved by the other protease.

As the person skilled in the art would understand a "detectable change" as used herein is any measurable change in the sensor. For example, a detectable change can be a change in a physical or chemical property of the sensor. In some embodiments, the detectable change is a change in acoustics, electrochemical potential, fluorescence, chemiluminescence, phosphorescence, absorbance, antibody binding, BRET ratio, FRET efficiency or mass. In some embodiments the detectable change is a change in fluorescence, chemiluminescence, phosphorescence, absorbance, antibody binding or mass. An advantage of the present invention is that the sensors can be adapted to suit the detection technology available. The detectable change can be measured using any technique known to the person skilled in the art.

In a preferred embodiment, the detectable change is a change in the BRET ratio. Using BRET as an example, in an embodiment the energy transfer occurring between the bioluminescent protein and acceptor molecule is presented as calculated ratios from the emissions measured using optical filters (one for the acceptor molecule emission and the other for the bioluminescent protein emission) that select specific wavelengths (see equation 1).

$$Ea/Ed = \text{BRET ratio} \quad (1)$$

where Ea is defined as the acceptor molecule emission intensity (emission light is selected using a specific filter adapted for the emission of the acceptor) and Ed is defined as the bioluminescent protein emission intensity (emission light is selected using a specific filter adapted for the emission of the bioluminescent protein).

It should be readily appreciated by those skilled in the art that the optical filters may be any type of filter that permits wavelength discrimination suitable for BRET. For example, optical filters used in accordance with the present invention can be interference filters, long pass filters, short pass filters, etc. Intensities (usually in counts per second (CPS) or relative luminescence units (RLU)) of the wavelengths passing through filters can be quantified using either a solid state micro-photomultiplier (micro-PMT), photo-multiplier tube (PMT), photodiode, including a cascade photodiode, photodiode array or a sensitive camera such as a charge coupled device (CCD) camera. The quantified signals are subsequently used to calculate BRET ratios and represent energy transfer efficiency. The BRET ratio increases with increasing intensity of the acceptor emission.

Generally, a ratio of the acceptor emission intensity over the donor emission intensity is determined (see equation 1), which is a number expressed in arbitrary units that reflects energy transfer efficiency. The ratio increases with an increase of energy transfer efficiency (see Xu et al., 1999).

Energy transfer efficiencies can also be represented using the inverse ratio of donor emission intensity over acceptor emission intensity (see equation 2). In this case, ratios decrease with increasing energy transfer efficiency. Prior to performing this calculation the emission intensities are corrected for the presence of background light and autoluminescence of the substrate. This correction is generally made by subtracting the emission intensity, measured at the appropriate wavelength, from a control sample containing the substrate but no bioluminescent protein, acceptor molecule or polypeptide of the invention.

$$Ed/Ea = \text{BRET ratio} \quad (2)$$

where Ea and Ed are as defined above.

The light intensity of the bioluminescent protein and acceptor molecule emission can also be quantified using a monochromator-based instrument such as a spectrofluorometer, a charged coupled device (CCD) camera or a diode array detector. Using a spectrofluorometer, the emission scan is performed such that both bioluminescent protein and acceptor molecule emission peaks are detected upon addition of the substrate. The areas under the peaks or the intensities at $\lambda_{MAX}$ or at wavelengths defined by any arbitrary intensity percentage relative to the maximum intensity can be used to represent the relative light intensities and may be used to calculate the ratios, as outlined above. Any instrument capable of measuring lights for the bioluminescent protein and acceptor molecule from the same sample can be used to monitor the BRET system of the present invention.

In an alternative embodiment, the acceptor molecule emission alone is suitable for effective detection and/or quantification of BRET. In this case, the energy transfer efficiency is represented using only the acceptor emission intensity. It would be readily apparent to one skilled in the art that in order to measure energy transfer, one can use the acceptor emission intensity without making any ratio calculation. This is due to the fact that ideally the acceptor molecule will emit light only if it absorbs the light transferred from the bioluminescent protein. In this case only one light filter is necessary.

In a related embodiment, the bioluminescent protein emission alone is suitable for effective detection and/or quantification of BRET. In this case, the energy transfer efficiency is calculated using only the bioluminescent protein emission intensity. It would be readily apparent to one skilled in the art that in order to measure energy transfer, one can use the donor emission intensity without making any ratio calculation. This is due to the fact that as the acceptor molecule absorbs the light transferred from the bioluminescent protein there is a corresponding decrease in detectable emission from the bioluminescent protein. In this case only one light filter is necessary.

In an alternative embodiment, the energy transfer efficiency is represented using a ratiometric measurement which only requires one optical filter for the measurement. In this case, light intensity for the donor or the acceptor is determined using the appropriate optical filter and another measurement of the samples is made without the use of any filter (intensity of the open spectrum). In this latter measurement, total light output (for all wavelengths) is quantified. Ratio calculations are then made using either equation 3 or 4. For the equation 3, only the optical filter for the acceptor is required. For the equation 4, only the optical filter for the donor is required.

$$Ea/Eo-Ea=\text{BRET ratio or }=Eo-Ea/Ea \qquad (3)$$

$$Eo-Ed/Ed=\text{BRET ratio or }=Ed/Eo-Ed \qquad (4)$$

where Ea and Ed are as defined above and Eo is defined as the emission intensity for all wavelengths combined (open spectrum).

It should be readily apparent to one skilled in the art that further equations can be derived from equations 1 through 4. For example, one such derivative involves correcting for background light present at the emission wavelength for bioluminescent protein and/or acceptor molecule.

In performing a BRET assay, light emissions can be determined from each well using the BRETCount. The BRETCount instrument is a modified TopCount, wherein the TopCount is a microtiterplate scintillation and luminescence counter sold by Packard Instrument (Meriden, CT). Unlike classical counters which utilise two photomultiplier tubes (PMTs) in coincidence to eliminate background noise, Top-Count employs single-PMT technology and time-resolved pulse counting for noise reduction to allow counting in standard opaque microtiter plates. The use of opaque microtiterplates can reduce optical crosstalk to negligible level. TopCount comes in various formats, including 1, 2, 6 and 12 detectors (PMTs), which allow simultaneous reading of 1, 2, 6 or 12 samples, respectively. Beside the BRETCount, other commercially available instruments are capable of performing BRET: the Victor 2 (Wallac, Finland (Perkin Elmer Life Sciences)) and the Fusion (Packard Instrument, Meriden). BRET can be performed using readers that can detect at least the acceptor molecule emission and preferably two wavelengths (for the acceptor molecule and the bioluminescent protein) or more.

As the person skilled in the art would understand, BRET requires that the sensor comprise a detectable label having a chemiluminescent donor domain relative to the acceptor domain. In these embodiments, the spatial location and/or dipole orientation of the chemiluminescent donor domain relative to the acceptor domain is altered when the target sequence is cleaved by a *Pseudomonas* spp. protease resulting in a change in the BRET ratio.

As used herein, the term "spatial location" refers to the three dimensional positioning of the donor relative to the acceptor molecule which changes as a result of the protease cleaving the sensor molecule, such that the donor domain is no longer linked to the acceptor domain via the target sequence.

As used herein, the term "dipole orientation" refers to the direction in three-dimensional space of the dipole moment associated either with the donor and/or the acceptor molecule relative their orientation in three-dimensional space. The dipole moment is a consequence of a variation in electrical charge over a molecule.

Cleavage of the target sequence by a *Pseudomonas* spp. protease results in a change in BRET ratio, for example, cleavage of the target sequence by a *Pseudomonas* spp. protease can result in a change in BRET ratio between about 2% to about 95% of the maximum observed BRET ratio. In some embodiments, the change in BRET ratio is between about 5% to about 90%, about 15% to about 50%, or about 15% to about 40%, of the maximum observed BRET ratio. In some embodiments, cleavage of the target sequence by a *Pseudomonas* spp. protease results in a change in BRET ratio which is ≥2% of the maximum observed BRET ratio. In some embodiments, cleavage of the target sequence by a *Pseudomonas* spp. protease results in a change in BRET ratio which is ≥5%, ≥10%, ≥20%, ≥30%, ≥35% of the maximum observed BRET ratio. A change in the BRET ratio of 15% or more increases the signal to noise ratio of protease detection. This results in a superior limit of detection for any given sampling time and more precise coding of the level of concentration of protease. Alternatively, at a fixed limit of detection, the greater change in BRET ratio facilitates shorter signal integration times and therefore more rapid detection.

As used herein, "Stokes shift" is the difference in wavelength between positions of the band maxima of the absorption and emission spectra of the same electronic transition. Preferably, the acceptor domain has a large Stokes shift. A large Stokes shift is desirable because a large difference between the positions of the band maxima of the absorption and emission spectra makes it easier to eliminate the reflected excitation radiation from the emitted signal.

In some embodiments, the acceptor domain has a Stokes Shift of greater than about 50 nm. In some embodiments, the acceptor domain has a Stokes Shift of between about 50 nm and about 350 nm, between about 50 nm and about 150 nm. In some embodiments, the acceptor domain has a Stokes Shift of greater than about 90 nm, for example 100 nm, 110 nm, 120 nm, 130 nm, 140 nm or 150 nm.

BRET has several advantages over fluorescence based technologies because it does not require excitation of the donor with an external light source. BRET does not suffer from autofluorescence, light scattering, photobleaching and/or photoisomerization of the donor moiety or photodamage to cells. The absence of an external light source in BRET assays results in a very low background and consequently increased detection sensitivity. For example, BRET is 50 times more sensitive than FRET for monitoring thrombin-catalysed proteolytic cleavage (Dacres et al., 2009).

In some embodiments, the detectable change is a change in FRET efficiency, for example, cleavage of the target sequence by a *Pseudomonas* spp. protease results in a change in FRET efficiency. As used herein, FRET is a proximity assay based on the non-radioactive transfer of energy from one fluorophore (the donor) to an acceptor. The acceptor can be another fluorophore which usually emits fluorescence of a different colour. The acceptor can also be a quencher which does not emit light. According to the Förster equation (Förster (1948) and Förster (1960)), FRET efficiency depends on five parameters: (i) the overlap between the absorption spectrum of the second fluorophore and the emission spectrum of the first fluorophore, (ii) the relative orientation between the emission dipole of the donor and the absorption dipole of the acceptor, (iii) the distance between the fluorophores, (iv) the quantum yield of the donor and (v) the extinction coefficient of the acceptor.

Typically, the donor and acceptor are attached to the N- and C-terminal ends of the target sequence forming the sensor of the present invention. When the donor and acceptor are bound to the intact target sequence, emission from the acceptor is observed upon excitation of the donor particle. Once the protease cleaves the target sequence, the energy transfer between the donor and the acceptor is disrupted. When both the donor and the acceptor are fluorophores, cleavage changes the ratio of donor to acceptor fluorescence emission. When the donor is a fluorophore and the acceptor is a quencher, cleavage increases fluorescence intensity. This is because the distance between the donor and acceptor greatly increases upon cleavage of the sensor.

In some embodiments, the detectable change is a change in phosphorescence, for example, cleavage of the target sequence by a *Pseudomonas* spp. protease results in a change in phosphorescence. The change in phosphorescence can be measured using techniques known to the person skilled in the art. As used herein, "phosphorescence" is a process in which energy absorbed by a substance is released relatively slowly in the form of light.

In some embodiments, the detectable change is a change in time resolved fluorescence. The change in fluorescence can be measured using techniques known to the person skilled in the art.

In some embodiments, the detectable change is a change in absorbance, for example, cleavage of the target sequence by a *Pseudomonas* spp. protease results in a change in absorbance. In some embodiments, the sensor comprises a chromophore (such as p-nitroaniline). Cleavage of the target sequence by a *Pseudomonas* spp. protease would change the chemical environment of the chromophore and result in a change in absorbance which can be measured using a spectrophotometer. In some embodiments, the target sequence of the sensor is labelled with a chromophore, preferably a high epsilon chromophore, at the N- or C-terminus and the unlabelled terminus is attached to a solid support (for example, bead or surface). Cleavage of the target sequence by a *Pseudomonas* spp. protease separates the chromophore from the solid support, releasing the chromophore into the reaction medium. The amount of chromophore released into the medium can be determined using techniques known to the person skilled in the art. In a further embodiment, the sensor comprises an enzyme (for example, alkaline phosphatase/horseradish peroxidase etc.) that can generate an absorbance change using a colourigenic substrate, or a chemiluminescent substrate. The sensor is also attached to a solid substrate (for example, bead or surface). Cleavage of the target sequence by a *Pseudomonas* spp. protease would release the colour or light generating moiety into the reaction medium which could be detected using an enzymatic assay using techniques known to the person skilled in the art.

In some embodiments, the detectable change is a change in antibody binding, for example, cleavage of the target sequence by a *Pseudomonas* spp. protease releases an epitope which can be detected using an antibody. In some embodiments, the sensor comprises an epitope (for example, myc, Flag, hexahistidine and the like). Optionally, the sensor is attached to a solid support. Cleavage of the target sequence by a *Pseudomonas* spp. protease releases the epitope into the reaction medium which can be detected using methods known to the person skilled in the art. Unreleased epitopes can also be detected using the relevant antibodies (for example, anti-myc, anti-6×His tag or anti-FLAG) and methods known to the person skilled in the art.

In some embodiments, the detectable change is a change in mass. As would be understood by the person skilled in the art, cleavage of the target sequence by a *Pseudomonas* spp. protease changes the mass of the sensor. The change in mass can be detected using any suitable technique known to the person skilled in the art, for example any microweighing technique such as surface plasmon resonance (SPR) or a quartz crystal microbalance (QCM). In some embodiments, the sensor can be immobilised on an SPR chip, or QCM via any technique known to the person skilled in the art (for example, a thiol linkage). In the case of SPR, cleavage of the target sequence by a *Pseudomonas* spp. protease results in a local refractive index change, resulting in a change in SPR which can be measured. In the case of QCM, cleavage of the target sequence by a *Pseudomonas* spp. protease changes the mass of the resonator, and a change can be detected in the resonant frequency of the QCM. In some embodiments, the sensor comprises a large molecule, bead or the like, so that when the target sequence is cleaved, the change in mass is greater.

Compositions, Methods and Uses

The sensors of the present invention may be included in compositions for use in detecting bacterial proteases. In some embodiments, there is provided a composition comprising a sensor in accordance with the present invention and an acceptable carrier. As used herein, the term "acceptable carrier" includes any and all solids or solvents (such as phosphate buffered saline buffers, water, saline) dispersion media, coatings, and the like, compatible with the methods and uses of the present invention. The acceptable carriers must be 'acceptable' in the sense of being compatible with the other ingredients of the composition and not inhibiting or damaging the proteases being tested for. Generally, suitable acceptable carriers are known in the art and are selected based on the end use application.

As the skilled person would appreciate, the sensors of the present application can be used to detect the presence or absence of *Pseudomonas* spp. protease in a sample, and if present may also be used to determine the activity of the *Pseudomonas* spp. protease. Therefore, in some embodiments there is provided a method of detecting a *Pseudomonas* spp. protease in a sample, the method comprising i) contacting a sample with the sensor of the present invention;

and ii) detecting a change in the sensor, wherein said change corresponds to the presence of a *Pseudomonas* spp. protease in the sample.

The sensors can be used to detect and quantify κ-caseinolytic proteases from *Pseudomonas* spp. and other bacteria in dairy products to predict their shelf-life and quality and to optimise management and processing treatments designed to reduce, delay or eliminate bacterial protease-driven spoilage.

As used herein, the term "spoilage" in reference to dairy and other food products is a term used to describe the deterioration of the products texture, colour, odour and/or flavour to the point where it is no longer appetizing or suitable for human consumption. In the case of spoilage caused by micro-organisms such as *Pseudomonas* spp., spoilage often involves the degradation of proteins (such as casein and whey), carbohydrates, and fats by the microorganisms or their enzymes. The present inventors have observed that at 37° C., bacterial protease can cause milk spoilage when it is present in concentrations greater than 1 pM. In this case the spoilage is manifested by phase separation of the milk (with the resultant appearance of "curds and whey").

As used herein, the term "dairy product" includes milk and products derived partially or in full from milk. The milk may be obtained from any mammal, for example cow, sheep, goat, horse, camel, buffalo, human and the like. Dairy products include, but are not limited to, raw milk, low fat milk, skim milk, pasteurized milk, UHT milk, lactose-modified UHT milk, fortified UHT milk, flavoured UHT milk, and combinations of these products as well as UHT infant formula, cheese, yoghurt, whey, buttermilk, cream, milk powder, powdered infant formula and butter and the like. In some embodiments, there is provided a method of detecting spoilage of a dairy product, the method comprising i) contacting a sample with the sensor of the present invention; and ii) detecting a change in the sensor, wherein said change indicates that the dairy product is spoilt, has begun to spoil or has the potential to spoil. In this example, the target sequence comprises a cleavage site that can be cleaved by a *Pseudomonas* spp. bacterial protease that causes, at least in part, milk spoilage. The product may also be an extract, such as a partially purified portion, of dairy product comprising, or suspected of comprising, the protease.

The sensors of the present invention can also be used to detect or estimate biofilms comprising *Pseudomonas* spp. For example, the sensors of the present invention can be used detect or estimate biofilms comprising *Pseudomonas* spp. which may be present in inaccessible or hard to reach parts of milk processing plant and equipment. In another example, the sensors of the present invention can also be used to detect or estimate biofilms in inaccessible or hard to reach parts of food and/or beverage processing plant and equipment. In a further example, the sensors of the present invention can also be used to detect or estimate biofilms in medical equipment and devices. The ability to detect or estimate biofilms comprising *Pseudomonas* spp. without having to dismantle equipment and the like would assist in the scheduling and assessment of routine "clean in place" and targeting of "clean out of place" procedures.

The sensors of the present invention can also be used to detect *Pseudomonas* spp. infections. At least one serious outbreak of catheter infections has been linked to *Pseudomonas fluorescens*. Other pseudomonads are important opportunistic pathogens. Use of these sensors to detect infection can aid infection management and treatment in clinical situations.

As the skilled person would be aware, the sensors of the present invention can also be multiplexed. In this system, two or more different sensor molecules are provided which are cleaved by different proteases. For example, a sensor of the present invention can be multiplexed with a sensor that is cleaved by bovine plasmin (see, for example, PCT/AU2013/000378). In some embodiments, each different sensor molecule may include a different donor and/or acceptor molecule such that they emit at different wavelengths to enable the detection and quantification of different target compounds. In some embodiments, each different sensor molecule may the same donor and/or acceptor molecule. In some embodiments, a single fluidic detection chamber is used. In some embodiments, a multi-channel detection device may be used.

The "sample" can be any substance or composition that has the potential to contain a *Pseudomonas* spp. and/or a *Pseudomonas* spp. protease. Typically, a sample is any substance known or suspected of comprising the bacteria and/or protease. Examples of samples include liquid, biological material and instruments. In some embodiments, the sample is selected from the group consisting of a dairy product or an extract thereof, soil or an extract thereof, clinical samples or an extract thereof, samples (e.g. swab, rinse and the like) from medical equipment, samples from machinery (e.g. swab, rinse and the like), samples from food processing equipment (e.g. swab, rinse and the like), plant material or an extract thereof and the like. In some embodiments, the clinical sample includes but is not limited to blood, serum, sputum, mucus, pus, peritoneal fluid and other bodily fluids. In some embodiments, food processing equipment includes, but is not limited to, transport tankers, holding tanks, processing machinery, lines, tubing, connectors, valves and the like. The sample may be derived (for example a swab, rinse or the like) from machinery. Machinery includes any machinery suspected or known to harbour the bacteria and/or protease, for example any machinery involved in the production, storage and processing of a dairy product. In some embodiments, machinery includes, but is not limited to, buffer and holding silos, welded joints, buffer tank outlets, conveyer belts, ultrafiltration membranes, valves, air separators, tanker trucks, tanker truck storage tanks, storage tanks, valves, gaskets, connecting pipes and the like. The sample may also be derived from medical equipment, for example the sample may be swabs or rinses from medical equipment including, but not limited to, catheters, intravenous lines, ventilators, wound dressings, contact lenses, dialysis equipment, medical devices and the like.

The dairy product can be, but is not limited to, raw milk, low fat milk, skim milk, pasteurized milk, UHT milk, lactose-modified UHT milk, fortified UHT milk, flavoured UHT milk, and combinations of these products as well as UHT infant formula, cheese, yoghurt, whey, buttermilk, cream, milk powder, powdered infant formula and butter and the like. The sample may be obtained directly from the environment or source, or may be extracted and/or at least partially purified by a suitable procedure before a method of the invention is performed.

In some embodiments, the sample is an aqueous liquid. For example, the sample includes but is not limited to, milk, fruit juices, other beverages and bodily fluids including blood serum.

The methods of the present invention can be performed on any system suitable for measuring a detectable change.

As the person skilled in the art will appreciate the methods of the present invention can be performed in a batch (for example batch format using a plate reader) or flow format.

For example, the methods of the present invention can be performed in a microplate format using a microplate reader equipped with the appropriate filters. The methods of the present invention can also be performed on a microfluidic device, such as described in PCT/AU2013/000378.

In contrast to previously described methods, the present invention can be used in a direct, selective assay to measure *Pseudomonas* spp. protease in milk and at picomolar levels. For example, in some embodiments, at least 1 pM of *Pseudomonas* spp. protease can be detected. In some embodiments, at least 5 pM of *Pseudomonas* spp. protease can be detected. In some embodiments, at least 10 pM of *Pseudomonas* spp. protease can be detected. In some embodiments, at least 20 pM of *Pseudomonas* spp. protease can be detected. In some embodiments, at least 30 pM of *Pseudomonas* spp. protease can be detected. In some embodiments, at least 40 pM of *Pseudomonas* spp. protease can be detected. In some embodiments, at least 50 pM of *Pseudomonas* spp. protease can be detected. In some embodiments, at least 60 pM of *Pseudomonas* spp. protease can be detected. In some embodiments, at least 70 pM of *Pseudomonas* spp. protease can be detected. In some embodiments, at least 80 pM of *Pseudomonas* spp. protease can be detected. In some embodiments, at least 90 pM of *Pseudomonas* spp. protease can be detected. In some embodiments, at least 100 pM of *Pseudomonas* spp. protease can be detected. In some embodiments, at least 150 pM of *Pseudomonas* spp. protease can be detected.

Previously reported methods for detecting bacterial proteases in milk require very long incubation times (up to 14 days or more (Button et al., 2011). In contrast, the methods of the present invention are able to be performed in less than 3 hour, 2 hour, less than 1 hour, less than 30 minutes or less than 15 minutes. In some embodiments, the methods of the present invention are able to be performed in less than 2 hours. In some embodiments, the methods of the present invention are able to be performed in less than 1 hour. In some embodiments, the methods of the present invention are able to be performed in less than 30 minutes. Preferably, the methods of the present invention are able to obtain the desired sensitivity in less than 15 minutes.

The methods and sensors of the present application, can be more sensitive to bacterial proteases than to bovine plasmin. In an embodiment, the present invention is at least 5 fold, or at least 10 fold, or a 5 fold to 1,000 fold, or 5 fold to 100 fold, or 5 fold to 50 fold, or 5 fold to 20 fold, or and in some circumstances up to 100 to 1,000 fold more selective for bacterial proteases over bovine plasmin.

Sample Preparation

Proteases, such as plasmin, its zymogen plasminogen and the bacterial proteases, can be associated with the casein micelle and milk fat globule in dairy products. This can make it difficult to measure the amount of protease present in these samples. Without wishing to be bound by theory, it is thought that the caseins, which are the natural substrates for these proteases, can act as competitive inhibitors towards the substrates used in the protease assays. Various methods for measuring the amount of protease in a diary product have been described (for example, for plasmin see Saint-Denis et al. (2001) and Rauh et al. (2014)). The amount of protease measured by these assays can vary depending on how the sample has been prepared for the assay. There is a need for improved methods which dissociate the proteases from the casein micelle and that can be used to prepare samples for protease assays.

The present inventors have found an improved method for dissociating protease from a casein micelle. In one aspect the present invention provides, a method of dissociating protease from a casein micelle, the method comprising sonicating a composition comprising protease associated with casein micelle in the presence of a compound which competes with the protease binding casein. In some embodiments, there is provided a method of dissociating protease from a casein micelle, the method comprising sonicating a composition comprising protease associated with casein micelle in the presence of a compound which competes with the protease binding casein and a calcium chelating agent. The improved methods increase the amount of free protease and can be used to prepare samples for protease assays, such as those using the protease sensor molecules described hereinabove. As used herein, the term "free protease" refers to protease that is disassociated from the casein micelle.

In some embodiments, the composition is a sample of a dairy product. The composition may also be an extract, such as a partially purified portion, of dairy product.

The compound which competes with the protease binding casein can be any suitable compound known to the person skilled in the art. In some embodiments, the compound is a derivative or analogue of lysine. Suitable derivatives or analogues of lysine include, but are not limited to, aminocaproic acid, trans-4-aminomethylcyclohexane carboxylic acid, trans-4-amino-ethylcyclohexane carboxylic acid, and esters thereof. Aminocaproic acid is also known as ε-aminocaproic acid, ε-Ahx, or 6-aminohexanoic acid. Examples of aminocaproic acid and esters thereof include aminocaproic acid, alkyl esters such as hexyl ε-aminocaproate, and aralkyl esters such as benzyl ε-aminocaproate. Examples of trans-4-aminomethylcyclohexanecarboxylic acid and esters thereof include trans-4-aminomethylcyclohexanecarboxylic acid, aralkyl esters such as benzyl trans-aminomethylcyclohexanecarboxylate, and aryl esters such as phenyl trans-aminomethylcyclohexanecarboxylate and 4-(2-carboxyethyl)phenyl trans-aminomethylcyclohexanecarboxylate. Examples of trans-4-aminoethylcyclohexanecarboxylic acid and esters thereof used in this invention include trans-4-amino-ethylcyclohexanecarboxylic acid, aralkyl esters such as benzyl trans-aminoethylcyclohexanecarboxylate, and aryl esters such as phenyl trans-aminoethylcyclohexanecarboxylate and 4-(2-carboxyethyl)phenyl trans-aminoethylcyclohexanecarboxylate. In preferred embodiments, the derivative or analogue of lysine is ε-aminocaproic acid (also referred to as EACA).

The compound which competes with the protease binding casein is present in an amount which is sufficient to increase the amount of free protease. In some embodiments, the composition comprises about 0.1 mM to about 20 mM of the compound, about 0.3 mM to about 10 mM of the compound, about 0.5 mM to about 5 mM of the compound, about 0.6 mM to about 4 mM, or about 0.7 mM to about 2 mM of the compound. For example, the composition can contain about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM or about 2.0 mM of the compound. In preferred embodiments, the composition comprises 0.8 mM, about 0.9 mM, about 1 mM, about 1.1 mM or about 1.2 mM of the compound. In more preferred embodiments, the composition comprises about 1 mM of the compound.

The composition can comprise a calcium chelating agent. Any suitable calcium chelating agent known to the person skilled in the art can be used. Without wishing to be bound by theory it is thought that the calcium chelating agent reduces the amount of free calcium ions and colloidal calcium phosphate resulting in at least partial dissociation of the casein micelle. In some embodiments, the calcium chelating agent is selected from the group consisting of citrate ions, phosphate ions, pyrophosphate ions, polyphosphate ions and polycarboxylates and salts thereof. In some embodiments, the calcium chelating agent is selected from the group consisting of sodium hexametaphosphate, disodium hydrogen phosphate, trisodium citrate, sodium phytate, ethylenediaminetetraacetic acid and ethylene glycol-bis(β-aminoethyl ether)-N,N,N',N'-tetraacetic acid. The concentration of the calcium chelating agent can vary depending on the predicted amount of metal ion to be chelated and/or the type of calcium chelating agent used. In some embodiments, the concentration of calcium chelating agent is between about 0.01 M and about 0.5 M, or about 0.05 M and about 0.4 M, or about 0.05 M and about 0.1 M. In some embodiments, the calcium chelating agent is citrate ions or salts thereof. In some embodiments, the calcium chelating agent is tri-sodium citrate. In some embodiments, the concentration of tri-sodium citrate is between about 0.01 M and about 0.5 M, or about 0.05 M and about 0.4 M, or about 0.05 M and about 0.1 M.

In some embodiments, the pH of the composition can be selected by the person skilled in the art based on the calcium chelating agent used. The pH can affect the stability and effectiveness of the chelating agent. In some embodiments, the pH of the composition is greater than 6.0. In some embodiments, the pH is greater than 7.0. In some embodiments, the pH is between about 8.0 and about 10.0, about 8.3 and 9.5, about 8.5 and about 9.3, about 8.7 and about 9.1, about 8.8 and about 9.0, or about 8.9. A buffer can be added to the composition to maintain the pH. Any suitable buffer can be used.

The composition can also comprise an acceptable carrier and/or additive. Generally, suitable acceptable carriers and/or additive are known in the art and are selected based on the end use application. For example, in some embodiments the composition comprises sodium chloride. In some embodiments, the concentration of sodium chloride is between about 0.01 M and about 0.3 M, or about 0.025 M and about 0.25 M, or about 0.04 M and about 0.1 M, or about 0.05 M. In some embodiments, the concentration of sodium chloride is 0.05 M sodium chloride.

In preferred embodiments, the protease causes, at least in part, milk spoilage. In some embodiments, the protease is relatively heat stable. In some embodiments the protease is plasmin or its zymogen, plasminogen. In some embodiments the protease is plasmin. In some embodiments, the method further comprises converting plasminogen to plasmin using methods known to the person skilled in the art. In some embodiments, the protease is a bacterial protease. In some embodiments, the bacterial protease is produced by a *Pseudomonas* spp. In some embodiments, the *Pseudomonas* spp. is *Pseudomonas fluorescens, Pseudomonas fragi, Pseudomonas ludensis, Pseudomonas putida, Pseudomonas* LBSA1 or *Pseudomonas aureofaciens*. In some embodiments, the protease is a bacterial extracellular protease. In some embodiments, the bacterial extracellular protease is an alkaline metalloprotease. In some embodiments, the protease belongs to the serralysin family of proteases. In some embodiments, the protease is an AprX protease. In some embodiments, the protease has at least has at least 50%, 60%, 70%, 80%, 90%, 95% or 99% sequence identity, or 100% sequence identity, to AprX of *P. fluorescens* n° 114 (NCBI GenPept ID BAA28268).

One of the advantages of the present method is that it is quicker to perform than other methods described in the art. For example, the method described in Rauh et al. (2014) requires two, 15 minute incubations. The first incubation is thought to dissociate the casein micelles. The second incubation is thought to dissociate protease from the caseins. The present inventors have found that methods described herein reduce the amount of time required for sample preparation. In some embodiments, the sonicating is carried out for 15 minutes or less, 10 minutes or less, 5 minutes or less, or 2 minutes or less. Preferably, the sonicating is carried out for 5 minutes or less. More preferably, the sonicating is carried for 2 minutes or less. As used herein, "or less" requires sonication for at least 1 second.

In some embodiments, the sonicating is continuous. In alternative embodiments, the sonicating is pulsed.

Any suitable sonicator or homogenizer known to the person skilled in the art may be used. Suitable sonicators or homogenizers include, but are not limited to, a Honda Electronics Sonac-200 controller, a modified Honda ZO41 ultrasonic cutter, an inline ultrasonic microreactor such as Heilscher GDmini2, a Misonix sonicator 3000 or a Q55 Sonicator. In some embodiments the sonication may be carried out with a sonic syringe, such as Sono Tek's SonicSyringe™ system.

Preferably, the sonicator can be used to sonicate a sample volume of 10 mL or less, 5 mL or less, 2.5 mL or less, 1.25 mL or less or 0.1 mL or less. In some embodiments, the sonicator can be used to sonicate a sample volume of about 2.5 mL. In some embodiments, the sonicator can be used to sonicate a sample volume of about 1.25 mL. In some embodiments, the sonicator can be used to sonicate a sample volume of about 0.1 mL.

In some embodiments, the sonicator has a probe tip diameter is 20 mm or less, 15 mm or less, 11 mm or less, 9 mm or less, 7 mm or less, 5 mm or less, 4 mm or less, 3 mm or less or 2 mm or less. In some embodiments, the sonication may be carried out with a micro sonicator tool (such as the Honda Electronics ZO41 or ZO-40W Ultrasonic Cutter) equipped with a suitable 4 mm probe tip diameter. In still another embodiment, the sonicator is an inline ultrasonic microreactor, such as Heilscher GDmini2 (or a lower power version of this equipment) equipped with an 11 mm probe tip diameter.

Any suitable sonication device displacement amplitude can be used. In some embodiments, the sonicating is carried out with sonication device displacement amplitude of between about 15 μm and 300 μm, or between about 40 μm and 300 μm, or between about 120 μm and 300 μm. In some embodiments, the sonicating is carried out with sonication device displacement amplitude of between about 15 μm and 300 μm, between about 15 μm and 120 μm, or between about 15 μm and 25 μm. In some embodiments, the sonicating is carried out at with sonication device displacement amplitude of about 40 μm.

Any suitable frequency can be used. In some embodiments, the sonicating is carried out at a frequency of between about 10 kHz and about 60 kHz, for example about 10 kHz, about 20 kHz, about 30 kHz, about 40 kHz, about 50 kHz, or about 60 kHz. In some embodiments, the sonicating is carried out at a frequency of between about 15 kHz and about 30 kHz. In some embodiments, the sonicating is carried out at a frequency of between about 28 kHz and about 40 kHz.

Any suitable power consumption can be used. In some embodiments, the sonicating is carried out at a power consumption of less than about 55 watts, less than about 50 watts, less than about 45 watts, less than about 40 watts, less than about 35 watts, less than about 30 watts, less than about 25 watts, less than about 20 watts or less than about 15 watts, In preferred embodiments, the sonicating is carried out at a power of less than about 25 watts.

In some embodiments, the sonicating is carried out on a sample volume of about 0.05 mL to about 10 mL, 0.08 mL to 2 mL or 0.1 mL to about 2.5 mL. For example, the sonicating is carried out on a sample volume of about 0.1 mL, about 0.2 mL, about 0.3 mL, about 0.4 mL, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, about 2.0 mL, about 2.1 mL, about 2.2 mL, about 2.3 mL, about 2.4 mL, or about 2.5 mL. In some embodiments, the sonicating is carried out on a sample volume of about 0.1 mL. In some embodiments, the sonicating is carried out on a sample volume of about 1.25 mL. In some embodiments, the sonicating is carried out on a sample volume of about 2.5 mL.

As will be appreciated by the person skilled in the art sonicating parameters (including those mentioned above) can vary depending on sample volume, sonicator, sonicator probe, tip depth, sample vessel and the like. The person skilled in the art will be able to select the sonicating parameters required to homogenise the milk such that after sonication it does not form a separate layer on centrifugation at approximately 12,000×g for 2 minutes (FIG. 2). Preferably, the sonicating parameters are selected to provide low power sonication for the minimum amount of time required to homogenise the milk such that after sonication it does not form a separate layer on centrifugation at 12,000×g for 2 minutes.

For example, in some embodiments, the sonicator is a Honda Electronics Sonac-200 controller with a probe tip diameter of 11 mm, the sample volume is 2.5 mL (2 mL raw milk with 0.5 mL added EACA buffer), the sample is in a glass vial with an internal diameter of 23 mm, the sonication is carried out for about two minutes with the following parameters: Frequency=28 kHz, Amplitude=17-21 μm and Power consumption: 25 W.

In other embodiments, the sonicator is a Honda ZO41 ultrasonic cutter modified to have a probe tip diameter of 4 mm, the sample volume is 2.5 mL (2 mL raw milk and 0.5 mL added EACA buffer), the sample is in a glass vial with an internal diameter of 23 mm, the sonication is carried out for about 2-6 minutes with the following parameters: Frequency=40 kHz; Amplitude=16-19 μm and power consumption: 5-8 W.

In still other embodiments, the sonicator is a Honda ZO41 ultrasonic cutter modified to have a probe tip diameter of 4 mm, the sample volume is about 1.25 mL (with 1 mL raw milk and 0.25 mL added EACA buffer), the sample is in a 1.5-2 mL plastic Eppendorf tube with an internal diameter of about 10 mm and the sonication is carried out for about 1-6 minutes with the following parameters: Frequency=40 kHz; Amplitude=16-19 μm and power consumption: 5-8 W.

In another embodiment, the sonicator is a Honda ZO41 ultrasonic cutter modified to have a probe tip diameter of 4 mm, the sample volume is about 0.150 mL (with 0.120 mL raw milk and 0.030 mL added EACA buffer), the sample is in a 0.3 mL well of 96 well plate with internal diameter of 6 mm and the sonication is carried out for about 1-2 minutes with the following parameters: Frequency=35 kHz; Amplitude=10 μm and acoustic power level 0.25 W.

As would be understood by the person skilled in the art, the sonicating is carried out at a temperature which does not cause denaturation and/or inactivation of the protease. In some embodiments, the sonicating is carried out a temperature less than about 50° C., preferably less than 40° C., and most preferably less than 30° C. For example, the sample may be incubated on ice or in an ice bath during sonication. The sample may be maintained (for example by refrigeration or other suitable technique) at or below 10° C., at or below 10° C. or at or below 4° C. when sonicating.

As noted above, the method of dissociating protease from a casein micelle can be used to prepare a sample for a protease assay. The method can also be used to prepare a sample of dairy product for a protease assay and to determine the concentration of protease in the dairy product. Therefore, in another aspect there is provided a method of determining the concentration of protease in a dairy product, the method comprising
  (i) processing a sample of the diary product using the method described herein;
  (ii) measuring protease activity in the processed diary product; and
  (iii) determining the concentration of protease of the dairy product based on the protease activity. In some embodiments, sample of the dairy product can also be an extract, such as a partially purified portion, of dairy product. In some embodiments, the dairy product selected from the group consisting of raw milk, low fat milk, skim milk, pasteurized milk, UHT milk, lactose-modified UHT milk, fortified UHT milk, flavoured UHT milk, UHT infant formula, cheese, yoghurt, whey, buttermilk, cream, milk powder, powdered infant formula and butter and combinations thereof, and/or an extract of one or more thereof comprising a protease bound to casein.

In some embodiments, step (ii) comprises mixing the processed diary product with a sensor molecule comprising a target sequence having at least one protease cleavage site and optionally a detectable label, wherein cleavage of the target sequence by the protease produces a detectable change; and measuring the detectable change.

In some embodiments, the sensor molecule is a sensor molecule of the invention. In some embodiments, the sensor molecule is a *Pseudomonas* spp. protease sensor molecule as described herein. In some embodiments, the sensor molecule has a polypeptide sequence selected from SEQ ID NO: 105, 106 and 107. In some embodiments, the sensor molecule is a sensor molecule defined in PCT/AU2013/000378. In some embodiments, the sensor molecule has the polypeptide sequence SEQ ID NO: 109. In some embodiments, the sensor is cleaved by plasmin (see, for example, PCT/AU2013/000378). In some embodiments, the sensor is cleaved by bacterial proteases, for example, a *Pseudomonas* spp. protease as defined herein.

In some embodiments, the sensor molecule comprises a detectable label and the detectable label comprises a chemiluminescent donor domain and an acceptor domain covalently attached to the target sequence. In some embodiments, the acceptor domain is as defined herein. In some embodiments, the chemiluminescent donor domain is as defined herein.

The sensor molecule comprises a target sequence having at least one protease cleavage site. In some embodiments, the protease cleavage site is selected from the group consisting of SF, FM, NQ, NT, EI, QQ, and KZ where Z is Q, N, K, Y, V or E, and combinations thereof. In some embodiments, the protease cleavage site is selected from the group consisting of SF, FM, NQ, NT, EI, and KZ where Z is Q, N, K, Y, V or E, and combinations thereof. In some embodiments, the protease cleavage site is selected from the group consisting of SF, FM, NQ, NT, EI, KK, KQ and KN and combinations thereof. In some embodiments, the protease cleavage site is selected from the group consisting of KK, KY, KV and KE and combinations thereof.

In some embodiments, the target sequence comprises a plasmin cleavage site. In some embodiments, the target sequence comprises the amino acid sequence KZ, where Z is K, Y, V or E. In some embodiments, the target sequence comprises the amino acid sequence LQXXXXKZKLQ (SEQ ID NO: 110, where Z is K, Y, V or E, and X is any amino acid. In some embodiments, the target sequence comprises LQGSKKYKVKEGSLQ (SEQ ID NO: 111).

In some embodiments, the target sequence comprises a bacterial protease cleavage site. In some embodiments, the target sequence comprises a *Pseudomonas* spp. cleavage site. In some embodiments, the target sequence comprises SEQ ID NO: 1-94.

EXAMPLES

The following examples set forth preferred sensors and methods in accordance with the invention. It is to be understood, however, that these examples are provided by way of illustration and nothing therein should be taken as a limitation upon the overall scope of the invention.

Example 1

Construction of Sensors

DNA constructs encoding the $BRET^2$-plasmin sensor and $BRET^2$-bacterial protease Pflu sensors 1, 2, and 3 were synthesised by GenScript (USA). The sensors comprised Rluc2 as the chemiluminescent donor and a variant of green fluorescent protein ($GFP^2$) as the acceptor. The constructs were cloned into a pRSET vector (BioLabs, Australia) using EcoRI and XhoI restriction sites, to make a pRSET-Pflu vector encoding the protease sensor. The polynucleotide sequences encoding the protease sensors are shown in SEQ ID NO: 102-104. The polypeptide sequence of the protease sensors are shown in SEQ ID NO: 105-107. The polynucleotide sequences encoding the plasmin sensor is shown in SEQ ID NO: 108. The polypeptide sequence of the plasmin sensor is shown in SEQ ID NO: 109.

Cells of *Escherichia coli* strain BL21(DE3) (Novagen) were transformed with pRSET-Pflu vector encoding the protease sensor. The sensors were expressed in *Escherichia coli* strain BL21(DE3) (Novagen). An overnight culture was grown from a single colony in LB (10 g tryptone, 5 g yeast extract, 5 g NaCl (pH 7.4) containing 100 pg/mL ampicillin and 2% glucose at 37° C., 200 rpm. Expression was induced by inoculating 250 mL LB containing 100 pg/mL ampicillin to an OD600 of 0.1 and incubating at 37° C. (200 rpm) for 4.5 hours followed by overnight incubation at 22° C. (200 rpm). Cells were harvested 24 hours after inoculation.

Cells were harvested by centrifugation at 4335×g (4° C.) for 15 minutes and resuspended in equilibrium buffer (57.7 mM $Na_2HPO_4$, 42.3 mM $NaH_2PO_4$, 300 mM NaCl, pH 7.0). The cells suspension was passed through a homogenizer (Microfluidics M-100P (Newton, Massachusetts, USA)) at a pressure of ≈21,000 psi and the soluble protein fraction was isolated by centrifugation at 15,000×g (4° C.) for 15 minutes. Proteins were purified using cobalt affinity chromatography (TALON® Superflow Metal Affinity Resin (Takara Clontech, Australia)) according to the manufacturer's instructions. Following elution of the purified protein with 150 mM imidazole, the sample was dialyzed against plasmin cleavage buffer (50 mM Tris (pH 8), 10 mM NaCl and 25 mM lysine) using a cellulose dialysis membrane (12,000 molecular weight cutoff (Sigma)). Aliquots of 500 μL of the purified protein were snap-frozen on dry ice and stored at −80° C.

Example 2

Materials and Methods

Crude Bacterial Protease

An isolate of *Pseudomonas fluorescens* (Strain 65) was plated on OXOID agar plates and incubated at 28° C. for 2 days. 100 ml of sterile nutrient broth (NB) was innoculated with three colonies from the plate and incubated for 48 hr at 28° C. 10 mL of the culture was centrifuged at 6000×g for 10 minutes. The supernatant was discarded and the cell pellet resuspended in 1 mL of sterile isotonic saline solution (0.85% w/v) and added to 99 mL skimmed UHT milk (COLES Australian skimmed milk, 99% fat free). The culture was incubated for 8 days at 4° C. with circular agitation at 150 rpm. A control culture was prepared by adding 1 mL 0.85% w/v of saline to 99 mL skimmed UHT milk and incubating for 8 days under the same conditions. Following this, the cultures were centrifuged at 3,000×g for 10 minutes at 4° C. The supernatant was collected, filter sterilised over a 0.22 μm filter and used as a source of crude protease. This was aliquoted into 1 ml aliquots and stored at −80° C.

SDS-PAGE (FIG. 3) analysis of the crude extract prepared from skimmed milk innoculated with *P. fluorescens* demonstrated the presence of a dominant band between 46 and 58 kDa, which is consistent with the molecular mass of 50 KDa that characterises a class of zinc-dependent metalloproteases (AprX proteases) produced by a number of different *P. fluorescens* strains in milk (Dacres et al., 2014; Button et al., 2011). The concentration of protease secreted by *P. fluorescens* strain 65 was estimated to be 0.34 μM by densitometric analysis of stained bands on an SDS-PAGE gel.

Protease Assay

Protease assays were carried out in 96-well plates with a final volume of 100 μL. Purified plasmin sensor (10 nM) was incubated for 10 minutes at 28° C. with varying amounts of the crude bacterial protease or plasmin (human or bovine, Sigma) in cleavage buffer (50 mM Tris-HCl, 50 mM NaCl, 25 mM lysine, pH 8) or with the addition of 50 μL of full fat or skimmed UHT milk (Coles). Calibration graphs were generated by assaying protease concentrations between 1 pM and 10 nM. The $BRET^2$ signal was measured following the 10 minute incubation. For $BRET^2$ measurement, 5 μL Clz400a substrate (100 μM) was added following the 10 minutes incubation period.

Simultaneous dual emission BRET measurements were carried out with a POLARstar OPTIMA microplate reader (BMG LabTech, Australia) using a $BRET^2$ emission filter set, comprising an RLuc2/Clz400a emission filter (410 nm, bandpass 80 nm) and a $GFP^2$ emission filter (515 nm, bandpass 30 nm). An integration time of 0.5 second was used.

Data Analysis

Using the microplate spectrometer, BRET ratios were calculated as the ratio of bioluminescence emissions measured at 500 nm and 470 nm. BRET ratio was calculated by dividing the $GFP^2$ intensity (average 0-5 s) by the RLuc2 intensity (average 0-5 s). The BRET ratios were normalised using the normalisation function in Graphpad Prism 7 for Windows, plotted against Log [Protease] values and fitted with a Log [Agonist] vs normalized response—variable slope model.

Results

Calibration curves were constructed for the plasmin sensor in full fat UHT milk for bovine plasmin and human plasmin (FIG. 4) or bacterial proteases. The plasmin sensor had an $EC_{50}$ of 5.6 nM for the human plasmin and 108 nM for bovine plasmin (Table 3). Preliminary studies comparing the response of the plasmin sensor to human plasmin, bovine plasmin and bacterial proteases (FIG. 5) infer that the $EC_{50}$ for bacterial proteases is approximately 50 nM in full fat UHT milk.

Further to this the plasmin sensor was calibrated with bacterial protease (FIG. 6) in raw milk. The plasmin sensor had an EC50 of 1.4 nM for bacterial proteases in raw milk (Table 3).

Example 3

The sensors of the present application can be used to detect *Pseudomonas* spp. protease in samples such as dairy products. Pflu sensors 1, 2, and 3 were prepared as described in example 1. Crude bacterial protease was prepared as described in example 2. The protease assay was performed as described in example 2 using 10 nM purified sensor.

Results

Calibration curves were constructed for Pflu sensor 1, 2 and 3 in full fat UHT milk for bacterial proteases, bovine plasmin and/or human plasmin. The calibration curves are shown in FIGS. 7 (Pflu sensor 1), 8 (Pflu sensor 1), 9 (Pflu sensor 2) and 10 (Pflu sensor 3).

The Pflu sensor 1 had an $EC_{50}$ of 0.7 nM for bacterial proteases and 169 nM for bovine plasmin and an $EC_{50}$ of 124 nM for human plasmin (Table 3). The Pflu sensor 1 is therefore approximately 174× more sensitive to the bacterial proteases than to human plasmin and 238× more sensitive to the bacterial proteases than to bovine plasmin. The sensitivity of a sensor is determined by dividing the $EC_{50}$ calculated from the calibration curve generated using plasmin by the $EC_{50}$ calculated from the calibration curve generated using bacterial protease.

The Pflu sensor 2 had an $EC_{50}$ of 2.6 nM for the bacterial protease fraction and 926 nM for human plasmin (Table 3). Bovine plasmin was not tested. The Pflu sensor 2 is therefore approximately 353× more sensitive to the bacterial proteases than to human plasmin.

The Pflu sensor 3 had an $EC_{50}$ of 2.3 nM for bacterial proteases and 1280 nM for human plasmin (Table 3). Bovine plasmin was not tested. The Pflu sensor 3 is therefore approximately 563× more sensitive to the bacterial proteases than to plasmin.

Conclusions

By changing the target sequence in the sensor the sensitivity of the bacterial protease sensor to bacterial proteases giving a combined linear range of 0.1-90 nM bacterial proteases and can measure Bovine plasmin levels ranging from 32-537 nM and Human plasmin levels ranging from 0.7 to 3680 nM. Plasmin concentration have been measured in the concentration range 1-5 nM (Benslimane et al., 2009) in raw milk using a colourimetric measurement and in the range 0.6-22 nM using an ELISA assay (Dupont et al., 1997). These data demonstrate that the sensors in accordance with the present invention are cleaved by bacterial proteases, are selective for bacterial proteases and largely or comparatively unresponsive to physiological levels of plasmin in milk.

Example 4

Materials and Methods
Raw Milk Samples

Six raw milk samples were obtained from an Australian dairy processor. The processor indicated that the cows these samples were obtained from were perceived to be high quality producers, able to consistently produce long shelf life fresh milk.

Pre-Treatment Protocol of Rauh et al. (2014)

Raw milk samples were sonicated (Misonix sonicator 3000; sample pulsar on, 0.5 seconds; pulsar off, 2.5 seconds; power 5.5) for 12 minutes. The raw milk samples were sonicated to create a homogeneous dispersion. Following sonication the milk samples were pre-treated using the pre-treatment method described in Rauh et al. (2014). Briefly, 1 mL sonicated raw milk was mixed with 250 µL 0.4 M tri-sodium citrate buffer (pH 8.9) and incubated for 15 minutes at room temperature with shaking to dissociate casein micelles. The citrate-treated milk was mixed (1:1) with 0.1 M Tris buffer (pH 8) containing 8 mM ε-aminocaproic acid (EACA) and 0.4 M NaCl and incubated for a further 15 minutes at room temperature with shaking.

TABLE 3

$EC_{50}$ and linear range calculated in 50% full fat milk spiked with crude protease. Linear range defined as range between 10% and 90% $BRET^2$ response. Selectivity factor (Bacterial protease: Plasmin) for bacterial protease sensors Pflu 1, Pflu 2 Pflu 3, Pflu-H3 and plasmin sensor.

| Target sequence | Sensor | Human plasmin | | Bovine plasmin | | Bacterial protease | | Selectivity for bacterial protease over human plasmin (fold) | Selectivity for bacterial protease over bovine plasmin (fold) |
|---|---|---|---|---|---|---|---|---|---|
| | | $EC_{50}$ (nM) | Linear range (nM) | $EC_{50}$ (nM) | Linear range (nM) | $EC_{50}$ (nM) | Linear range (nM) | | |
| LQGSKKYKVKEGSLQ (SEQ ID NO: 110) | Plasmin | 5.6 | 0.7-43 | 108 | 32-367 | ~50 1.4* | 10-90 0.2-9* | 0.1 | 2 |
| LQGSFMKKNQNTEIGSFE (SEQ ID NO: 72) | Pflu 1 | 124 | 10-1401 | 169 | 53-537 | 0.7 0.14* 0.2*[1] | 0.1-4 0.01-1.25* 0.02*[1]-3.16*[1] | 174 | 238 |
| LQGSFMNQNTEIGSFE (SEQ ID NO: 73) | Pflu 2 | 926 | 233-3680 | n.d. | n.d. | 2.6 | 0.6-12 | 353 | N.D. |
| LQGSLSFMAIPGSFE (SEQ ID NO: 74) | Pflu 3 | 1280 | 452-3622 | n.d. | n.d. | 2.3 | 0.5-11 | 563 | N.D. |
| LQGSKQKQKQKQGSFE (SEQ ID NO: 112) | Pflu-H3 | n.d. | n.d. | 174* | 28-1079* | 0.5* | .03-6.8* | N.D.* | 376* |

N.D. = not determined, *indicates values were calculated in raw milk samples, [1]indicates response to bacterial protease from strain 117 all other responses are for bacterial proteases from strain 65.

Calibration Curve Using the BRET$^2$ Plasmin Sensor

In order to generate a calibration curve, aliquots of the pre-treated milk samples were heated to 90° C. for 30 s to deactivate any endogenous plasmin. The heated pre-treated samples were spiked with human plasmin (Sigma) by adding 10 μL plasmin solution to 50 μL of the heated milk sample. The final concentration of added plasmin ranged between 0.001 and 500 nM. 5 μL BRET$^2$ plasmin sensor (10 nM) and 30 plasmin cleavage buffer was added to the spiked sample and the sample was mixed well by pipetting. The samples were incubated for 10 minutes at 28° C. Following the incubation, 5 μL of Clz400a substrate (100 μM) was added to the well and the BRET ratio was recorded as described above.

Determination of Endogenous Plasmin Concentration Using the BRET$^2$ Plasmin Sensor To determine the amount of plasmin present in the raw milk sample, 50 μL of the pre-treated raw milk sample was mixed with 5 μL BRET$^2$ plasmin sensor (10 nM) and 40 μL plasmin cleavage buffer in a microplate well. The mixture was incubated for 10 minutes at 28° C. Following incubation, 5 μL Clz400a substrate (100 μM) was added to the well and the BRET ratio was recorded. Concentrations calculated from the calibration curve were multiplied by a dilution factor of 2.5.

Validation Using a Colourimetric Substrate

The method of Rauh et al. (2014), using D-Val-Leu-Lys-4-nitroanilide dihydrochloride (V0882, Sigma Aldrich) as the colourimetric substrate, was used to validate the BRET$^2$ plasmin sensor-based measurements.

A 5 mM stock solution of D-Val-Leu-Lys-4-nitroanilide dihydrochloride was prepared by adding 1.81 mL 0.1 M Tris HCl (pH8.0) to 5 mg of the substrate.

The calibration curve was generated by mixing 50 μL of the pre-treated raw milk with 5 μl human plasmin in plasmin cleavage buffer and 45 μL of colourimetric substrate and incubated at 37° C. for 2 hours. The final concentration of added plasmin ranged between 0 and 15 nM. The absorbance was measured at 405 and 490 nm every 2 min using a plate reader (Spectra Max M2, Molecular Devices, USA). The absorbance at 490 nm was subtracted from the absorbance at 405 nm and plotted versus time. Rate of change in absorbance (410 nm-490 nm) between 20 and 120 minutes was calculated for each added plasmin concentration.

The concentration of endogenous plasmin was determined using the commercial assay. 50 μL of pre-treated raw milk was mixed with 5 μL plasmin cleavage buffer (10 nM) and 45 μL of colourimetric substrate and incubated at 37° C. for 2 hours. The absorbance was measured at 405 and 490 nm every 2 min using a plate reader (Spectra Max M2, Molecular Devices, USA). The absorbance at 490 nm was subtracted from the absorbance at 405 nm and plotted versus time. Rate of change in absorbance (410 nm-490 nm) between 20 and 120 minutes was calculated for each sample. Concentrations calculated from the calibration curve are multiplied by a dilution factor of 2.5.

Results
BRET$^2$ Plasmin Sensor

Initial attempts to determine plasmin concentrations in raw milk without a pre-treatment step were unsuccessful.

Calibration curves for the BRET$^2$ plasmin sensor were constructed for samples which had been prepared following the pre-treatment protocol of Rauh et al. (2014) and spiked with human plasmin (FIG. 11). The EC$_{50}$ is 19.48 nM. Endogenous plasmin concentrations measured in the pre-treated raw milk samples ranged from 2.1 nM to 4.4 nM (Table 4) with endogenous plasmin concentrations not detectable in three of the samples.

Colourimetric Substrate

Calibration curves for the colourimetric substrate, D-Val-Leu-Lys-4-nitroanilide dihydrochloride, were constructed for raw milk samples following the pre-treatment protocol of Rauh et al. (2014) and spiked with human plasmin (FIG. 12). Endogenous plasmin concentrations measured in the raw milk samples ranged from 2.1 nM to 2.9 nM following the original Rauh pre-treatment protocol (Table 4).

Example 5

Materials and Methods
Two Step Pre-Treatment Protocol

The pre-treatment protocol described in Example 4 was modified by adding EACA and NaCl to the tri-sodium citrate buffer and combining the two, 15 minute incubation steps. Briefly, 1 mL of the sonicated raw milk was mixed with 250 μL tri-sodium citrate buffer (pH 8.9) containing 5 mM EACA and 0.25 M NaCl. The sample was then incubated for 15 minutes at room temperature.

TABLE 4

Measurement of free endogenous plasmin in raw milk samples following the pre-treatment protocol of Rauh et al. (2014). The pre-treated sample was incubated for 10 minutes when using the BRET$^2$ plasmin sensor or for 120 minutes with colourimetic substrate (D-Val-Leu-Lys-4-nitroanilide dihydrochloride).

| | [Free endogenous plasmin] (nM) | |
|---|---|---|
| Sample ID | BRET$^2$ plasmin sensor | Colourimetric substrate |
| 1 | ND | 2.3 |
| 2 | ND | 2.6 |
| 3 | ND | 2.7 |
| 4 | 2.1 | 2.6 |
| 5 | 2.4 | 2.1 |
| 6 | 4.4 | 2.9 |

ND = not detectable.

Calibration Curves

The calibration curves for the BRET$^2$ plasmin sensor and the colourimetric substrate were determined as described in Example 4.

Determination of Endogenous Plasmin Concentration

The amount of plasmin present in the raw milk sample was determined as described in Example 4. The amount of plasmin present in the raw milk sample was validated using the colourimetric substrate, D-Val-Leu-Lys-4-nitroanilide dihydrochloride, as described in Example 4.

Results
BRET$^2$ Plasmin Sensor

Calibration curves were constructed for the BRET$^2$ plasmin sensor using raw milk samples spiked with human plasmin and following the two-step pre-treatment protocol. The EC$_{50}$ is 16.04 nM (FIG. 13). Endogenous plasmin concentrations measured in the raw milk samples ranged from 5.8 nM to 9.0 nM (Table 5).

Colourimetric Substrate

Calibration curves were constructed for the colourimetric substrate using raw milk samples treated by the two-step pre-treatment protocol and spiked with human plasmin and (FIG. 14). Endogenous plasmin concentrations measured in the raw milk samples ranged from 9.7 nm to 10.9 nM following the two-step pre-treatment protocol (Table 5).

TABLE 5

Measurement of free endogenous plasmin in raw
milk samples following two step pre-treatment using the BRET$^2$
plasmin sensor and the colourimetric substrate, D-Val-Leu-
Lys-4-nitroanilide dihydrochloride, (mean ± SD, n = 3).
The pre-treated sample was incubated for 10 minutes when
using the BRET$^2$ plasmin sensor or for 120 minutes with
colourimetic substrate (D-Val-Leu-Lys-4-nitroanilide dihydrochloride).

| | [Free endogenous plasmin] (nM) | |
|---|---|---|
| Sample ID | BRET$^2$ plasmin sensor | Colourimetric substrate |
| 1 | 6.8 ± 1.4 | 9.7 ± 1.1 |
| 2 | 5.8 ± 1.5 | 10.0 ± 0.8 |
| 3 | 8.2 ± 1.1 | 10.9 ± 2.4 |
| 4 | 6.4 ± 1.7 | 10.4 ± 0.6 |
| 5 | 8.5 ± 0.7 | 9.7 ± 0 |
| 6 | 9.0 ± 1.1 | 10.4 ± 0.6 |

TABLE 6

Measurement of free endogenous plasmin in raw milk samples
following one-step pre-treatment using the BRET$^2$ plasmin
sensor and the colourimetric substrate, D-Val-Leu-Lys-4-nitroanilide
dihydrochloride (mean ± SD, n = 3). The pre-treated sample
was incubated for 10 minutes when using the BRET$^2$ plasmin
sensor or for 120 minutes with colourimetic substrate (D-
Val-Leu-Lys-4-nitroanilide dihydrochloride).

| | [Free endogenous plasmin] (nM) | |
|---|---|---|
| Sample ID | BRET$^2$ plasmin sensor | Colourimetric substrate |
| 1 | 20.9 ± 3.7 | 17.2 ± 0.9 |
| 2 | 23.6 ± 0.7 | 17.2 ± 0.5 |
| 3 | 21.2 ± 1.7 | 18.0 ± 0.6 |
| 4 | 22.6 ± 3.2 | 17.6 ± 0.2 |
| 5 | 22.8 ± 2.0 | 17.2 ± 0.7 |
| 6 | 22.3 ± 1.6 | 17.6 ± 0.9 |

Example 6

Materials and Methods
One-Step Pre-Treatment Protocol

The pre-treatment protocol described in Example 5 was modified by combining the sonication and incubation steps to facilitate release of free plasmin. Briefly, 1 mL raw milk was mixed with 250 µL 0.4 M tri-sodium citrate buffer (pH 8.9 containing 5 mM EACA and 0.25 M NaCl) and the sample was sonicated (Misonix sonicator 3000; sample pulsar on, 0.5 seconds; pulsar off, 2.5 seconds; power 5.5) for 12 minutes.

Calibration Curves

The calibration curves for the BRET$^2$ plasmin sensor and the colourimetric substrate were determined as described in Example 4.

Determination of Endogenous Plasmin Concentration

The amount of plasmin present in the raw milk sample was determined as described in Example 4. The amount of plasmin present in the raw milk sample was validated using the colourimetric substrate, D-Val-Leu-Lys-4-nitroanilide dihydrochloride, as described in Example 4.

Results
BRET$^2$ Plasmin Sensor

Calibration curves for the BRET$^2$ plasmin sensor were constructed for raw milk samples which were spiked with human plasmin following the one-step pre-treatment protocol. The calibration curve is shown in FIG. 15. The EC$_{50}$ is 24.2 nM with a linear response being observed between 1.6 nM (90%) and 128 nM (10%) plasmin.

The endogenous plasmin concentrations measured in the raw milk samples ranged from 20.9 nM to 23.1 nM (Table 6). The lowest plasmin concentration measured in the milk samples was 18.2 nM with a BRET$^2$ response of 77.1% and the highest was 25.7 nM with a BRET$^2$ response of 66.7% both well within the linear range of the assay.

Colourimetric Substrate

Calibration curves for the colourimetric substrate, D-Val-Leu-Lys-4-nitroanilide dihydrochloride, were constructed for raw milk samples which were spiked with human plasmin following the one-step pre-treatment protocol. The calibration curve is shown in FIG. 16.

The EC$_{50}$ for the colourimetric assay was 11.06 nM with a linear response between 5.70 nM (10%) and 13.70 nM (90%). This is a much narrower range than observed with the BRET$^2$ plasmin sensor calibration results.

The endogenous plasmin concentrations measured in the raw milk samples ranged from 17.2 nM to 18.0 nM (Table 6).

Example 7

Materials and Methods
One-Step Pre-Treatment Protocol with Low Power Sonication

The pre-treatment protocol described in Example 6 was modified further by replacing the sonicator (Misonix sonicator 3000) with a lower power sonicator that can be used continuously (Q55 Sonicator, Daintree Scientific). Briefly, 1 mL raw milk was mixed with 250 µL 0.4 M tri-sodium citrate buffer (pH 8.9 containing 5 mM EACA and 0.25 M NaCl). The sample was sonicated (Q55 sonicator, amplitude set at 40) continuously for 2 minutes on ice.

Calibration Curve

The calibration curve was determined as described in example 4.

Determination of Endogenous Plasmin Concentration

The amount of plasmin present in the raw milk sample was determined as described in example 4.

Results

Calibration curves for the BRET$^2$ plasmin sensor were constructed for raw milk samples which have been spiked with human plasmin following the one-step pre-treatment protocol with low power sonication. The calibration curve is shown in FIG. 17. The calculated EC$_{50}$ is 29.3 nM and the response is linear between 5.5 nM (90%) and 107 nM (10%).

Endogenous plasmin concentrations measured in the raw milk samples following one-step pre-treatment with low power sonication ranged from 12.0 nM to 17.2 nM with BRET$^2$ responses ranging between 87.1% and 91.4% for the six samples (Table 7).

Discussion

The data from Examples 4 to 7 shows that the incorporating sonication into the pre-treatment protocol had a profound positive effect on the sensitivity of the assay and the amount of free endogenous plasmin measured in the milk sample (Table 8). For example, using the one-step pre-treatment protocol increased the levels of free endogenous plasmin measured by a factor of 5-10 compared to the pre-treatment method of Rauh et al. (2014). This was validated using the colourimetric substrate assay. For both the BRET and colourimetric assays, endogenous free plasmin levels measured in raw milk were 2-3 times higher when the one-step protocol was used in place of the two step pre-treatment. Incorporating a low-power sonication increased endogenous free plasmin levels measured in raw milk by a factor 4-6 times compared to the pre-treatment method of Rauh et al. (2014) while simultaneously reducing the total assay time from a 50 minutes assay time for the original method compared to a 12 minutes assay time for the low power sonication pre-treatment. The data show that sonicating the sample in the presence of EACA significantly increases the efficiency of the dissociation of endogenous plasmin from casein.

TABLE 7

Measurement of free endogenous plasmin in raw milk samples following one-step pre-treatment with low power sonication with the BRET$^2$ plasmin sensor, (mean ± SD, n = 3).

| Sample ID | [Free endogenous plasmin] (nM) |
|---|---|
| 1 | 12.0 ± 0.6 |
| 2 | 12.5 ± 1.9 |
| 3 | 17.3 ± 0.4 |
| 4 | 17.2 ± 2.3 |
| 5 | 16.8 ± 0.9 |
| 6 | 15.6 ± 1.5 |

TABLE 8

Comparison of free endogenous plasmin concentration range (nM) measured in six "high quality" raw milk samples following the original Rauh pre-treatment protocol, two-step pre-treatment, one-step pre-treatment and one-step pre-treatment with low power sonication (one-step rapid). Total assay time includes homogenisation time (12 minutes for two- and one-step and 2 minutes for one-step rapid), pre-treatment incubation times and a 10 minute incubation assay time.

| | Pre-treatment protocol | | | |
|---|---|---|---|---|
| | Rauh et al. (2014) | Two-step | One-step | One-step rapid |
| Measured Plasmin (nM) | 2.1-4.4 | 5.8-9.0 | 20.9-22.6 | 12-17.2 |
| Total assay time (mins.) | 50 | 32 | 22 | 12 |

Example 8

Materials and Methods

The Pflu1 sensor was used here for measuring bacterial proteases in raw milk. Pre-treated raw milk samples were prepared as described in Example 7 with the exception that the samples were sonicated for 4 minutes.

Calibration Curve

In order to generate a calibration curve, aliquots of the pre-treated raw milk samples were heated to 55° C. for 1 hr followed by 90° C. for 30 s to deactivate any endogenous bacterial proteases and endogenous plasmin. The heated pre-treated samples were spiked with varying amounts of the crude bacterial protease fraction (see Example 2 for preparation) by adding 10 µL bacterial proteases to 50 µL of the heated milk sample. The final concentration of added bacterial proteases ranged between 1 pM and 10 nM. 5 µL BRET$^2$ Pflu1 sensor (10 nM) and 30 µL plasmin cleavage buffer was added to the spiked sample and the sample was mixed well by pipetting. The samples were incubated for 10 minutes at 28° C. Following the incubation, 5 µL of Clz400a substrate (100 µM) was added to the well and the BRET ratio was recorded as described above.

Determination of Bacterial Protease Concentration

To determine the amount of bacterial protease present in the raw milk sample, 50 µL of the pre-treated raw milk samples were mixed with 5 µL Pflu1 sensor (10 nM) and 40 µL plasmin cleavage buffer in a microplate well. The mixture was incubated for two hours at 28° C. Following incubation, 5 µL Clz400a substrate (100 µM) was added to the well and the BRET ratio was recorded. Concentrations calculated from the calibration curve were multiplied by a dilution factor of 2.5.

Results

Calibration curves were constructed for raw milk samples following pre-treatment and the Pflu1 sensor. The calibration curve is shown in FIG. 18. The $EC_{50}$ is 0.4 nM and the response is linear between 48.2 pM (90%) and 2.6 nM (10%). Levels of bacterial proteases measured in the raw milk samples following a rapid one-step pre-treatment protocol were mostly present at sub picomolar concentrations, at or below the limit of detection of our current generation of CYBERTONGUE® bacterial protease sensors (the limit of detection is currently estimated to be 1 pM). All but two of the raw milk samples had no detectable bacterial protease (FIG. 19). In the samples where endogenous bacterial protease could be measured, the concentration ranged from 1.4 pM to 3.4 pM (FIG. 19).

Example 9

Materials and Methods

The Pflu1 sensor was used here for measuring bacterial proteases in raw milk without any pre-treatment of the raw milk sample.

Calibration Curve

In order to generate a calibration curve, aliquots of the pre-treated raw milk samples were heated to 55° C. for 1 hr to deactivate any endogenous bacterial proteases. The heated pre-treated samples were spiked with varying amounts of the crude bacterial protease fraction (see Example 2 for preparation) by adding 10 µL bacterial proteases to 50 µL of the heated milk sample. The final concentration of added bacterial proteases ranged between 1 pM and 10 nM. 5 µL BRET$^2$ Pflu1 sensor (10 nM) and 30 µL plasmin cleavage buffer was added to the spiked sample and the sample was mixed well by pipetting. The samples were incubated for 10 minutes or 2 hours at 28° C. with and without pre-treatment (one-step pre-treatment protocol with low power sonication). Following the incubation, 5 µL of Clz400a substrate (100 µM) was added to the well and the BRET ratio was recorded as described above.

Results

It appears that the bacterial protease sensor has similar response and sensitivity to bacterial proteases without any pre-treatment of the raw milk following a 10 minute incubation time of the sensor with the bacterial protease compared to the same sensor calibrated in raw milk which had been pre-treated (using the one-step pre-treatment protocol with low power sonication for 4 minutes) following a 2 hr incubation period (FIGS. 20 to 22, Table 9).

The lowest detection of bacterial protease (3.94 pM) was achieved with no pre-treatment following a 2 hr incubation time. This demonstrates that longer incubation times result in lower detection limit. It is predicted that increasing the incubation times even further would enable even lower (sub pM) concentrations of bacterial proteases to be detected. Comparing the results to the plasmin sensor response to bacterial proteases in raw milk (FIG. 6 and Table 3) the Pflu1 sensor is 10× more sensitive to bacterial proteases than the plasmin sensor with a 10 minute incubation time in raw milk.

TABLE 9

EC$_{50}$ and linear range calculated in 50% raw milk spiked with crude protease for different incubation times with or without one-step pre-treatment protocol with low power sonication for 4 minutes. Linear range defined as range between 10% and 90% BRET$^2$ response.

| | Assay conditions | | | |
|---|---|---|---|---|
| | No pre-treatment | | Pre-treatment | |
| | Incubation time | | | |
| | 10 mins. | 2 hrs | 10 mins. | 2 hrs |
| Linear range (pM) | 15.74-1256 | 3.94-290 | 48.2-2580 | 14.80-670 |
| EC$_{50}$ (pM) | 140 | 33.9 | 353 | 100 |

Example 10

To determine if Pflu 1 sensor can respond to more than one *P. fluorescens* strain the inventors produced a crude extract of bacterial protease from *P. fluorescens* strain 117.

Materials and Methods

Crude extract was prepared from skimmed milk innoculated with *P. fluorescens* strain 117 using the methods described in Example 2.

SDS-PAGE (FIG. 23) analysis of the crude extract prepared from skimmed milk innoculated with *P. fluorescens* (strain 117) demonstrated the presence of a dominant band between 46 and 58 kDa, which is consistent with the molecular mass of 50 KDa that characterises a class of zinc-dependent metalloproteases (AprX proteases) produced by a number of different *P. fluorescens* strains in milk (Dacres et al., 2014; Button et al., 2011) including strain 65 (FIG. 3). The concentration of protease secreted by *P. fluorescens* strain 117 was estimated to be 0.32 µM by densitometric analysis of stained bands and when compared to marker 46 KDa (color protein standard, Broad Range #P7712S Lot:0021410, BioLaban) SDS-PAGE gel.

Detection of Bacterial Protease from *P. fluorescens* (Strain 117)

Cleavage buffer and UHT milk were spiked with 1 nM of bacterial protease produced from either strain 65 or 117 and the responses compared to a control without the addition of any bacterial protease. Crude bacterial protease was prepared as described in Example 2. The protease assay was performed as described in Example 2 using 10 nM purified sensor.

Results

Bacterial proteases produced from *P. fluorescens* strains 65 and 117 completely cleaved the Plu1 sensor within a 10 minute incubation time in buffer (FIG. 24) resulting in 95% reduction in the BRET ratio. When the assay was carried out in UHT milk spiked with 1 nM bacterial protease there was 80.6% reduction in the BRET ratio with strain 65 bacterial proteases compared to a 71.2% reduction with the bacterial protease from strain 117. This demonstrates that the Pflu 1 sensor is able to respond to bacterial proteases produced from different *P. fluorescens* strains.

Example 11

The Pflu 1-3 sensor series comprised BRET components separated by linker sequences with a central F-M cleavage site (FIG. 1) to incorporate cleavage sites and polypeptide sequences found in κ-casein. A second set of protease sensors was designed to incorporate the most predominant amino acids found in the P4 to P4' positions for all cleavage sites found in all caseins (Pflu H1-4).

Materials and Methods

Construction of New Bacterial Protease Sensors

DNA constructs encoding the BRET$^2$-bacterial protease Pflu sensors H1, H2, H3 and H4 were synthesised by GenScript (USA). The sensors comprised Rluc2 as the chemiluminescent donor and a variant of green fluorescent protein (GFP$^2$) as the acceptors separated by linkers (Table 10). The constructs were cloned into a pRSET vector (Bio-Labs, Australia) to make a pRSET-Pflu H vector encoding the protease sensor. The polynucleotide sequences encoding the protease sensors are shown in SEQ ID NO's:116 to 119. The polypeptide sequence of the protease sensors are shown in SEQ ID NO's:120 to 123. Purified sensor was produced using the methods described in Example 1.

Calibration Curves and Protease Assays

Methods for the calibration curves and protease assays for the new bacterial protease sensors (Pflu-H1-H4) are described in Example 2.

TABLE 10

Linker sequences separating BRET components in H1-H4 sensors.

| Bacterial protease sensor | Linker sequence |
|---|---|
| Pflu-H1 | LQGSPPLKQPPPGSFE (SEQ ID NO: 113) |
| Pflu-H2 | LQGSPPLQQPQPGSFE (SEQ ID NO: 114) |
| Pflu-H3 | LQGSKQKQKQKQGSFE (SEQ ID NO: 112) |
| Pflu-H4 | LQGGSGGSLKQQGGSGGSFE (SEQ ID NO: 115) |

Results

All four new bacterial protease sensors (Pflu H1-H4) responsed significantly (P=0.05) to 1 nM bacterial protease in buffer (FIG. 26). The relative sensitivity of the sensors was H3>H4>H1>H2 with the responses of 89.7%, 64.5%, 49.5% and 31.9%, respectively. This demonstrates that Pflu H3 sensor had the most sensitive response to bacterial protease being 39%, 82% and 182% more responsive to 1 nM bacterial protease compared to the respective responses of Pflu H4, Pflu H1 and Pflu H2 sensors.

To assess the selectivity of Pflu1 H1-H4 sensors for bacterial protease compared to plasmin in milk we compared the response of the Pflu1 H1-H4 sensors to UHT milk spiked with either 1 nM plasmin or bacterial protease (FIGS. 27-30 and Table 11).

TABLE 11

BRET$^2$ response (%) of Pflu-H1-H4 sensor series to 1 nM of crude bacterial protease from *P. fluorescens* strains 65 or 1 nM Bovine plasmin in UHT milk. Selectivity is calculated as ratio of Bacterial protease response to Plasmin response.

| Sensor | Plasmin response (%) | Bacterial protease response (%) | Selectivity |
|---|---|---|---|
| Pflu-H1 | 4.9 | 6.7 | 1.3 |
| Pflu-H2 | 7.9 | 6.6 | 0.8 |
| Pflu-H3 | 0.9 | 36.3 | 40.3 |
| Pflu-H4 | 6.3 | 17.1 | 2.7 |

Pflu-H3 sensor was the most selective for detecting bacterial protease over plasmin with a selectivity factor of 40 in UHT milk. This was followed by Pflu-H4 sensor which was 2.7× more selective for bacterial protease than plasmin. Pflu-H1 was 1.3× more selective for bacterial protease than plasmin. Pflu-H2 was the least selective for bacterial proteases being more selective for plasmin with a selectivity factor of 0.8.

As Pflu-H3 was the most selective and sensitive for detecting bacterial proteases in milk further analysis was carried out using this sensor in raw milk. Calibration curves were plotted for bacterial proteases (strain 65) and Bovine plasmin as shown in FIG. 31. The Pflu-H3 sensor had an $EC_{50}$ of 0.5 nM for bacterial proteases and 173.9 nM for bovine plasmin (Table 3). The Pflu H3 sensor is therefore approximately 376× more sensitive to the bacterial proteases than to Bovine plasmin in raw milk.

Example 12

In Example 2 and 10 the bacterial protease concentration was estimated using densitometry and comparing the relative density of the bacterial protease band on SDS-PAGE to the 46 kDa band of the marker band (color protein standard, Broad Range #P7712S Lot:0021410, BioLaban). The inventors investigated a different approach to determine bacterial protease concentration by comparing the relative density of the bacterial protease to known concentrations of BSA.

Materials and Methods

Crude extract was prepared from skimmed milk inoculated with *P. fluorescens* strain 65 and 117 using the methods described in Example 2 and 10. SDS-PAGE analysis of two extracts of strain 65 (65-1 and 65-2) and strain 117 and different concentrations of BSA was carried out (FIG. 32). Strain 65-1 is the extract used for all examples herein which have used bacterial proteases from strain 65. Strain 117 is the extract used in Example 10. Novex #LC5625 SeeBlue Pre-stained Standard was the commercial marker used. Densitometric analysis of proteins on SDS-PAGE was carried out using Image Quant TL (GE Healthcare) and bacterial protease concentrations estimated from the BSA calibration curve (FIG. 33). The calibration graph was plotted using GraphPad Prism (Version 7) by fitting a linear regression analysis.

Results

The line of best fit for the BSA calibration graph was determined to be y=107235+79.66x, R2=0.9679 (FIG. 32). Bacterial protease concentrations for extract 65-1, 65-2 and 117, respectively, were determined to be 3.94, 2.37 and 3.37 µM, respectively. The previous method used to determine concentration of the same batch of strain 65-1 and strain 117 in Example 2 and 10 estimated concentrations of 0.34 µM and 0.32 µM, respectively. Using the current approach for concentration determination results in the concentration of bacterial protease being 11.6× higher for strain 65 (65-1) and 10.5× higher for strain 117. As an example of the effect of this on the sensitivity of the Pflu1 sensor the correction factor 11.6 was used to correct all bacterial protease concentrations used to plot FIG. 7 resulting in an EC50 of 8.2 nM and linear range of 1.4-45 nM (FIG. 34 and Table 12) which are 11.6 higher than those presented in Table 3. The correction factors for the bacterial protease concentrations were applied to all values presented originally in Table 3 for bacterial protease measurements (Table 12).

Using this approach to estimate bacterial protease concentration has the impact of reducing the selectivity of the bacterial protease sensors for bacterial proteases over Human or Bovine plasmin. For example, the lowest selectivity for bacterial protease (over Human plasmin) was 15 for Pflu 1 sensor reduced from 174 and the highest is 48.5 with Pflu 3 sensor compared to the original selectivity factor of 563. Application of the correction factor to the plasmin sensor response to bacterial proteases increases the selectivity factor for the plasmin sensor to detect plasmin over bacterial proteases (Table 12).

Using BSA as the standard to measure bacterial protease concentration in UHT milk all sensors with different target sequence give a combined linear range of 1.5-1044 nM compared to 0.1-90 nM bacterial proteases in UHT milk using the earlier method for concentration determination. In raw milk the combined linear range for bacterial protease measurement ranges from 0.2-110 nM (Table 12) compared to 0.01-9 nM (Table 3) for the two different methods of concentration determination.

If the calibration curves are corrected for bacterial protease concentration determined by the BSA method used in Example 8 to determine endogenous bacterial protease levels in raw milk, the concentration measured now ranges from 16.2 pM to 39.4 pM using the (FIG. 19).

TABLE 12

$EC_{50}$ and linear range calculated in 50% full fat milk spiked with crude protease. Linear range defined as range between 10% and 90% BRET[2] response. Selectivity factor (Bacterial protease: Plasmin) for bacterial protease sensors Pflu 1, Pflu 2 Pflu 3, Pflu-H3 and plasmin sensor. Bacterial protease determined by comparison to BSA standard.

| Target sequence | Sensor | [Human plasmin] (nM) | | [Bovine plasmin] (nM) | | [Bacterial protease] (nM) | | Selectivity for bacterial protease over human plasmin (fold) | Selectivity for bacterial protease over bovine plasmin (fold) |
|---|---|---|---|---|---|---|---|---|---|
| | | $EC_{50}$ | Linear range | $EC_{50}$ | Linear range | $EC_{50}$ | Linear range | | |
| LQGSKKYKVKEGSLQ (SEQ ID NO: 110) | Plasmin | 5.6 | 0.7-43 | 108 | 32-367 | ~580 16.2* | 116-1044 2.4-110* | 0.01 | 0.2 |
| LQGSFMKKNQNTEIGSFE (SEQ ID NO: 72) | Pflu 1 | 124 | 10-1401 | 169 | 53-537 | 8.2 1.63* 2.6*[1] | 1.5-45 0.2-14.5* 0.2-33.2*[1] | 15 | 20 |
| LQGSFMNQNTEIGSFE (SEQ ID NO: 73) | Pflu 2 | 926 | 233-3680 | n.d. | n.d. | 30.4 | 6.7-13.8 | 30 | N.D. |
| LQGSLSFMAIPGSFE (SEQ ID NO: 74) | Pflu 3 | 1280 | 452-3622 | n.d. | n.d. | 26.4 | 5.5-125.8 | 48.5 | N.D. |
| LQGSKQKQKQKQGSFE (SEQ ID NO: 112) | Pflu-H3 | n.d. | n.d. | 174* | 28-1079* | 5.4* | 0.4-78.9* | N.D.* | 32 |

N.D. = not determined, *indicates values were calculated in raw milk samples, [1]indicates response to bacterial protease from strain 117 all other responses are for bacterial proteases from strain 65.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The present application claims priority from AU 2016904639 filed 14 Nov. 2016 and AU 2017900161 filed 19 Jan. 2017, the entire contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Bagshaw (2001) J. of Cell Science 114:459-460
Benslimane et al. (2009) Journal of Dairy Research 57: 423-435.
Bryce et al. (2016) Sensors 16: 1488.
Button et al. (2011) Journal of Food Quality 34:229-235.
Dacres et al. (2009) Biosensors and Bioelectronics 24:1164-1170.
Dacres et al. (2014) Poster presentation. Biosensors 2014, May 27-30th 2014, Melbourne.
Datta and Deeth (2001) Trans. Instit. Chem. Eng (Part C). 79:197-210
Day et al. (2004) Luminescence 19:8-20.
de Wet et al. (1987) Mol. Cell. Biol. 2987:725-737.
Dupont et al. (1997) Journal of Dairy Research. 64:77-86.
Dupont et al. (2007) Journal of Agriculture and Food Chemistry. 55: 6857-6862.
Forster (1948) Ann. Physik. 2:55
Forster (1960) Rad. Res. Suppl., 2:326,
Greer and Szalay (2002) Luminescence 17:43-74.
Guarise et al. (2006) PNAS, 103:3978-3982.
Hastings (1996) Gene 173:5-11.
Hushpulian et al. (2007) Biol. Chem. 388:373-380.
Inouye and Shimomura (1997) Biochem Biophys Res Commun. 233:349-353.
Kim and Kim (2012) Theranostics, 2:127-138.
Loening et al. (2006) Protein Eng. Des. Sel. 19:391-400.
Loening et al. (2007) Nature Methods 4:641-643.
Lorenz et al. (1991) Proc. Natl. Acad. Sci. USA 88:4438-4442.
Martins (2015) Brazilian Journal of Microbiology, http://dx.doi.org/10.1590/S1517-838246120130859.
Rauh et al. (2014) Int. Dairy J. 38:74-80.
Saint-Denis et al. (2001) J. Dairy Res. 68:437-449.
Sapsford et al. (2006) Angew. Chemie. Int. Ed. 45:4562-4588.
Tsien (1998) Ann. Rev. Biochem. 63:509-544.
Verhaegen et al. (2002) Anal. Chem. 74: 4378-4385
Viviani (2002) Cell. Mol. Life Sci. 59:1833-1850.
Wang et al. (1997) in Bioluminescence and Chemiluminescence: Molecular Reporting with Photons, eds. Hastings et al. (Wiley, New York), pp. 419-422.
Xu et al. (1999) Proc. Natl. Acad. Sci. USA. 96:151-156.
Zhang and Lv (2014) J Food Sci Technol. 51:1185-119.

---

The invention claimed is:

1. A *Pseudomonas* spp. protease sensor molecule comprising:
   a target sequence comprising the amino acid sequence selected from SFMKKNQNTEI (SEQ ID NO: 45) and LQGSFMKKNQNTEIGSFE (SEQ ID NO: 72) and combinations thereof; and
   a chemiluminescent donor domain and an acceptor domain covalently attached to the target sequence,
   wherein cleavage of the target sequence by a *Pseudomonas* spp. protease produces a detectable change in resonance energy transfer.

2. The sensor of claim 1, wherein the target sequence comprises the amino acid sequence: SFMKKNQNTEI (SEQ ID NO: 45).

3. The sensor of claim 1, wherein
   the acceptor domain is green fluorescent protein (GFP), Venus, mOrange, or a biologically active variant or fragment of any one thereof;
   the chemiluminescent donor domain is a luciferase or a biologically active variant or fragment; and
   the target sequence comprises the amino acid sequence: SFMKKNQNTEI (SEQ ID NO: 45).

4. The sensor of claim 1 which
   i) has an $EC_{50}$ of between 0.1 and 10 nM, or between 0.1 and 100 nM, for a *Pseudomonas* spp. protease, and/or
   ii) is at least 20 times, or at least 100 times, more sensitive for a *Pseudomonas* spp. protease compared to bovine plasmin.

5. A method of detecting a *Pseudomonas* spp. infection in a sample, the method comprising:
   i) contacting the sample with the sensor of claim 1; and
   ii) detecting a change in the resonance energy transfer, wherein said change corresponds to the presence of a *Pseudomonas* spp. infection.

6. A method of detecting a *Pseudomonas* spp. protease in a sample, the method comprising
   i) contacting a sample with the sensor of claim 1; and
   ii) detecting a change in the resonance energy transfer, wherein said change corresponds to the presence of a *Pseudomonas* spp. protease in the sample.

7. A method of detecting spoilage of a dairy product, the method comprising
   i) contacting a sample of the dairy product with the sensor of claim 1; and
   ii) detecting a change in the resonance energy transfer, wherein said change indicates that the dairy product is spoilt, has begun to spoil or has the potential to spoil.

8. The method of claim 6, which
   i) detects at least 1 pM, or at least 10 pM, or at least 100 pm, of *Pseudomonas* spp. protease, and/or
   ii) is performed in less than 1 hour, less than 30 minutes or less than 15 minutes.

9. A composition comprising the sensor of claim 1, and one or more acceptable carrier(s).

10. The sensor of claim 1, wherein the target sequence comprises the amino acid sequence: LQGSFMKKNQNTEIGSFE (SEQ ID NO: 72).

11. The sensor of claim 1, wherein the target sequence further comprises the amino acid sequence: SKMXXPP (SEQ ID NO: 40), where X is any amino acid.

12. The sensor of claim 1, wherein
the acceptor domain is GFP²;
the chemiluminescent donor domain is a *Renilla* luciferase 2, *Renilla* luciferase 8 or *Renilla* luciferase 8.6-535; and
the target sequence comprises the amino acid sequence: SFMKKNQNTEI (SEQ ID NO: 45).

13. The sensor of claim 1, wherein the target sequence further comprises at least one *Pseudomonas* spp. protease cleavage site selected from the group consisting of KQ, SFM (SEQ ID NO: 37), KKNQ (SEQ ID NO: 24), NT, and EI and combinations thereof.

14. The sensor of claim 1, wherein:
the acceptor domain is green fluorescent protein (GFP), Venus, mOrange, or a biologically active variant or fragment of any one thereof;
the chemiluminescent donor domain is a luciferase or a biologically active variant or fragment; and
the target sequence comprises the amino acid sequence: LQGSFMKKNQNTEIGSFE (SEQ ID NO: 72).

15. The sensor of claim 1, wherein
the acceptor domain is GFP²;
the chemiluminescent donor domain is a *Renilla* luciferase 2, *Renilla* luciferase 8 or *Renilla* luciferase 8.6-535; and
the target sequence comprises the amino acid sequence: LQGSFMKKNQNTEIGSFE (SEQ ID NO: 72).

16. The sensor of claim 2, wherein the target sequence comprises an amino acid linker at an N- and/or C-terminus, wherein each linker independently comprises the amino acid sequence selected from the group consisting of LQG (SEQ ID NO: 95); GSFE (SEQ ID NO: 96); GSSGGS (SEQ ID NO: 97); GSPPL (SEQ ID NO: 98); PPPGS (SEQ ID NO: 99), GGSGGS (SEQ ID NO: 100, GGSGGSL (SEQ ID NO: 101) and PPVKQPPP (SEQ ID NO: 44).

* * * * *

SEQUENCE LISTING

```
<160> NUMBER OF SEQ ID NOS: 123

<210> SEQ ID NO 1
<211> LENGTH: 4
<212> TYPE: PRT
<213> ORGANISM: Artificial Sequence
<220> FEATURE:
<223> OTHER INFORMATION: protease sensor molecule

<400> SEQUENCE: 1

Lys Gln Lys Gln
1

<210> SEQ ID NO 2
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 2

Lys Gln Ser Phe
1

<210> SEQ ID NO 3
<211> LENGTH: 4
<212> TYPE: PRT
<213> ORGANISM: Artificial Sequence
<220> FEATURE:
<223> OTHER INFORMATION: Protease sensor molecule
```

```
<400> SEQUENCE: 3

Lys Gln Phe Met
1

<210> SEQ ID NO 4
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 4

Lys Gln Lys Lys
1

<210> SEQ ID NO 5
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 5

Lys Gln Lys Asn
1

<210> SEQ ID NO 6
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 6

Lys Gln Asn Gln
1

<210> SEQ ID NO 7
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 7

Lys Gln Asn Thr
1

<210> SEQ ID NO 8
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 8

Lys Gln Glu Ile
1

<210> SEQ ID NO 9
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 9
```

```
Ser Phe Ser Phe
1

<210> SEQ ID NO 10
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 10

Ser Phe Phe Met
1

<210> SEQ ID NO 11
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 11

Ser Phe Lys Lys
1

<210> SEQ ID NO 12
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 12

Ser Phe Lys Asn
1

<210> SEQ ID NO 13
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 13

Ser Phe Asn Gln
1

<210> SEQ ID NO 14
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 14

Ser Phe Asn Thr
1

<210> SEQ ID NO 15
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 15
```

Ser Phe Glu Ile
1

<210> SEQ ID NO 16
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 16

Phe Met Phe Met
1

<210> SEQ ID NO 17
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 17

Phe Met Lys Lys
1

<210> SEQ ID NO 18
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 18

Phe Met Lys Asn
1

<210> SEQ ID NO 19
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 19

Phe Met Asn Gln
1

<210> SEQ ID NO 20
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 20

Phe Met Asn Thr
1

<210> SEQ ID NO 21
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 21

Phe Met Glu Ile

```
<210> SEQ ID NO 22
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 22

Lys Lys Lys Lys
1

<210> SEQ ID NO 23
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 23

Lys Lys Lys Asn
1

<210> SEQ ID NO 24
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 24

Lys Lys Asn Gln
1

<210> SEQ ID NO 25
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 25

Lys Lys Asn Thr
1

<210> SEQ ID NO 26
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 26

Lys Lys Glu Ile
1

<210> SEQ ID NO 27
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 27

Lys Asn Lys Asn
1
```

<210> SEQ ID NO 28
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 28

Lys Asn Asn Gln
1

<210> SEQ ID NO 29
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 29

Lys Asn Asn Thr
1

<210> SEQ ID NO 30
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 30

Lys Asn Glu Ile
1

<210> SEQ ID NO 31
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 31

Lys Asn Phe Met
1

<210> SEQ ID NO 32
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 32

Lys Asn Lys Lys
1

<210> SEQ ID NO 33
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 33

Asn Gln Asn Gln
1

```
<210> SEQ ID NO 34
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 34

Asn Thr Asn Thr
1

<210> SEQ ID NO 35
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 35

Asn Thr Glu Ile
1

<210> SEQ ID NO 36
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 36

Glu Ile Glu Ile
1

<210> SEQ ID NO 37
<211> LENGTH: 3
<212> TYPE: PRT
<213> ORGANISM: Artificial Sequence
<220> FEATURE:
<223> OTHER INFORMATION: Protease sensor molecule

<400> SEQUENCE: 37

Ser Phe Met
1

<210> SEQ ID NO 38
<211> LENGTH: 7
<212> TYPE: PRT
<213> ORGANISM: Artificial Sequence
<220> FEATURE:
<223> OTHER INFORMATION: Protease sensor molecule

<400> SEQUENCE: 38

Ser Phe Met Lys Lys Asn Gln
1               5

<210> SEQ ID NO 39
<211> LENGTH: 7
<212> TYPE: PRT
<213> ORGANISM: Artificial Sequence
<220> FEATURE:
<223> OTHER INFORMATION: Protease sensor molecule

<400> SEQUENCE: 39

Lys Lys Asn Gln Ser Phe Met
1               5
```

```
<210> SEQ ID NO 40
<211> LENGTH: 7
<212> TYPE: PRT
<213> ORGANISM: Artificial Sequence
<220> FEATURE:
<223> OTHER INFORMATION: Protease sensor molecule
<220> FEATURE:
<221> NAME/KEY: X
<222> LOCATION: (4)..(5)
<223> OTHER INFORMATION: X can be any amino acid

<400> SEQUENCE: 40

Ser Lys Met Xaa Xaa Pro Pro
1               5

<210> SEQ ID NO 41
<211> LENGTH: 12
<212> TYPE: PRT
<213> ORGANISM: Artificial Sequence
<220> FEATURE:
<223> OTHER INFORMATION: Protease sensor molecule
<220> FEATURE:
<221> NAME/KEY: X
<222> LOCATION: (3)..(5)
<223> OTHER INFORMATION: X can be any amino acid
<220> FEATURE:
<221> NAME/KEY: X
<222> LOCATION: (9)..(10)
<223> OTHER INFORMATION: X can be any amino acid

<400> SEQUENCE: 41

Pro Pro Xaa Xaa Xaa Ser Lys Met Xaa Xaa Pro Pro
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Protease sensor molecule
<220> FEATURE:
<221> NAME/KEY: X
<222> LOCATION: (3)..(4)
<223> OTHER INFORMATION: X can be any amino acid
<220> FEATURE:
<221> NAME/KEY: X
<222> LOCATION: (8)..(9)
<223> OTHER INFORMATION: X can be any amino acid

<400> SEQUENCE: 42

Pro Pro Xaa Xaa Ser Lys Met Xaa Xaa Pro Pro
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Protease sensor molecule
<220> FEATURE:
<221> NAME/KEY: X
<222> LOCATION: (3)..(3)
<223> OTHER INFORMATION: X can be any amino acid
<220> FEATURE:
<221> NAME/KEY: X
<222> LOCATION: (7)..(8)
<223> OTHER INFORMATION: X can be any amino acid

<400> SEQUENCE: 43

Pro Pro Xaa Ser Lys Met Xaa Xaa Pro Pro
1               5                   10
```

```
<210> SEQ ID NO 44
<211> LENGTH: 8
<212> TYPE: PRT
<213> ORGANISM: Artificial Sequence
<220> FEATURE:
<223> OTHER INFORMATION: Protease sensor molecule

<400> SEQUENCE: 44

Pro Pro Val Lys Gln Pro Pro Pro
1               5

<210> SEQ ID NO 45
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 45

Ser Phe Met Lys Lys Asn Gln Asn Thr Glu Ile
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 46

Ser Phe Met Asn Thr Lys Lys Asn Gln Glu Ile
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 47

Ser Phe Met Gln Asn Thr Glu Ile Lys Lys Asn
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 48

Ser Phe Met Asn Gln Lys Lys Asn Thr Glu Ile
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 49

Ser Phe Met Asn Gln Asn Thr Lys Lys Glu Ile
1               5                   10
```

```
<210> SEQ ID NO 50
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 50

Ser Phe Met Asn Gln Asn Thr Glu Ile Lys Lys
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 51

Lys Lys Asn Gln Ser Phe Met Asn Thr Glu Ile
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 52

Lys Lys Asn Gln Asn Thr Ser Phe Met Glu Ile
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 53

Lys Lys Asn Gln Asn Thr Glu Ile Ser Phe Met
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 54

Lys Lys Ser Phe Met Asn Gln Asn Thr Glu Ile
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 55

Lys Lys Asn Gln Ser Phe Met Glu Ile Asn Thr
1               5                   10

<210> SEQ ID NO 56
```

```
<211> LENGTH: 11
<212> TYPE: PRT
<213> ORGANISM: Artificial Sequence
<220> FEATURE:
<223> OTHER INFORMATION: Protease sensor molecule

<400> SEQUENCE: 56

Lys Lys Asn Gln Glu Ile Ser Phe Met Asn Thr
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 57

Ser Phe Met Asn Gln Asn Thr Glu Ile
1               5

<210> SEQ ID NO 58
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 58

Asn Gln Ser Phe Met Asn Thr Glu Ile
1               5

<210> SEQ ID NO 59
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 59

Asn Gln Asn Thr Ser Phe Met Glu Ile
1               5

<210> SEQ ID NO 60
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 60

Asn Gln Asn Thr Glu Ile Ser Phe Met
1               5

<210> SEQ ID NO 61
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 61

Ser Phe Met Asn Thr Asn Gln Glu Ile
1               5

<210> SEQ ID NO 62
<211> LENGTH: 9
```

```
<212> TYPE: PRT
<213> ORGANISM: Artificial Sequence
<220> FEATURE:
<223> OTHER INFORMATION: Protease sensor molecule

<400> SEQUENCE: 62

Ser Phe Met Asn Thr Glu Ile Asn Gln
1               5

<210> SEQ ID NO 63
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 63

Ser Phe Met Asn Gln Glu Ile Asn Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 64

Asn Gln Ser Phe Met Glu Ile Asn Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 65

Asn Gln Glu Ile Ser Phe Met Asn Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 66

Ser Phe Met Glu Ile Asn Gln Asn Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 67

Glu Ile Ser Phe Met Asn Thr Asn Gln
1               5

<210> SEQ ID NO 68
<211> LENGTH: 9
<212> TYPE: PRT
```

<213> ORGANISM: Artificial Sequence
<220> FEATURE:
<223> OTHER INFORMATION: Protease sensor molecule

<400> SEQUENCE: 68

Glu Ile Asn Thr Ser Phe Met Asn Gln
1               5

<210> SEQ ID NO 69
<211> LENGTH: 9
<212> TYPE: PRT
<213> ORGANISM: Artificial Sequence
<220> FEATURE:
<223> OTHER INFORMATION: Protease sensor molecule

<400> SEQUENCE: 69

Glu Ile Asn Thr Asn Gln Ser Phe Met
1               5

<210> SEQ ID NO 70
<211> LENGTH: 7
<212> TYPE: PRT
<213> ORGANISM: Artificial Sequence
<220> FEATURE:
<223> OTHER INFORMATION: Protease sensor molecule

<400> SEQUENCE: 70

Leu Ser Phe Met Ala Ile Pro
1               5

<210> SEQ ID NO 71
<211> LENGTH: 8
<212> TYPE: PRT
<213> ORGANISM: Artificial Sequence
<220> FEATURE:
<223> OTHER INFORMATION: Protease sensor molecule

<400> SEQUENCE: 71

Leu Phe Met Ser Phe Ala Ile Pro
1               5

<210> SEQ ID NO 72
<211> LENGTH: 18
<212> TYPE: PRT
<213> ORGANISM: Artificial Sequence
<220> FEATURE:
<223> OTHER INFORMATION: Protease sensor molecule

<400> SEQUENCE: 72

Leu Gln Gly Ser Phe Met Lys Lys Asn Gln Asn Thr Glu Ile Gly Ser
1               5                   10                  15

Phe Glu

<210> SEQ ID NO 73
<211> LENGTH: 16
<212> TYPE: PRT
<213> ORGANISM: Artificial Sequence
<220> FEATURE:
<223> OTHER INFORMATION: Protease sensor molecule

<400> SEQUENCE: 73

Leu Gln Gly Ser Phe Met Asn Gln Asn Thr Glu Ile Gly Ser Phe Glu
1               5                   10                  15

<210> SEQ ID NO 74
<211> LENGTH: 15

```
<212> TYPE: PRT
<213> ORGANISM: Artificial Sequence
<220> FEATURE:
<223> OTHER INFORMATION: Protease sensor molecule

<400> SEQUENCE: 74

Leu Gln Gly Ser Leu Ser Phe Met Ala Ile Pro Gly Ser Phe Glu
1               5                   10                  15

<210> SEQ ID NO 75
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 75

Lys Gln Gln Gln
1

<210> SEQ ID NO 76
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 76

Ser Phe Gln Gln
1

<210> SEQ ID NO 77
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 77

Phe Met Gln Gln
1

<210> SEQ ID NO 78
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 78

Lys Lys Gln Gln
1

<210> SEQ ID NO 79
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 79

Lys Asn Gln Gln
1

<210> SEQ ID NO 80
<211> LENGTH: 4
<212> TYPE: PRT
```

<213> ORGANISM: Artificial Sequence
<220> FEATURE:
<223> OTHER INFORMATION: Protease sensor molecule

<400> SEQUENCE: 80

Asn Gln Gln Gln
1

<210> SEQ ID NO 81
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 81

Asn Thr Gln Gln
1

<210> SEQ ID NO 82
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 82

Glu Ile Gln Gln
1

<210> SEQ ID NO 83
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 83

Gln Gln Gln Gln
1

<210> SEQ ID NO 84
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 84

Gln Gln Lys Gln
1

<210> SEQ ID NO 85
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 85

Gln Gln Ser Phe
1

<210> SEQ ID NO 86
<211> LENGTH: 4
<212> TYPE: PRT
<213> ORGANISM: Artificial Sequence

```
<220> FEATURE:
<223> OTHER INFORMATION: Protease sensor molecule

<400> SEQUENCE: 86

Gln Gln Phe Met
1

<210> SEQ ID NO 87
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 87

Gln Gln Lys Lys
1

<210> SEQ ID NO 88
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 88

Gln Gln Lys Asn
1

<210> SEQ ID NO 89
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 89

Gln Gln Asn Gln
1

<210> SEQ ID NO 90
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 90

Gln Gln Asn Thr
1

<210> SEQ ID NO 91
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 91

Gln Gln Glu Ile
1

<210> SEQ ID NO 92
<211> LENGTH: 3
<212> TYPE: PRT
<213> ORGANISM: Artificial Sequence
<220> FEATURE:
```

```
<223> OTHER INFORMATION: Protease sensor molecule

<400> SEQUENCE: 92

Lys Gln Gln
1

<210> SEQ ID NO 93
<211> LENGTH: 12
<212> TYPE: PRT
<213> ORGANISM: Artificial Sequence
<220> FEATURE:
<223> OTHER INFORMATION: Protease sensor molecule

<400> SEQUENCE: 93

Gly Ser Pro Pro Leu Gln Gln Pro Pro Pro Gly Ser
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Protease sensor molecule

<400> SEQUENCE: 94

Gly Gly Ser Gly Gly Ser Leu Lys Gln Gln Gly Gly Ser Gly Gly Ser
1               5                   10                  15

<210> SEQ ID NO 95
<211> LENGTH: 3
<212> TYPE: PRT
<213> ORGANISM: Artificial Sequence
<220> FEATURE:
<223> OTHER INFORMATION: Protease sensor molecule

<400> SEQUENCE: 95

Leu Gln Gly
1

<210> SEQ ID NO 96
<211> LENGTH: 4
<212> TYPE: PRT
<213> ORGANISM: Artificial Sequence
<220> FEATURE:
<223> OTHER INFORMATION: Protease sensor molecule

<400> SEQUENCE: 96

Gly Ser Phe Glu
1

<210> SEQ ID NO 97
<211> LENGTH: 6
<212> TYPE: PRT
<213> ORGANISM: Artificial Sequence
<220> FEATURE:
<223> OTHER INFORMATION: Protease sensor molecule

<400> SEQUENCE: 97

Gly Ser Ser Gly Gly Ser
1               5

<210> SEQ ID NO 98
<211> LENGTH: 5
<212> TYPE: PRT
<213> ORGANISM: Artificial Sequence
<220> FEATURE:
<223> OTHER INFORMATION: Protease sensor molecule
```

<400> SEQUENCE: 98

Gly Ser Pro Pro Leu
1               5

<210> SEQ ID NO 99
<211> LENGTH: 5
<212> TYPE: PRT
<213> ORGANISM: Artificial Sequence
<220> FEATURE:
<223> OTHER INFORMATION: Protease sensor molecule

<400> SEQUENCE: 99

Pro Pro Pro Gly Ser
1               5

<210> SEQ ID NO 100
<211> LENGTH: 6
<212> TYPE: PRT
<213> ORGANISM: Artificial Sequence
<220> FEATURE:
<223> OTHER INFORMATION: Protease Sensor Molecule

<400> SEQUENCE: 100

Gly Gly Ser Gly Gly Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Protease Sensor Molecule

<400> SEQUENCE: 101

Gly Gly Ser Gly Gly Ser Leu
1               5

<210> SEQ ID NO 102
<211> LENGTH: 1713
<212> TYPE: DNA
<213> ORGANISM: Artificial Sequence
<220> FEATURE:
<223> OTHER INFORMATION: Protease Sensor Molecule

<400> SEQUENCE: 102
gaattcatgg tgagcaaggg cgaggagctg ttcaccgggg tggtgcccat cctggtcgag    60
ctggacggcg acgtaaacgg ccacaagttc agcgtgtccg gcgagggcga gggcgatgcc   120
acctacggca agctgaccct gaagttcatc tgcaccaccg gcaagctgcc cgtgccctgg   180
cccaccctcg tgaccaccct gagctacggc gtgcagtgct tcagccgcta ccccgaccac   240
atgaagcagc acgacttctt caagtccgcc atgcccgaag gctacgtcca ggagcgcacc   300
atcttcttca aggacgacgg caactacaag acccgcgccg aggtgaagtt cgagggcgac   360
accctggtga accgcatcga gctgaagggc atcgacttca aggaggacgg caacatcctg   420
gggcacaagc tggagtacaa ctacaacagc cacaacgtct atatcatggc cgacaagcag   480
aagaacggca tcaaggtgaa cttcaagatc cgccacaaca tcgaggacgg cagcgtgcag   540
ctcgccgacc actaccagca gaacaccccc atcggcgacg gccccgtgct gctgcccgac   600
aaccactacc tgagcaccca gtccgccctg agcaaagacc ccaacgagaa gcgcgatcac   660
atggtcctgc tggagttcgt gaccgccgcc gggatcactc tcggcatgga cgagctgtac   720

-continued

```
aagctgcagg gttcctttat gaaccagaac actgaaatcg gaagcttcga aatggcttcc      780
aaggtgtacg accccgagca acgcaaacgc atgatcactg gcctcagtg gtgggctcgc       840
tgcaagcaaa tgaacgtgct ggactccttc atcaactact atgattccga gaagcacgcc      900
gagaacgccg tgattttcct gcatggtaac gctgcctcca gctacctgtg gaggcacgtc      960
gtgcctcaca tcgagcccgt ggctagatgc atcatccctg atctgatcgg aatgggtaag     1020
tccggcaaga gcgggaatgg ctcatatcgc ctcctggatc actacaagta cctcaccgct     1080
tggttcgagc tgctgaacct ccaaagaaa atcatctttg tgggccacga ctgggggct       1140
gctctggcct ttcactactc ctacgagcac aagacaaga tcaaggccat cgtccatgct      1200
gagagtgtcg tggacgtgat cgagtcctgg gacgagtggc ctgacatcga ggaggatatc     1260
gccctgatca agagcgaaga gggcgagaaa atggtgcttg agaataactt cttcgtcgag     1320
accgtgctcc caagcaagat catgcggaaa ctggagcctg aggagttcgc tgcctacctg     1380
gagccattca aggagaaggg cgaggttaga cggcctaccc tctcctggcc tcgcgagatc     1440
cctctcgtta agggaggcaa gcccgacgtc gtccagattg tccgcaacta caacgcctac     1500
cttcgggcca gcgacgatct gcctaagatg ttcatcgagt ccgaccctgg gttcttttcc     1560
aacgctattg tcgagggagc taagaagttc cctaacaccg agttcgtgaa ggtgaagggc     1620
ctccacttca gccaggagga cgctccagat gaaatgggta agtacatcaa gagcttcgtg     1680
gagcgcgtgc tgaagaacga gcagtaactc gag                                  1713
```

<210> SEQ ID NO 103
<211> LENGTH: 1713
<212> TYPE: DNA
<213> ORGANISM: Artificial Sequence
<220> FEATURE:
<223> OTHER INFORMATION: Protease Sensor Molecule

<400> SEQUENCE: 103

```
gaattcatgg tgagcaaggg cgaggagctg ttcaccgggg tggtgcccat cctggtcgag       60
ctggacggcg acgtaaacgg ccacaagttc agcgtgtccg gcgagggcga gggcgatgcc      120
acctacggca agctgaccct gaagttcatc tgcaccaccg gcaagctgcc cgtgccctgg      180
cccaccctcg tgaccaccct gagctacggc gtgcagtgct tcagccgcta ccccgaccac      240
atgaagcagc acgacttctt caagtccgcc atgcccgaag gctacgtcca ggagcgcacc      300
atcttcttca aggacgacgg caactacaag acccgcgccg aggtgaagtt cgagggcgac      360
accctggtga accgcatcga gctgaagggc atcgacttca aggaggacgg caacatcctg      420
gggcacaagc tggagtacaa ctacaacagc cacaacgtct atatcatggc cgacaagcag      480
aagaacggca tcaaggtgaa cttcaagatc cgccacaaca tcgaggacgg cagcgtgcag      540
ctcgccgacc actaccagca gaacaccccc atcggcgacg gccccgtgct gctgcccgac      600
aaccactacc tgagcaccca gtccgccctg agcaaagacc ccaacgagaa gcgcgatcac      660
atggtcctgc tggagttcgt gaccgccgcc gggatcactc tcggcatgga cgagctgtac      720
aagctgcagg gttcctttat gaaccagaac actgaaatcg gaagcttcga aatggcttcc      780
aaggtgtacg accccgagca acgcaaacgc atgatcactg gcctcagtg gtgggctcgc       840
tgcaagcaaa tgaacgtgct ggactccttc atcaactact atgattccga gaagcacgcc      900
gagaacgccg tgattttcct gcatggtaac gctgcctcca gctacctgtg gaggcacgtc      960
gtgcctcaca tcgagcccgt ggctagatgc atcatccctg atctgatcgg aatgggtaag     1020
tccggcaaga gcgggaatgg ctcatatcgc ctcctggatc actacaagta cctcaccgct     1080
```

```
tggttcgagc tgctgaacct tccaaagaaa atcatctttg tgggccacga ctggggggct    1140
gctctggcct ttcactactc ctacgagcac aagacaaga tcaaggccat cgtccatgct     1200
gagagtgtcg tggacgtgat cgagtcctgg acgagtggc ctgacatcga ggaggatatc     1260
gccctgatca agagcgaaga gggcgagaaa atggtgcttg agaataactt cttcgtcgag    1320
accgtgctcc caagcaagat catgcggaaa ctggagcctg aggagttcgc tgcctacctg    1380
gagccattca ggagaaggg cgaggttaga cggcctaccc tctcctggcc tcgcgagatc     1440
cctctcgtta agggaggcaa gcccgacgtc gtccagattg tccgcaacta caacgcctac    1500
cttcgggcca gcgacgatct gcctaagatg ttcatcgagt ccgaccctgg gttctttcc    1560 aacgctattg tcgagggagc taagaagttc cctaacaccg agttcgtgaa ggtgaagggc    1620
ctccacttca gccaggagga cgctccagat gaaatgggta agtacatcaa gagcttcgtg    1680
gagcgcgtgc tgaagaacga gcagtaactc gag                                 1713
```

<210> SEQ ID NO 104
<211> LENGTH: 1710
<212> TYPE: DNA
<213> ORGANISM: Artificial Sequence
<220> FEATURE:
<223> OTHER INFORMATION: Protease Sensor Molecule

<400> SEQUENCE: 104

```
gaattcatgg tgagcaaggg cgaggagctg ttcaccgggg tggtgcccat cctggtcgag     60
ctggacggcg acgtaaacgg ccacaagttc agcgtgtccg gcgagggcga gggcgatgcc    120
acctacggca agctgaccct gaagttcatc tgcaccaccg gcaagctgcc cgtgccctgg    180
cccaccctcg tgaccaccct gagctacggc gtgcagtgct tcagccgcta ccccgaccac    240
atgaagcagc acgacttctt caagtccgcc atgcccgaag gctacgtcca ggagcgcacc    300
atcttcttca aggacgacgg caactacaag acccgcgccg aggtgaagtt cgagggcgac    360
accctggtga accgcatcga gctgaagggc atcgacttca aggaggacgg caacatcctg    420
gggcacaagc tggagtacaa ctacaacagc cacaacgtct atatcatggc cgacaagcag    480
aagaacggca tcaaggtgaa cttcaagatc cgccacaaca tcgaggacgg cagcgtgcag    540
ctcgccgacc actaccagca gaacacccc atcggcgacg gccccgtgct gctgcccgac    600
aaccactacc tgagcaccca gtccgccctg agcaaagacc ccaacgagaa gcgcgatcac    660
atggtcctgc tggagttcgt gaccgccgcc gggatcactc tcggcatgga cgagctgtac    720
aagctgcagg gctcttttaag ctttatggcc atccctggtt ccttcgaaat ggcttccaag    780
gtgtacgacc ccgagcaacg caaacgcatg atcactgggc tcagtggtg gctcgctgc     840 aagcaaatga acgtgctgga ctccttcatc aactactatg attccgagaa gcacgccgag    900
aacgccgtga tttttctgca tggtaacgct gcctccagct acctgtggag gcacgtcgtg    960
cctcacatcg agcccgtggc tagatgcatc atccctgatc tgatcggaat gggtaagtcc    1020
ggcaagagcg ggaatggctc atatcgcctc ctggatcact acaagtacct caccgcttgg    1080
ttcgagctgc tgaaccttcc aaagaaaatc atctttgtgg gccacgactg gggggctgct    1140
ctggcctttc actactccta cgagcaccaa gacaagatca aggccatcgt ccatgctgag    1200
agtgtcgtgg acgtgatcga gtcctgggac gagtggcctg acatcgagga ggatatcgcc    1260
ctgatcaaga gcgaagaggg cgagaaaatg gtgcttgaga taacttcctt cgtcgagacc    1320
gtgctcccaa gcaagatcat gcggaaactg gagcctgagg agttcgctgc ctacctggag    1380
```

-continued

```
ccattcaagg agaagggcga ggttagacgg cctaccctct cctggcctcg cgagatccct    1440
ctcgttaagg gaggcaagcc cgacgtcgtc cagattgtcc gcaactacaa cgcctacctt    1500
cgggccagcg acgatctgcc taagatgttc atcgagtccg accctgggtt cttttccaac    1560
gctattgtcg agggagctaa gaagttccct aacaccgagt tcgtgaaggt gaagggcctc    1620
cacttcagcc aggaggacgc tccagatgaa atgggtaagt acatcaagag cttcgtggag    1680
cgcgtgctga agaacgagca gtaactcgag                                     1710
```

<210> SEQ ID NO 105
<211> LENGTH: 568
<212> TYPE: PRT
<213> ORGANISM: Artificial Sequence
<220> FEATURE:
<223> OTHER INFORMATION: Protease Sensor Molecule

<400> SEQUENCE: 105

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Gly Ser Phe Met Lys Lys Asn Gln Asn Thr Glu Ile Gly Ser Phe
                245                 250                 255

Glu Met Ala Ser Lys Val Tyr Asp Pro Glu Gln Arg Lys Arg Met Ile
            260                 265                 270

Thr Gly Pro Gln Trp Trp Ala Arg Cys Lys Gln Met Asn Val Leu Asp
        275                 280                 285

Ser Phe Ile Asn Tyr Tyr Asp Ser Glu Lys His Ala Glu Asn Ala Val
    290                 295                 300
```

Ile Phe Leu His Gly Asn Ala Ala Ser Ser Tyr Leu Trp Arg His Val
305                 310                 315                 320

Val Pro His Ile Glu Pro Val Ala Arg Cys Ile Ile Pro Asp Leu Ile
                325                 330                 335

Gly Met Gly Lys Ser Gly Lys Ser Gly Asn Gly Ser Tyr Arg Leu Leu
            340                 345                 350

Asp His Tyr Lys Tyr Leu Thr Ala Trp Phe Glu Leu Leu Asn Leu Pro
        355                 360                 365

Lys Lys Ile Ile Phe Val Gly His Asp Trp Gly Ala Ala Leu Ala Phe
    370                 375                 380

His Tyr Ser Tyr Glu His Gln Asp Lys Ile Lys Ala Ile Val His Ala
385                 390                 395                 400

Glu Ser Val Val Asp Val Ile Glu Ser Trp Asp Glu Trp Pro Asp Ile
                405                 410                 415

Glu Glu Asp Ile Ala Leu Ile Lys Ser Glu Gly Glu Lys Met Val
            420                 425                 430

Leu Glu Asn Asn Phe Phe Val Glu Thr Val Leu Pro Ser Lys Ile Met
        435                 440                 445

Arg Lys Leu Glu Pro Glu Glu Phe Ala Ala Tyr Leu Glu Pro Phe Lys
450                 455                 460

Glu Lys Gly Glu Val Arg Arg Pro Thr Leu Ser Trp Pro Arg Glu Ile
465                 470                 475                 480

Pro Leu Val Lys Gly Gly Lys Pro Asp Val Val Gln Ile Val Arg Asn
                485                 490                 495

Tyr Asn Ala Tyr Leu Arg Ala Ser Asp Asp Leu Pro Lys Met Phe Ile
            500                 505                 510

Glu Ser Asp Pro Gly Phe Phe Ser Asn Ala Ile Val Glu Gly Ala Lys
        515                 520                 525

Lys Phe Pro Asn Thr Glu Phe Val Lys Val Lys Gly Leu His Phe Ser
    530                 535                 540

Gln Glu Asp Ala Pro Asp Glu Met Gly Lys Tyr Ile Lys Ser Phe Val
545                 550                 555                 560

Glu Arg Val Leu Lys Asn Glu Gln
                565

<210> SEQ ID NO 106
<211> LENGTH: 566
<212> TYPE: PRT
<213> ORGANISM: Artificial Sequence
<220> FEATURE:
<223> OTHER INFORMATION: Protease Sensor Molecule

<400> SEQUENCE: 106

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

Gln Gly Ser Phe Met Asn Gln Asn Thr Glu Ile Gly Ser Phe Glu Met
                245                 250                 255

Ala Ser Lys Val Tyr Asp Pro Glu Gln Arg Lys Arg Met Ile Thr Gly
            260                 265                 270

Pro Gln Trp Trp Ala Arg Cys Lys Gln Met Asn Val Leu Asp Ser Phe
            275                 280                 285

Ile Asn Tyr Tyr Asp Ser Glu Lys His Ala Glu Asn Ala Val Ile Phe
    290                 295                 300

Leu His Gly Asn Ala Ala Ser Ser Tyr Leu Trp Arg His Val Val Pro
305                 310                 315                 320

His Ile Glu Pro Val Ala Arg Cys Ile Ile Pro Asp Leu Ile Gly Met
            325                 330                 335

Gly Lys Ser Gly Lys Ser Gly Asn Gly Ser Tyr Arg Leu Leu Asp His
            340                 345                 350

Tyr Lys Tyr Leu Thr Ala Trp Phe Glu Leu Leu Asn Leu Pro Lys Lys
        355                 360                 365

Ile Ile Phe Val Gly His Asp Trp Gly Ala Ala Leu Ala Phe His Tyr
    370                 375                 380

Ser Tyr Glu His Gln Asp Lys Ile Lys Ala Ile Val His Ala Glu Ser
385                 390                 395                 400

Val Val Asp Val Ile Glu Ser Trp Asp Glu Trp Pro Asp Ile Glu Glu
                405                 410                 415

Asp Ile Ala Leu Ile Lys Ser Glu Glu Gly Glu Lys Met Val Leu Glu
            420                 425                 430

Asn Asn Phe Phe Val Glu Thr Val Leu Pro Ser Lys Ile Met Arg Lys
            435                 440                 445

Leu Glu Pro Glu Glu Phe Ala Ala Tyr Leu Glu Pro Phe Lys Glu Lys
        450                 455                 460

Gly Glu Val Arg Arg Pro Thr Leu Ser Trp Pro Arg Glu Ile Pro Leu
465                 470                 475                 480

Val Lys Gly Gly Lys Pro Asp Val Val Gln Ile Val Arg Asn Tyr Asn
                485                 490                 495

Ala Tyr Leu Arg Ala Ser Asp Asp Leu Pro Lys Met Phe Ile Glu Ser
            500                 505                 510

Asp Pro Gly Phe Phe Ser Asn Ala Ile Val Glu Gly Ala Lys Lys Phe
```

```
                515                 520                 525
Pro Asn Thr Glu Phe Val Lys Val Lys Gly Leu His Phe Ser Gln Glu
530                 535                 540
Asp Ala Pro Asp Glu Met Gly Lys Tyr Ile Lys Ser Phe Val Glu Arg
545                 550                 555                 560
Val Leu Lys Asn Glu Gln
                565
```

<210> SEQ ID NO 107
<211> LENGTH: 565
<212> TYPE: PRT
<213> ORGANISM: Artificial Sequence
<220> FEATURE:
<223> OTHER INFORMATION: Protease Sensor Molecule

<400> SEQUENCE: 107

```
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
        50                  55                  60
Leu Ser Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
210                 215                 220
Val Thr Ala Ala Gly Ile Thr Leu Gly Met Asp Glu Leu Tyr Lys Leu
225                 230                 235                 240
Gln Gly Ser Leu Ser Phe Met Ala Ile Pro Gly Ser Phe Glu Met Ala
                245                 250                 255
Ser Lys Val Tyr Asp Pro Glu Gln Arg Lys Arg Met Ile Thr Gly Pro
            260                 265                 270
Gln Trp Trp Ala Arg Cys Lys Gln Met Asn Val Leu Asp Ser Phe Ile
        275                 280                 285
Asn Tyr Tyr Asp Ser Glu Lys His Ala Glu Asn Ala Val Ile Phe Leu
290                 295                 300
His Gly Asn Ala Ala Ser Ser Tyr Leu Trp Arg His Val Val Pro His
```

```
            305                 310                 315                 320
Ile Glu Pro Val Ala Arg Cys Ile Ile Pro Asp Leu Ile Gly Met Gly
                    325                 330                 335
Lys Ser Gly Lys Ser Gly Asn Gly Ser Tyr Arg Leu Leu Asp His Tyr
                340                 345                 350
Lys Tyr Leu Thr Ala Trp Phe Glu Leu Leu Asn Leu Pro Lys Lys Ile
            355                 360                 365
Ile Phe Val Gly His Asp Trp Gly Ala Ala Leu Ala Phe His Tyr Ser
        370                 375                 380
Tyr Glu His Gln Asp Lys Ile Lys Ala Ile Val His Ala Glu Ser Val
385                 390                 395                 400
Val Asp Val Ile Glu Ser Trp Asp Glu Trp Pro Asp Ile Glu Glu Asp
                405                 410                 415
Ile Ala Leu Ile Lys Ser Glu Glu Gly Glu Lys Met Val Leu Glu Asn
            420                 425                 430
Asn Phe Phe Val Glu Thr Val Leu Pro Ser Lys Ile Met Arg Lys Leu
        435                 440                 445
Glu Pro Glu Glu Phe Ala Ala Tyr Leu Glu Pro Phe Lys Glu Lys Gly
    450                 455                 460
Glu Val Arg Arg Pro Thr Leu Ser Trp Pro Arg Glu Ile Pro Leu Val
465                 470                 475                 480
Lys Gly Gly Lys Pro Asp Val Val Gln Ile Val Arg Asn Tyr Asn Ala
                485                 490                 495
Tyr Leu Arg Ala Ser Asp Asp Leu Pro Lys Met Phe Ile Glu Ser Asp
            500                 505                 510
Pro Gly Phe Phe Ser Asn Ala Ile Val Glu Gly Ala Lys Lys Phe Pro
        515                 520                 525
Asn Thr Glu Phe Val Lys Val Lys Gly Leu His Phe Ser Gln Glu Asp
    530                 535                 540
Ala Pro Asp Glu Met Gly Lys Tyr Ile Lys Ser Phe Val Glu Arg Val
545                 550                 555                 560
Leu Lys Asn Glu Gln
            565

<210> SEQ ID NO 108
<211> LENGTH: 1710
<212> TYPE: DNA
<213> ORGANISM: Artificial Sequence
<220> FEATURE:
<223> OTHER INFORMATION: Protease Sensor Molecule

<400> SEQUENCE: 108
gaattcatgg tgagcaaggg cgaggagctg ttcaccgggg tggtgcccat cctggtcgag      60
ctggacggcg acgtaaacgg ccacaagttc agcgtgtccg gcgagggcga gggcgatgcc     120
acctacggca agctgaccct gaagttcatc tgcaccaccg gcaagctgcc cgtgccctgg     180
cccaccctcg tgaccaccct gagctacggc gtgcagtgct tcagccgcta ccccgaccac     240
atgaagcagc acgacttctt caagtccgcc atgcccgaag gctacgtcca ggagcgcacc     300
atcttcttca aggacgacgg caactacaag acccgcgccg aggtgaagtt cgagggcgac     360
accctggtga accgcatcga gctgaagggc atcgacttca aggaggacgg caacatcctg     420
gggcacaagc tggagtacaa ctacaacagc cacaacgtct atatcatggc cgacaagcag     480
aagaacggca tcaaggtgaa cttcaagatc cgccacaaca tcgaggacgg cagcgtgcag     540
ctcgccgacc actaccagca gaacaccccc atcggcgacg gccccgtgct gctgcccgac     600
```

```
aaccactacc tgagcaccca gtccgccctg agcaaagacc ccaacgagaa gcgcgatcac   660
atggtcctgc tggagttcgt gaccgccgcc gggatcactc tcggcatgga cgagctgtac   720
aagctgcagg gttccaaaaa gtataaagtt aaggaaggat cacttcagat ggcttccaag   780
gtgtacgacc ccgagcaacg caaacgcatg atcactgggc tcagtggtg ggctcgctgc    840 aagcaaatga acgtgctgga ctccttcatc aactactatg attccgagaa gcacgccgag   900
aacgccgtga ttttctgca tggtaacgct gcctccagct acctgtggag gcacgtcgtg    960
cctcacatcg agcccgtggc tagatgcatc atccctgatc tgatcggaat gggtaagtcc   1020
ggcaagagcg ggaatggctc atatcgcctc ctggatcact acaagtacct caccgcttgg   1080
ttcgagctgc tgaaccttcc aaagaaaatc atctttgtgg ccacgactg ggggctgct    1140 ctggcctttc actactccta cgagcaccaa gacaagatca aggccatcgt ccatgctgag   1200
agtgtcgtgg acgtgatcga gtcctgggac gagtggcctg acatcgagga ggatatcgcc   1260
ctgatcaaga gcaagagggg cgagaaaatg gtgcttgaga taacttctt cgtcgagacc    1320 gtgctcccaa gcaagatcat gcggaaactg gagcctgagg agttcgctgc ctacctggag   1380
ccattcaagg agaagggcga ggttagacgg cctaccctct cctggcctcg cgagatccct   1440
ctcgttaagg gaggcaagcc cgacgtcgtc cagattgtcc gcaactacaa cgcctacctt   1500
cgggccagcg acgatctgcc taagatgttc atcgagtccg accctgggtt cttttccaac   1560
gctattgtcg agggagctaa gaagttccct aacaccgagt tcgtgaaggt gaagggcctc   1620
cacttcagcc aggaggacgc tccagatgaa atgggtaagt acatcaagag cttcgtggag   1680
cgcgtgctga agaacgagca gtaactcgag                                    1710
```

<210> SEQ ID NO 109
<211> LENGTH: 565
<212> TYPE: PRT
<213> ORGANISM: Artificial Sequence
<220> FEATURE:
<223> OTHER INFORMATION: Protease Sensor Molecule

<400> SEQUENCE: 109

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Gly Ser Lys Lys Tyr Lys Val Lys Glu Gly Ser Leu Gln Met Ala
                245                 250                 255

Ser Lys Val Tyr Asp Pro Glu Gln Arg Lys Arg Met Ile Thr Gly Pro
            260                 265                 270

Gln Trp Trp Ala Arg Cys Lys Gln Met Asn Val Leu Asp Ser Phe Ile
        275                 280                 285

Asn Tyr Tyr Asp Ser Glu Lys His Ala Glu Asn Ala Val Ile Phe Leu
        290                 295                 300

His Gly Asn Ala Ala Ser Ser Tyr Leu Trp Arg His Val Val Pro His
305                 310                 315                 320

Ile Glu Pro Val Ala Arg Cys Ile Ile Pro Asp Leu Ile Gly Met Gly
                325                 330                 335

Lys Ser Gly Lys Ser Gly Asn Gly Ser Tyr Arg Leu Leu Asp His Tyr
            340                 345                 350

Lys Tyr Leu Thr Ala Trp Phe Glu Leu Leu Asn Leu Pro Lys Lys Ile
        355                 360                 365

Ile Phe Val Gly His Asp Trp Gly Ala Ala Leu Ala Phe His Tyr Ser
    370                 375                 380

Tyr Glu His Gln Asp Lys Ile Lys Ala Ile Val His Ala Glu Ser Val
385                 390                 395                 400

Val Asp Val Ile Glu Ser Trp Asp Glu Trp Pro Asp Ile Glu Glu Asp
                405                 410                 415

Ile Ala Leu Ile Lys Ser Glu Glu Gly Glu Lys Met Val Leu Glu Asn
            420                 425                 430

Asn Phe Phe Val Glu Thr Val Leu Pro Ser Lys Ile Met Arg Lys Leu
        435                 440                 445

Glu Pro Glu Glu Phe Ala Ala Tyr Leu Glu Pro Phe Lys Glu Lys Gly
    450                 455                 460

Glu Val Arg Arg Pro Thr Leu Ser Trp Pro Arg Glu Ile Pro Leu Val
465                 470                 475                 480

Lys Gly Gly Lys Pro Asp Val Val Gln Ile Val Arg Asn Tyr Asn Ala
                485                 490                 495

Tyr Leu Arg Ala Ser Asp Asp Leu Pro Lys Met Phe Ile Glu Ser Asp
            500                 505                 510

Pro Gly Phe Phe Ser Asn Ala Ile Val Glu Gly Ala Lys Lys Phe Pro
        515                 520                 525

Asn Thr Glu Phe Val Lys Val Lys Gly Leu His Phe Ser Gln Glu Asp
    530                 535                 540

Ala Pro Asp Glu Met Gly Lys Tyr Ile Lys Ser Phe Val Glu Arg Val
545                 550                 555                 560

Leu Lys Asn Glu Gln
                565
```

```
<210> SEQ ID NO 110
<211> LENGTH: 11
<212> TYPE: PRT
<213> ORGANISM: Artificial Sequence
<220> FEATURE:
<223> OTHER INFORMATION: Protease sensor molecule
<220> FEATURE:
<221> NAME/KEY: X
<222> LOCATION: (3)..(6)
<223> OTHER INFORMATION: X can be any amino acid
<220> FEATURE:
<221> NAME/KEY: Z
<222> LOCATION: (8)..(8)
<223> OTHER INFORMATION: Z is is lysine, tyrosine, valine or glutamic
      acid

<400> SEQUENCE: 110

Leu Gln Xaa Xaa Xaa Xaa Lys Glx Lys Leu Gln
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Protease sensor molecule

<400> SEQUENCE: 111

Leu Gln Gly Ser Lys Lys Tyr Lys Val Lys Glu Gly Ser Leu Gln
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Protease sensor molecule

<400> SEQUENCE: 112

Leu Gln Gly Ser Lys Gln Lys Gln Lys Gln Lys Gln Gly Ser Phe Glu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Protease sensor molecule

<400> SEQUENCE: 113

Leu Gln Gly Ser Pro Pro Leu Lys Gln Pro Pro Pro Gly Ser Phe Glu
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Protease sensor molecule

<400> SEQUENCE: 114

Leu Gln Gly Ser Pro Pro Leu Gln Gln Pro Gln Pro Gly Ser Phe Glu
1               5                   10                  15

<210> SEQ ID NO 115
<211> LENGTH: 20
<212> TYPE: PRT
<213> ORGANISM: Artificial Sequence
<220> FEATURE:
```

<223> OTHER INFORMATION: Protease sensor molecule

<400> SEQUENCE: 115

Leu Gln Gly Gly Ser Gly Gly Ser Leu Lys Gln Gln Gly Gly Ser Gly
1               5                   10                  15

Gly Ser Phe Glu
            20

<210> SEQ ID NO 116
<211> LENGTH: 1701
<212> TYPE: DNA
<213> ORGANISM: Artificial Sequence
<220> FEATURE:
<223> OTHER INFORMATION: Nucleotide sequence encoding GFP2-Pflu-H1-RLuc2

<400> SEQUENCE: 116

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagctg     720
cagggaagtc caccgttgaa caacccccct cctggctcct cgaaatggc ttccaaggtg      780
tacgaccccg agcaacgcaa acgcatgatc actgggcctc agtggtgggc tcgctgcaag     840
caaatgaacg tgctggactc cttcatcaac tactatgatt ccgagaagca cgccgagaac     900
gccgtgattt ttctgcatgg taacgctgcc tccagctacc tgtgaggca cgtcgtgcct      960
cacatcgagc ccgtggctag atgcatcatc cctgatctga tcggaatggg taagtccggc    1020
aagagcggga atggctcata tcgcctcctg atcactaca agtacctcac cgcttggttc    1080
gagctgctga accttccaaa gaaaatcatc tttgtgggcc acgactgggg gctgctctg    1140
gcctttcact actcctacga gcaccaagac aagatcaagg ccatcgtcca tgctgagagt    1200
gtcgtggacg tgatcgagtc ctgggacgag tggcctgaca tcgaggagga tatcgccctg    1260
atcaagagcg aagagggcga gaaaatggtg cttgagaata acttcttcgt cgagaccgtg    1320
ctcccaagca gatcatgcg gaaactggag cctgaggagt cgctgcccta cctggagcca   1380
ttcaaggaga agggcgaggt tagacggcct accctctcct ggcctcgcga gatccctctc    1440
gttaagggag gcaagcccga cgtcgtccag attgtccgca actacaacgc ctaccttcgg    1500
gccagcgacg atctgcctaa gatgttcatc gagtccgacc ctgggttctt ttccaacgct    1560
attgtcgagg gagctaagaa gttccctaac accgagttcg tgaaggtgaa gggcctccac    1620
ttcagccagg aggacgctcc agatgaaatg ggtaagtaca tcaagagctt cgtggagcgc    1680
gtgctgaaga acgagcagta a                                              1701
```

<210> SEQ ID NO 117
<211> LENGTH: 1707
<212> TYPE: DNA
<213> ORGANISM: Artificial Sequence
<220> FEATURE:
<223> OTHER INFORMATION: Nucleotide sequence encoding GFP2-Pflu-H2-RLuc2

<400> SEQUENCE: 117

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgagcta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagctg   720
cagggatctc cacccttaca acaaccgcaa ccgggtagct tcgaaatggc ttccaaggtg   780
tacgaccccg agcaacgcaa acgcatgatc actgggcctc agtggtgggc tcgctgcaag   840
caaatgaacg tgctggactc cttcatcaac tactatgatt ccgagaagca cgccgagaac   900
gccgtgattt ttctgcatgg taacgctgcc tccagctacc tgtggaggca cgtcgtgcct   960
cacatcgagc ccgtggctag atgcatcatc cctgatctga tcggaatggg taagtccggc  1020
aagagcggga atggctcata tcgcctcctg gatcactaca agtacctcac cgcttggttc  1080
gagctgctga accttccaaa gaaaatcatc tttgtgggcc acgactgggg gctgctctg   1140
gcctttcact actcctacga gcaccaagac aagatcaagg ccatcgtcca tgctgagagt  1200
gtcgtggacg tgatcgagtc ctgggacgag tggcctgaca tcgaggagga tatcgccctg  1260
atcaagagcg aagagggcga gaaaatggtg cttgagaata acttcttcgt cgagaccgtg  1320
ctcccaagca gatcatgcg gaaactggag cctgaggagt cgctgcctcc ctggagcca   1380
ttcaaggaga agggcgaggt tagacggcct accctctcct ggcctcgcga gatccctctc  1440
gttaagggag gcaagcccga cgtcgtccag attgtccgca actacaacgc ctaccttcgg  1500
gccagcgacg atctgcctaa gatgttcatc gagtccgacc ctgggttctt ttccaacgct  1560
attgtcgagg gagctaagaa gttccctaac accgagttcg tgaaggtgaa gggcctccac  1620
ttcagccagg aggacgctcc agatgaaatg ggtaagtaca tcaagagctt cgtggagcgc  1680
gtgctgaaga acgagcagta actcgag                                      1707
```

<210> SEQ ID NO 118
<211> LENGTH: 1707
<212> TYPE: DNA
<213> ORGANISM: Artificial Sequence
<220> FEATURE:
<223> OTHER INFORMATION: Nucleotide sequence encoding GFP2-Pflu-H3-RLuc2

<400> SEQUENCE: 118

```
atggtgagca agggcgagga gctgttcacc ggggtggtgc ccatcctggt cgagctggac    60
```

```
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgagcta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagctg      720
caggggtcta acaaaaaaca gaagcaaaag caaggatcat cgaaatggc ttccaaggtg      780 tacgaccccg agcaacgcaa acgcatgatc actgggcctc agtggtgggc tcgctgcaag      840
caaatgaacg tgctggactc cttcatcaac tactatgatt ccgagaagca cgccgagaac      900
gccgtgattt ttctgcatgg taacgctgcc tccagctacc tgtggaggca cgtcgtgcct      960
cacatcgagc ccgtggctag atgcatcatc cctgatctga tcggaatggg taagtccggc     1020
aagagcggga atggctcata tcgcctcctg gatcactaca agtacctcac cgcttggttc     1080
gagctgctga accttccaaa gaaaatcatc tttgtgggcc acgactgggg gctgctctg      1140 gcctttcact actcctacga gcaccaagac aagatcaagg ccatcgtcca tgctgagagt     1200
gtcgtggacg tgatcgagtc ctgggacgag tggcctgaca tcgaggagga tatcgccctg     1260
atcaagagcg aagagggcga gaaaatggtg cttgagaata acttcttcgt cgagaccgtg     1320
ctcccaagca agatcatgcg gaaactggag cctgaggagt cgctgcccta cctggagcca     1380
ttcaaggaga gggcgaggt tagacggcct accctctcct ggcctcgcga gatccctctc     1440
gttaagggag gcaagcccga cgtcgtccag attgtccgca actacaacgc ctaccttcgg     1500
gccagcgacg atctgcctaa gatgttcatc gagtccgacc ctgggttctt ttccaacgct     1560
attgtcgagg gagctaagaa gttccctaac accgagttcg tgaaggtgaa gggcctccac     1620
ttcagccagg aggacgctcc agatgaaatg ggtaagtaca tcaagagctt cgtggagcgc     1680
gtgctgaaga acgagcagta actcgag                                         1707

<210> SEQ ID NO 119
<211> LENGTH: 1713
<212> TYPE: DNA
<213> ORGANISM: Artificial Sequence
<220> FEATURE:
<223> OTHER INFORMATION: Nucleotide sequence encoding GFP2-Pflu-H4-RLuc2

<400> SEQUENCE: 119
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgagcta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
```

```
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagctg    720
caggggggaa gcgtgtggtag tttgaaacag cagggcggat caggagggtc tttcgaaatg    780
gcttccaagg tgtacgaccc cgagcaacgc aaacgcatga tcactgggcc tcagtggtgg    840
gctcgctgca agcaaatgaa cgtgctggac tccttcatca actactatga ttccgagaag    900
cacgccgaga acgccgtgat ttttctgcat ggtaacgctg cctccagcta cctgtggagg    960
cacgtcgtgc ctcacatcga gcccgtggct agatgcatca tccctgatct gatcggaatg   1020
ggtaagtccg gcaagagcgg gaatggctca tatcgcctcc tggatcacta caagtacctc   1080
accgcttggt tcgagctgct gaaccttcca aagaaaatca tctttgtggg ccacgactgg   1140
ggggctgctc tggcctttca ctactcctac gagcaccaag acaagatcaa ggccatcgtc   1200
catgctgaga gtgtcgtgga cgtgatcgag tcctgggacg agtggcctga catcgaggag   1260
gatatcgccc tgatcaagag cgaagagggc gagaaaatgg tgcttgagaa taacttcttc   1320
gtcgagaccg tgctcccaag caagatcatg cggaaactgg agcctgagga gttcgctgcc   1380
tacctggagc cattcaagga gaagggcgag gttagacggc ctaccctctc ctggcctcgc   1440
gagatccctc tcgttaaggg aggcaagccc gacgtcgtcc agattgtccg caactacaac   1500
gcctaccttc gggccagcga cgatctgcct aagatgttca tcgagtccga ccctgggttc   1560
ttttccaacg ctattgtcga gggagctaag aagttcccta acaccgagtt cgtgaaggtg   1620
aagggcctcc acttcagcca ggaggacgct ccagatgaaa tgggtaagta catcaagagc   1680
ttcgtggagc gcgtgctgaa gaacgagcag taa                                1713
```

<210> SEQ ID NO 120
<211> LENGTH: 566
<212> TYPE: PRT
<213> ORGANISM: Artificial Sequence
<220> FEATURE:
<223> OTHER INFORMATION: GFP2-Pflu-H1-RLuc2 fusion protein

<400> SEQUENCE: 120

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

Gln Gly Ser Pro Pro Leu Lys Gln Pro Pro Gly Ser Phe Glu Met
                245                 250                 255

Ala Ser Lys Val Tyr Asp Pro Glu Gln Arg Lys Arg Met Ile Thr Gly
            260                 265                 270

Pro Gln Trp Trp Ala Arg Cys Lys Gln Met Asn Val Leu Asp Ser Phe
        275                 280                 285

Ile Asn Tyr Tyr Asp Ser Glu Lys His Ala Glu Asn Ala Val Ile Phe
    290                 295                 300

Leu His Gly Asn Ala Ala Ser Ser Tyr Leu Trp Arg His Val Val Pro
305                 310                 315                 320

His Ile Glu Pro Val Ala Arg Cys Ile Ile Pro Asp Leu Ile Gly Met
                325                 330                 335

Gly Lys Ser Gly Lys Ser Gly Asn Gly Ser Tyr Arg Leu Leu Asp His
            340                 345                 350

Tyr Lys Tyr Leu Thr Ala Trp Phe Glu Leu Leu Asn Leu Pro Lys Lys
        355                 360                 365

Ile Ile Phe Val Gly His Asp Trp Gly Ala Ala Leu Ala Phe His Tyr
    370                 375                 380

Ser Tyr Glu His Gln Asp Lys Ile Lys Ala Ile Val His Ala Glu Ser
385                 390                 395                 400

Val Val Asp Val Ile Glu Ser Trp Asp Glu Trp Pro Asp Ile Glu Glu
                405                 410                 415

Asp Ile Ala Leu Ile Lys Ser Glu Glu Gly Glu Lys Met Val Leu Glu
            420                 425                 430

Asn Asn Phe Phe Val Glu Thr Val Leu Pro Ser Lys Ile Met Arg Lys
        435                 440                 445

Leu Glu Pro Glu Glu Phe Ala Ala Tyr Leu Glu Pro Phe Lys Glu Lys
    450                 455                 460

Gly Glu Val Arg Arg Pro Thr Leu Ser Trp Pro Arg Glu Ile Pro Leu
465                 470                 475                 480

Val Lys Gly Gly Lys Pro Asp Val Val Gln Ile Val Arg Asn Tyr Asn
                485                 490                 495

Ala Tyr Leu Arg Ala Ser Asp Asp Leu Pro Lys Met Phe Ile Glu Ser
            500                 505                 510

Asp Pro Gly Phe Phe Ser Asn Ala Ile Val Glu Gly Ala Lys Lys Phe
        515                 520                 525

Pro Asn Thr Glu Phe Val Lys Val Lys Gly Leu His Phe Ser Gln Glu
530                 535                 540

Asp Ala Pro Asp Glu Met Gly Lys Tyr Ile Lys Ser Phe Val Glu Arg
```

Val Leu Lys Asn Glu Gln
                565

<210> SEQ ID NO 121
<211> LENGTH: 567
<212> TYPE: PRT
<213> ORGANISM: Artificial Sequence
<220> FEATURE:
<223> OTHER INFORMATION: GFP2-Pflu-H2-RLuc2 fusion protein

<400> SEQUENCE: 121

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Gly Ser Pro Pro Leu Gln Gln Pro Gln Pro Gly Ser Phe Glu Met
                245                 250                 255

Ala Ser Lys Val Tyr Asp Pro Glu Gln Arg Lys Arg Met Ile Thr Gly
            260                 265                 270

Pro Gln Trp Trp Ala Arg Cys Lys Gln Met Asn Val Leu Asp Ser Phe
        275                 280                 285

Ile Asn Tyr Tyr Asp Ser Glu Lys His Ala Glu Asn Ala Val Ile Phe
    290                 295                 300

Leu His Gly Asn Ala Ala Ser Ser Tyr Leu Trp Arg His Val Val Pro
305                 310                 315                 320

His Ile Glu Pro Val Ala Arg Cys Ile Ile Pro Asp Leu Ile Gly Met
                325                 330                 335

Gly Lys Ser Gly Lys Ser Gly Asn Gly Ser Tyr Arg Leu Leu Asp His

```
                   340                 345                 350
Tyr Lys Tyr Leu Thr Ala Trp Phe Glu Leu Leu Asn Leu Pro Lys Lys
            355                 360                 365

Ile Ile Phe Val Gly His Asp Trp Gly Ala Ala Leu Ala Phe His Tyr
        370                 375                 380

Ser Tyr Glu His Gln Asp Lys Ile Lys Ala Ile Val His Ala Glu Ser
385                 390                 395                 400

Val Val Asp Val Ile Glu Ser Trp Asp Glu Trp Pro Asp Ile Glu Glu
                405                 410                 415

Asp Ile Ala Leu Ile Lys Ser Glu Glu Gly Glu Lys Met Val Leu Glu
            420                 425                 430

Asn Asn Phe Phe Val Glu Thr Val Leu Pro Ser Lys Ile Met Arg Lys
        435                 440                 445

Leu Glu Pro Glu Glu Phe Ala Ala Tyr Leu Glu Pro Phe Lys Glu Lys
    450                 455                 460

Gly Glu Val Arg Arg Pro Thr Leu Ser Trp Pro Arg Glu Ile Pro Leu
465                 470                 475                 480

Val Lys Gly Gly Lys Pro Asp Val Val Gln Ile Val Arg Asn Tyr Asn
                485                 490                 495

Ala Tyr Leu Arg Ala Ser Asp Asp Leu Pro Lys Met Phe Ile Glu Ser
            500                 505                 510

Asp Pro Gly Phe Phe Ser Asn Ala Ile Val Glu Gly Ala Lys Lys Phe
        515                 520                 525

Pro Asn Thr Glu Phe Val Lys Val Lys Gly Leu His Phe Ser Gln Glu
    530                 535                 540

Asp Ala Pro Asp Glu Met Gly Lys Tyr Ile Lys Ser Phe Val Glu Arg
545                 550                 555                 560

Val Leu Lys Asn Glu Gln Glu
                565

<210> SEQ ID NO 122
<211> LENGTH: 566
<212> TYPE: PRT
<213> ORGANISM: Artificial Sequence
<220> FEATURE:
<223> OTHER INFORMATION: GFP2-Pflu-H3-RLuc2 fusion protein

<400> SEQUENCE: 122

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
```

```
                130                 135                 140
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Gly Ser Lys Gln Lys Gln Lys Gln Gly Ser Phe Glu Met
                245                 250                 255

Ala Ser Lys Val Tyr Asp Pro Glu Gln Arg Lys Arg Met Ile Thr Gly
            260                 265                 270

Pro Gln Trp Trp Ala Arg Cys Lys Gln Met Asn Val Leu Asp Ser Phe
        275                 280                 285

Ile Asn Tyr Tyr Asp Ser Glu Lys His Ala Glu Asn Ala Val Ile Phe
        290                 295                 300

Leu His Gly Asn Ala Ala Ser Ser Tyr Leu Trp Arg His Val Val Pro
305                 310                 315                 320

His Ile Glu Pro Val Ala Arg Cys Ile Ile Pro Asp Leu Ile Gly Met
                325                 330                 335

Gly Lys Ser Gly Lys Ser Gly Asn Gly Ser Tyr Arg Leu Leu Asp His
            340                 345                 350

Tyr Lys Tyr Leu Thr Ala Trp Phe Glu Leu Leu Asn Leu Pro Lys Lys
        355                 360                 365

Ile Ile Phe Val Gly His Asp Trp Gly Ala Ala Leu Ala Phe His Tyr
    370                 375                 380

Ser Tyr Glu His Gln Asp Lys Ile Lys Ala Ile Val His Ala Glu Ser
385                 390                 395                 400

Val Val Asp Val Ile Glu Ser Trp Asp Glu Trp Pro Asp Ile Glu Glu
                405                 410                 415

Asp Ile Ala Leu Ile Lys Ser Glu Glu Gly Glu Lys Met Val Leu Glu
            420                 425                 430

Asn Asn Phe Phe Val Glu Thr Val Leu Pro Ser Lys Ile Met Arg Lys
        435                 440                 445

Leu Glu Pro Glu Glu Phe Ala Ala Tyr Leu Glu Pro Phe Lys Glu Lys
    450                 455                 460

Gly Glu Val Arg Arg Pro Thr Leu Ser Trp Pro Arg Glu Ile Pro Leu
465                 470                 475                 480

Val Lys Gly Gly Lys Pro Asp Val Val Gln Ile Val Arg Asn Tyr Asn
                485                 490                 495

Ala Tyr Leu Arg Ala Ser Asp Asp Leu Pro Lys Met Phe Ile Glu Ser
            500                 505                 510

Asp Pro Gly Phe Phe Ser Asn Ala Ile Val Glu Gly Ala Lys Lys Phe
        515                 520                 525

Pro Asn Thr Glu Phe Val Lys Val Lys Gly Leu His Phe Ser Gln Glu
    530                 535                 540

Asp Ala Pro Asp Glu Met Gly Lys Tyr Ile Lys Ser Phe Val Glu Arg
545                 550                 555                 560
```

Val Leu Lys Asn Glu Gln
                565

<210> SEQ ID NO 123
<211> LENGTH: 570
<212> TYPE: PRT
<213> ORGANISM: Artificial Sequence
<220> FEATURE:
<223> OTHER INFORMATION: GFP2-Pflu-H4-RLuc2 fusion protein

<400> SEQUENCE: 123

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Gly Gly Ser Gly Gly Ser Leu Lys Gln Gln Gly Gly Ser Gly Gly
                245                 250                 255

Ser Phe Glu Met Ala Ser Lys Val Tyr Asp Pro Glu Gln Arg Lys Arg
            260                 265                 270

Met Ile Thr Gly Pro Gln Trp Trp Ala Arg Cys Lys Gln Met Asn Val
        275                 280                 285

Leu Asp Ser Phe Ile Asn Tyr Tyr Asp Ser Glu Lys His Ala Glu Asn
    290                 295                 300

Ala Val Ile Phe Leu His Gly Asn Ala Ala Ser Ser Tyr Leu Trp Arg
305                 310                 315                 320

His Val Val Pro His Ile Glu Pro Val Ala Arg Cys Ile Ile Pro Asp
                325                 330                 335

Leu Ile Gly Met Gly Lys Ser Gly Lys Ser Gly Asn Gly Ser Tyr Arg
            340                 345                 350

```
Leu Leu Asp His Tyr Lys Tyr Leu Thr Ala Trp Phe Glu Leu Leu Asn
        355             360                 365
Leu Pro Lys Lys Ile Ile Phe Val Gly His Asp Trp Gly Ala Ala Leu
    370             375                 380
Ala Phe His Tyr Ser Tyr Glu His Gln Asp Lys Ile Lys Ala Ile Val
385                 390                 395                 400
His Ala Glu Ser Val Val Asp Val Ile Glu Ser Trp Asp Glu Trp Pro
            405                 410                 415
Asp Ile Glu Glu Asp Ile Ala Leu Ile Lys Ser Glu Glu Gly Glu Lys
            420                 425                 430
Met Val Leu Glu Asn Asn Phe Phe Val Glu Thr Val Leu Pro Ser Lys
        435                 440                 445
Ile Met Arg Lys Leu Glu Pro Glu Glu Phe Ala Ala Tyr Leu Glu Pro
    450                 455                 460
Phe Lys Glu Lys Gly Glu Val Arg Arg Pro Thr Leu Ser Trp Pro Arg
465                 470                 475                 480
Glu Ile Pro Leu Val Lys Gly Gly Lys Pro Asp Val Val Gln Ile Val
            485                 490                 495
Arg Asn Tyr Asn Ala Tyr Leu Arg Ala Ser Asp Leu Pro Lys Met
            500                 505                 510
Phe Ile Glu Ser Asp Pro Gly Phe Phe Ser Asn Ala Ile Val Glu Gly
        515                 520                 525
Ala Lys Lys Phe Pro Asn Thr Glu Phe Val Lys Val Lys Gly Leu His
    530                 535                 540
Phe Ser Gln Glu Asp Ala Pro Asp Glu Met Gly Lys Tyr Ile Lys Ser
545                 550                 555                 560
Phe Val Glu Arg Val Leu Lys Asn Glu Gln
            565                 570
```